United States Patent [19]

Rybak et al.

[11] Patent Number: 5,955,073
[45] Date of Patent: Sep. 21, 1999

[54] SELECTIVE RNASE CYTOTOXIC REAGENTS

[75] Inventors: Susanna M. Rybak, Frederick; Richard J. Youle, Garrett Park; Dianne L. Newton, Rockville, all of Md.; Peter J. Nicholls, Berkshire, United Kingdom

[73] Assignee: The United States of America as represented by the Department of Health and Human Services, Washington, D.C.

[21] Appl. No.: 08/891,848

[22] Filed: Jul. 9, 1997

Related U.S. Application Data

[60] Division of application No. 08/125,462, Sep. 22, 1993, Pat. No. 5,840,840, which is a continuation-in-part of application No. 08/014,082, Feb. 4, 1993, abandoned, which is a continuation of application No. 07/779,195, Oct. 22, 1991, abandoned, which is a continuation-in-part of application No. 07/510,696, Apr. 20, 1990, abandoned.

[51] Int. Cl.⁶ .......................... A61K 38/46; C12N 15/54; C12N 15/62
[52] U.S. Cl. ..................... 424/94.61; 424/183.1; 435/199; 435/69.7; 530/350; 530/391.7; 536/23.2; 536/23.4
[58] Field of Search .......................... 514/2.12; 435/199, 435/69.7; 530/350, 391.7; 424/183.1, 94.61; 536/23.2, 23.4

[56] References Cited

PUBLICATIONS

Ardelt et al., *J. Biol Chem.* 256:245–251 (1991).
Beintema et al., *Biochem.* 27:4530–38 (1988).
Blank et al., Human body fluid ribonucleases: detection, interrelationships and significance 1:203–209 (ILR Press, London 1981).
Carlsson et al., *Biochem.* 173:723–737 (1978).
DeGraaf et al., *Eur. J. Biochem.* 73:107–114 (1977).
Endo et al., *J. Biol. Chem.*, 257:9054–9060 (1982).
Endo et al., *J. Biol Chem.* 258:2662–2667 (1983).
Endo et al., *J. Biol Chem.* 262:8128–8130 (1987).
Fett et al., *Biochem.* 24:5480–5485 (1985).
FitzGerald et al., *Proc. Natl. Acad. Sci. USA* 80:4134 (1983).
FitzGerald et al., *Cancer Res.* 47:1407–1410 (1987).
Gleich et al., *Proc. Natl. Acad. Sci. USA* 83:3146–3150 (1986).
Glukhov et al., *Arch. Neurol.* 38:398–603 (1976).
Gullberg et al., *Biophys. Biochem. Res. Comm.* 139(3):1239–1242 (1986).
Hoogenboom et al., *J. Immunol.* 144(8):3211–3217 (1990).
Johnson et al., *J. Biol. Chem.* 263:1295–1300 (1988).
Konisky, J., *Rev. Microbiol.* 36:125–144 (1982).
Kurachi et al., *Biochemistry* 24:1594–1599 (1985).
Leone et al., *J. Reprod., Fert.* 34:197–200 (1973).
MacGillivray et al., *Proc. Natl. Acad. Sci. USA* 79:2504–2408 (1982).
Marks et al., *Cancer Res.* 50:288–292 (1990).
Matousek, J., *Experientia* 29:858–859 (1973).
Moolten et al., *Immunol. Rev.* 62:47–73 (1982).
Nambiar et al., *Eur. J. Biochem.* 163:67–71 (1987).
O'Keefe et al., *J. Biol. Chem.* 260(2):932–937 (1985).
Pirker et al. *Cancer Res.* 45:751–757 (1985).
Prior et al., *Cell* 64:1017–1023 (1991).
Raso et al., *J. Biol. Chem.* 259(2):1143–1149 (1984).
Reddi, E., *Biochem. Biophys. Res. Commun.* 67:110–118 (1975).
Roth, J., *Cancer Res.* 23:657–666 (1963).
Rybak et al., *Biochem.* 25:3527–3531 (1988).
Rybak et al., "Human Cancer Immunology" in *Immunology & Allergy Clinics of America* (1990).
St. Clair et al., *Proc. Natl. Acad. Sci. USA* 94:8330–8334 (1987).
St. Clair et al., *Biochem.* 27:7263–7268 (1988).
Scott et al., *J. Natl. Cancer Inst.* 79(5):1163–1172 (1987).
Shapiro et al., *Biochem.* 26:5141–5146 (1987).
Slifman et al., *J. Immunol.* 137(9):2913–2917 (1988).
Trowbridge et al., *Nature* 294:171–173 (1981).
Vescia et al., *Cancer Res.* 40:3740–3744 (1980).
Youle et al., Immunoconjuncates: Antibody Conjugates in Radioimaging and Therapy of Cancer. Oxford, Oxford University Press (1987).
Rybak et al., *J. Biol Chem.*, vol. 266, No. 31, Nov. 5, 1991, pp. 21202–21207.

*Primary Examiner*—Keith D. Hendricks
*Attorney, Agent, or Firm*—Townsend and Townsend and Crew LLP

[57] ABSTRACT

The present invention relates to a selective cytotoxic RNase reagent. The reagent comprises a toxic moiety that is an RNase linked to a recognition moiety that binds a specific cell surface marker. Binding of the recognition moiety to a surface marker on a cell allows the toxic moiety to selectively kill the cell. To reduce immunogenicity, preferably the toxic moiety and the recognition moiety of the conjugate are endogenous to the species in which the reagent is intended for use. Cytotoxic reagents intended for use in humans preferably have as the toxic moiety a human ribonuclease, such as angiogenin, and as the recognition moiety as humanized chimeric antibody. The human ribonuclease and chimeric antibody preferably form a fused protein. The present invention also relates to pharmaceutical compositions including the cytotoxic reagent as well as treatment methods involving the use of the cytotoxic reagent.

12 Claims, 17 Drawing Sheets

C$_H$2-ANG:

----ANTIBODY  -C$_H$2-  JUNCTION          -----ANG---

A        P           E     F           Q      D     N     S

GCA    CCT         GAA   TTC         CAG    GAT   AAC   TCC
                    -EcoRI-

*FIG. 7.*

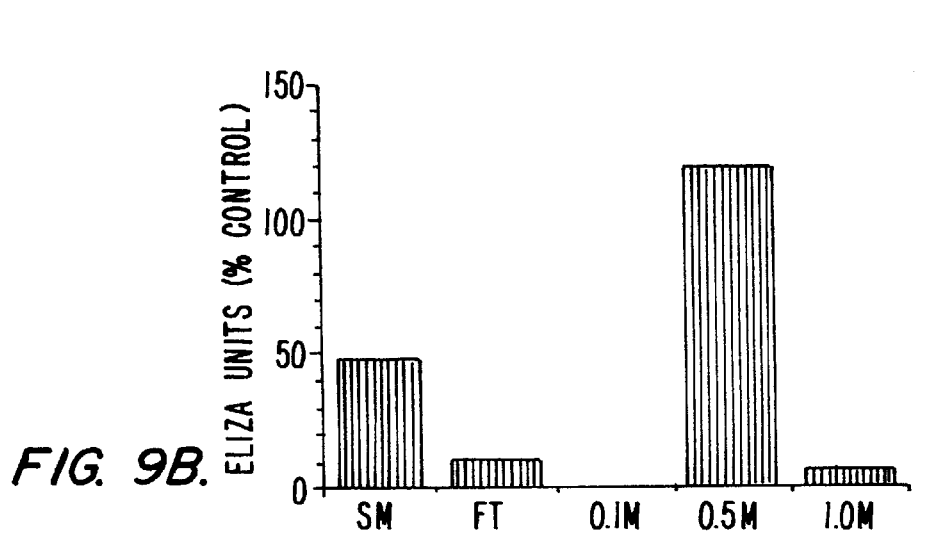
FIG. 9A.
FIG. 9B.
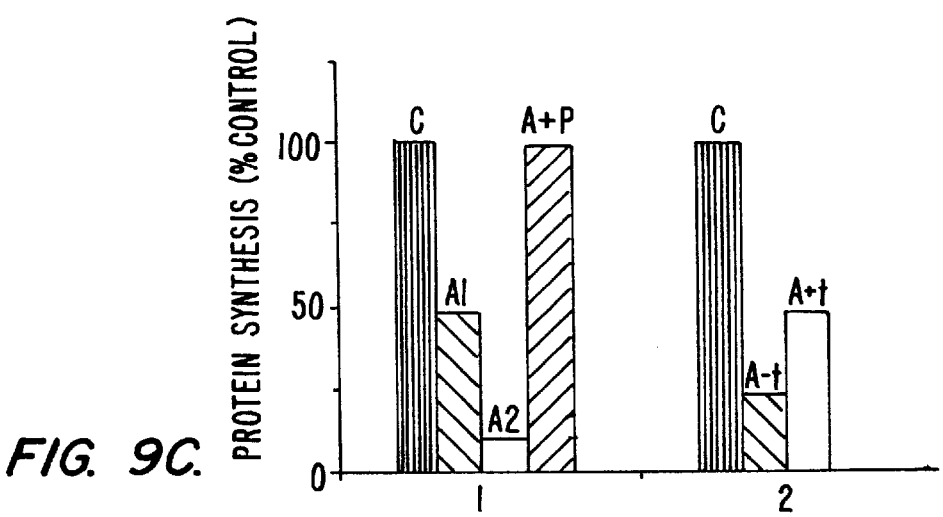
FIG. 9C.

```
                1                                                        *          50
FROG LECTIN     .....anwat  FqqkHi.int  piin.....Cn  tiMdnniyiv  ggqCKrvNTF
  ONCONASE      .....adwlt  FqkkHi.tnt  rdvd.....Cd  niMstnlf..  ..hCKdkNTF
       EDN      kppqftwaqw  FetqHinmts  qq.......Ct  naMqvinnyq  rr.CKnqNTF
       ECP      rppqftraqw  FaiqHislnp  pr.......Ct  iaMrainnyr  wr.CKnqNTF
       Ang      .aqddyryih  FltqHyd.ak  pkgrndeyCf  hmMknrrltr  p..CKdrNTF
   SEMINAL      ..kes.aaak  FerqHmdsgn  spsssnyCn   lmMccrkmtq  gk.CKpvNTF
   RNASE A      ..ket.aaak  FerqHmdsst  saasssnyCn  qmMksrnltk  dr.CKpvNTF 51                                                               100
FROG LECTIN     iissattvka  iCtgvi..nm  nvl.......  Sttrfqlntc  trts...itp
  ONCONASE      iysrpapvka  iCkgii.ask  nvlt.....t  Sefy..lsdC  ......nvts
       EDN      llttfanvvn  vCgnpnmtcp  snktrknchh  SgsqvplihC  nlttpspqni
       ECP      lrttfanvvn  vCgnqsircp  hnrtlnnchr  SrfrvpllhC  dlinpgaqni
       Ang      ihgnkndika  iCedrngqpy  rg...dlri   SksefqitiC  khkggs..sr
   SEMINAL      vheslаdvka  vCsqkkvtck  nqqt..ncyq  SkstmritdC  ret..gssky
   RNASE A      vheslаdvqa  vCsqknvack  nqqt..ncyq  SystmsitdC  ret..gssky 101                                      *                       150
FROG LECTIN     rpCpYssrta  tnyicVkCen  q.........  ..yPVHfagi  grcp......
  ONCONASE      rpCkYklkks  tnkfcVtCen  q.........  ..aPVHfvgv  gsc.......
       EDN      snCrYaqtpa  nmfyiVaCdn  rdqrrdppqy  pvvPVHldri  i.........
       ECP      snCrYadrpg  rrfyvVaCdn  rd.prdspry  pvvPVHldtt  i.........
       Ang      ppCrYgated  srvivVgCen  g.........  ..lPVHfdes  fitprh....
   SEMINAL      pnCaYkttqv  ekhiiVaCgg  k.........  psvPVHfdas  v.........
   RNASE A      pnCaYkttqa  nkhiiVaCeg  n.........  pyvPVHfdas  v.........
```

FIG. 19.

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 600 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: misc_feature
      (B) LOCATION: 115..492
      (D) OTHER INFORMATION: /note= "Angiogenin sequence cloned into
            the anti-transferrin receptor
            antibody/angiogenin fusion protein"

(xi) SEQUENCE DESCRIPTION: SEQ ID NO:1:

```
GGATCGAGAT CTCGATCCCG CGAAATTAAT ACGACTCACT ATAGGGGAAT TGTGAGCGGA      60

TAACAATTCC CCTCTAGAAA TAATTTTGTT TAACTTTAAG AAGGAGATAT ACATATGCAG     120

GATAACTCCA GGTACACACA CTTCCTGACC CAGCACTATG ATGCCAAACC ACAGGGCCGG     180

GATGACAGAT ACTGTGAAAG CATCATGAGG AGACGGGGCC TGACCTCACC CTGCAAAGAC     240

ATCAACACAT TTATTCATGG CAACAAGCGC AGCATCAAGG CCATCTGTGA AAACAAGAAT     300

GGAAACCCTC ACAGAGAAAA CCTAAGAATA AGCAAGTCTT CTTTCCAGGT CACCACTTGC     360

AAGCTACATG GAGGTTCCCC CTGGCCTCCA TGCCAGTACC GAGCCACAGC GGGGTTCAGA     420

AACGTTGTTG TTGCTTGTGA AAATGGCTTA CCTGTCCACT TGGATCAGTC AATTTTCCGT     480

CGTCCGTAAT AGGGATCCGG CTGCTAACAA GCCCGAAAG GAAGCTGAGT TGGCTGCTGC     540

CACCGCTGAG CAATAACTAG CATAACCCCT TGGGGCCTCT AAACGGGTCT TGAGGGGTTT     600
```

(2) INFORMATION FOR SEQ ID NO:2:

(i) SEQUENCE CHARACTERISTICS:
      (A) LENGTH: 6727 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: -
      (B) LOCATION: 1..6727
      (D) OTHER INFORMATION: /note= "pET-11d-ANG-E6 fusion protein
            sequence"

(xi) SEQUENCE DESCRIPTION: SEQ ID NO:2:

```
GGATCGAGAT CTCGATCCCG CGAAATTAAT ACGACTCACT ATAGGGGAAT TGTGAGCGGA      60

TAACAATTCC CCTCTAGAAA TAATTTTGTT TAACTTTAAG AAGGAGATAT ACATATGCAG     120

GATAACTCCA GGTACACACA CTTCCTGACC CAGCACTATG ATGCCAAACC ACAGGGCCGG     180

GATGACAGAT ACTGTGAAAG CATCATGAGG AGACGGGGCC TGACCTCACC CTGCAAAGAC     240

ATCAACACAT TTATTCATGG CAACAAGCGC AGCATCAAGG CCATCTGTGA AAACAAGAAT     300

GGAAACCCTC ACAGAGAAAA CCTAAGAATA AGCAAGTCTT CTTTCCAGGT CACCACTTGC     360

AAGCTACATG GAGGTTCCCC CTGGCCTCCA TGCCAGTACC GAGCCACAGC GGGGTTCAGA     420
```

```
AACGTTGTTG TTGCTTGTGA AAATGGCTTA CCTGTCCACT TGGATCAGTC AATTTTCCGT     480

CGTCCGGACA TCAAGATGAC CCAGTCTCCA TCTTCCATGT ATGCATCTCT AGGAGAGAGA     540

GTCACTTTCA CTTGCAAGGC GAGTCAGGAC ATTAATAACT ATTTATGCTG GTTCCAGCAG     600

AAACTAGGGA AATCTCCTAA GACCCTGATC TATCGTGCAA ACAGACTGGT AGATGGGGTC     660

CCATCAAGGT TCAGTGGCAG TGGATCTGGA CAAGATTATT CTCTCACCAT TAGCAGCTTG     720

GAGTATGAAG ATATGGGAAT TTATTATTGT CTACAGTATG ATGAGTTTCC GTACACGTTC     780

GGAGGGGGGA CCAAGCTGGA AATAAAAGAG GGTAAATCCT CAGGATCTGG CTCCGAATCC     840

AAAGAATTCG AGGTTCAGCT CCAGCAGTCT GGGACTGTAC TGGCAAGGCC TGGGGCTTCA     900

GTGAAGATGT CCTGCAAGGC TTCTGGCTAC ACCATTTCCA GCTACTGGAT GCACTGGATA     960

AAACAGAGGC CTGGACAGGG TCTGGACTGG ATTGTCGCTA TTGATCCTCG AAATAGTGAT    1020

ACTATTTACA ACCCGCAATT CAAACACAAG GCCAAACTGA CTGCAGTCAC CTCCACCAGC    1080

ACTGCCTACA TGGAACTCAA CAGCCTGACA AATGAGGACT CTGCGGTCTA TTACTGTACC    1140

CCTCTTTATT ACTTTGACTC CTGGGGCCAA GGCACCACTC TCACAGTCTC CTCATAATAA    1200

GGATCCGGCT GCTAACAAAG CCCGAAAGGA AGCTGAGTTG GCTGCTGCCA CCGCTGAGCA    1260

ATAACTAGCA TAACCCCTTG GGGCCTCTAA ACGGGTCTTG AGGGGTTTTT TGCTGAAAGG    1320

AGGAACTATA TCCGGATATC CCGCAAGAGG CCCGGCAGTA CCGGCATAAC CAAGCCTATG    1380

CCTACAGCAT CCAGGGTGAC GGTGCCGAGG ATGACGATGA GCGCATTGTT AGATTTCATA    1440

CACGGTGCCT GACTGCGTTA GCAATTTAAC TGTGATAAAC TACCGCATTA AAGCTTATCG    1500

ATGATAAGCT GTCAAACATG AGAATTCTTG AAGACGAAAG GGCCTCGTGA TACGCCTATT    1560

TTTATAGGTT AATGTCATGA TAATAATGGT TTCTTAGACG TCAGGTGGCA CTTTTCGGGG    1620

AAATGTGCGC GGAACCCCTA TTTGTTTATT TTTCTAAATA CATTCAAATA TGTATCCGCT    1680

CATGAGACAA TAACCCTGAT AAATGCTTCA ATAATATTGA AAAGGAAGA GTATGAGTAT    1740

TCAACATTTC CGTGTCGCCC TTATTCCCTT TTTTGCGGCA TTTTGCCTTC CTGTTTTTGC    1800

TCACCCAGAA ACGCTGGTGA AAGTAAAAGA TGCTGAAGAT CAGTTGGGTG CACGAGTGGG    1860

TTACATCGAA CTGGATCTCA ACAGCGGTAA GATCCTTGAG AGTTTTCGCC CCGAAGAACG    1920

TTTTCCAATG ATGAGCACTT TTAAAGTTCT GCTATGTGGC GCGGTATTAT CCCGTGTTGA    1980

CGCCGGGCAA GAGCAACTCG GTCGCCGCAT ACACTATTCT CAGAATGACT TGGTTGAGTA    2040

CTCACCAGTC ACAGAAAAGC ATCTTACGGA TGGCATGACA GTAAGAGAAT TATGCAGTGC    2100

TGCCATAACC ATGAGTGATA ACACTGCGGC CAACTTACTT CTGACAACGA TCGGAGGACC    2160

GAAGGAGCTA ACCGCTTTTT TGCACAACAT GGGGGATCAT GTAACTCGCC TTGATCGTTG    2220

GGAACCGGAG CTGAATGAAG CCATACCAAA CGACGAGCGT GACACCACGA TGCCTGCAGC    2280

AATGGCAACA ACGTTGCGCA AACTATTAAC TGGCGAACTA CTTACTCTAG CTTCCCGGCA    2340

ACAATTAATA GACTGGATGG AGGCGGATAA AGTTGCAGGA CCACTTCTGC GCTCGGCCCT    2400

TCCGGCTGGC TGGTTTATTG CTGATAAATC TGGAGCCGGT GAGCGTGGGT CTCGCGGTAT    2460

CATTGCAGCA CTGGGGCCAG ATGGTAAGCC CTCCCGTATC GTAGTTATCT ACACGACGGG    2520

GAGTCAGGCA ACTATGGATG AACGAAATAG ACAGATCGCT GAGATAGGTG CCTCACTGAT    2580

TAAGCATTGG TAACTGTCAG ACCAAGTTTA CTCATATATA CTTTAGATTG ATTTAAAACT    2640

TCATTTTTAA TTTAAAAGGA TCTAGGTGAA GATCCTTTTT GATAATCTCA TGACCAAAAT    2700

CCCTTAACGT GAGTTTTCGT TCCACTGAGC GTCAGACCCC GTAGAAAAGA TCAAAGGATC    2760

TTCTTGAGAT CCTTTTTTTC TGCGCGTAAT CTGCTGCTTG CAAACAAAAA AACCACCGCT    2820
```

```
ACCAGCGGTG GTTTGTTTGC CGGATCAAGA GCTACCAACT CTTTTTCCGA AGGTAACTGG    2880

CTTCAGCAGA GCGCAGATAC CAAATACTGT CCTTCTAGTG TAGCCGTAGT TAGGCCACCA    2940

CTTCAAGAAC TCTGTAGCAC CGCCTACATA CCTCGCTCTG CTAATCCTGT TACCAGTGGC    3000

TGCTGCCAGT GGCGATAAGT CGTGTCTTAC CGGGTTGGAC TCAAGACGAT AGTTACCGGA    3060

TAAGGCGCAG CGGTCGGGCT GAACGGGGGG TTCGTGCACA CAGCCCAGCT TGGAGCGAAC    3120

GACCTACACC GAACTGAGAT ACCTACAGCG TGAGCTATGA GAAAGCGCCA CGCTTCCCGA    3180

AGGGAGAAAG GCGGACAGGT ATCCGGTAAG CGGCAGGGTC GGAACAGGAG AGCGCACGAG    3240

GGAGCTTCCA GGGGGAAACG CCTGGTATCT TTATAGTCCT GTCGGGTTTC GCCACCTCTG    3300

ACTTGAGCGT CGATTTTTGT GATGCTCGTC AGGGGGGCGG AGCCTATGGA AAAACGCCAG    3360

CAACGCGGCC TTTTTACGGT TCCTGGCCTT TTGCTGGCCT TTTGCTCACA TGTTCTTTCC    3420

TGCGTTATCC CCTGATTCTG TGGATAACCG TATTACCGCC TTTGAGTGAG CTGATACCGC    3480

TCGCCGCAGC CGAACGACCG AGCGCAGCGA GTCAGTGAGC GAGGAAGCGG AAGAGCGCCT    3540

GATGCGGTAT TTTCTCCTTA CGCATCTGTG CGGTATTTCA CACCGCATAT ATGGTGCACT    3600

CTCAGTACAA TCTGCTCTGA TGCCGCATAG TTAAGCCAGT ATACACTCCG CTATCGCTAC    3660

GTGACTGGGT CATGGCTGCG CCCCGACACC CGCCAACACC CGCTGACGCG CCCTGACGGG    3720

CTTGTCTGCT CCCGGCATCC GCTTACAGAC AAGCTGTGAC CGTCTCCGGG AGCTGCATGT    3780

GTCAGAGGTT TTCACCGTCA TCACCGAAAC GCGCGAGGCA GCTGCGGTAA AGCTCATCAG    3840

CGTGGTCGTG AAGCGATTCA CAGATGTCTG CCTGTTCATC CGCGTCCAGC TCGTTGAGTT    3900

TCTCCAGAAG CGTTAATGTC TGGCTTCTGA TAAAGCGGGC CATGTTAAGG GCGGTTTTTT    3960

CCTGTTTGGT CACTGATGCC TCCGTGTAAG GGGGATTTCT GTTCATGGGG GTAATGATAC    4020

CGATGAAACG AGAGAGGATG CTCACGATAC GGGTTACTGA TGATGAACAT GCCCGGTTAC    4080

TGGAACGTTG TGAGGGTAAA CAACTGGCGG TATGGATGCG GCGGGACCAG AGAAAAATCA    4140

CTCAGGGTCA ATGCCAGCGC TTCGTTAATA CAGATGTAGG TGTTCCACAG GGTAGCCAGC    4200

AGCATCCTGC GATGCAGATC CGGAACATAA TGGTGCAGGG CGCTGACTTC CGCGTTTCCA    4260

GACTTTACGA AACACGGAAA CCGAAGACCA TTCATGTTGT TGCTCAGGTC GCAGACGTTT    4320

TGCAGCAGCA GTCGCTTCAC GTTCGCTCGC GTATCGGTGA TTCATTCTGC TAACCAGTAA    4380

GGCAACCCCG CCAGCCTAGC CGGGTCCTCA ACGACAGGAG CACGATCATG CGCACCCGTG    4440

GCCAGGACCC AACGCTGCCC GAGATGCGCC GCGTGCGGCT GCTGGAGATG CGGACGCGA    4500

TGGATATGTT CTGCCAAGGG TTGGTTTGCG CATTCACAGT TCTCCGCAAG AATTGATTGG    4560

CTCCAATTCT TGGAGTGGTG AATCCGTTAG CGAGGTGCCG CCGGCTTCCA TTCAGGTCGA    4620

GGTGGCCCGG CTCCATGCAC CGCGACGCAA CGCGGGGAGG CAGACAAGGT ATAGGGCGGC    4680

GCCTACAATC CATGCCAACC CGTTCCATGT GCTCGCCGAG GCGGCATAAA TCGCCGTGAC    4740

GATCAGCGGT CCAGTGATCG AAGTTAGGCT GGTAAGAGCC GCGAGCGATC CTTGAAGCTG    4800

TCCCTGATGG TCGTCATCTA CCTGCCTGGA CAGCATGGCC TGCAACGCGG GCATCCCGAT    4860

GCCGCCGGAA GCGAGAAGAA TCATAATGGG GAAGGCCATC CAGCCTCGCG TCGCGAACGC    4920

CAGCAAGACG TAGCCCAGCG CGTCGGCCGC CATGCCGGCG ATAATGGCCT GCTTCTCGCC    4980

GAAACGTTTG GTGGCGGGAC CAGTGACGAA GGCTTGAGCG AGGGCGTGCA AGATTCCGAA    5040

TACCGCAAGC GACAGGCCGA TCATCGTCGC GCTCCAGCGA AAGCGGTCCT CGCCGAAAAT    5100

GACCCAGAGC GCTGCCGGCA CCTGTCCTAC GAGTTGCATG ATAAAGAAGA CAGTCATAAG    5160

TGCGGCGACG ATAGTCATGC CCCGCGCCCA CCGGAAGGAG CTGACTGGGT TGAAGGCTCT    5220
```

-continued

```
CAAGGGCATC GGTCGAGATC CCGGTGCCTA ATGAGTGAGC TAACTTACAT TAATTGCGTT    5280

GCGCTCACTG CCCGCTTTCC AGTCGGGAAA CCTGTCGTGC CAGCTGCATT AATGAATCGG    5340

CCAACGCGCG GGGAGAGGCG GTTTGCGTAT TGGGCGCCAG GGTGGTTTTT CTTTTCACCA    5400

GTGAGACGGG CAACAGCTGA TTGCCCTTCA CCGCCTGGCC CTGAGAGAGT TGCAGCAAGC    5460

GGTCCACGCT GGTTTGCCCC AGCAGGCGAA AATCCTGTTT GATGGTGGTT AACGGCGGGA    5520

TATAACATGA GCTGTCTTCG GTATCGTCGT ATCCCACTAC CGAGATATCC GCACCAACGC    5580

GCAGCCCGGA CTCGGTAATG GCGCGCATTG CGCCCAGCGC CATCTGATCG TTGGCAACCA    5640

GCATCGCAGT GGGAACGATG CCCTCATTCA GCATTTGCAT GGTTTGTTGA AAACCGGACA    5700

TGGCACTCCA GTCGCCTTCC CGTTCCGCTA TCGGCTGAAT TTGATTGCGA GTGAGATATT    5760

TATGCCAGCC AGCCAGACGC AGACGCGCCG AGACAGAACT TAATGGGCCC GCTAACAGCG    5820

CGATTTGCTG GTGACCCAAT GCGACCAGAT GCTCCACGCC CAGTCGCGTA CCGTCTTCAT    5880

GGGAGAAAAT AATACTGTTG ATGGGTGTCT GGTCAGAGAC ATCAAGAAAT AACGCCGGAA    5940

CATTAGTGCA GGCAGCTTCC ACAGCAATGG CATCCTGGTC ATCCAGCGGA TAGTTAATGA    6000

TCAGCCCACT GACGCGTTGC GCGAGAAGAT TGTGCACCGC CGCTTTACAG GCTTCGACGC    6060

CGCTTCGTTC TACCATCGAC ACCACCACGC TGGCACCCAG TTGATCGGCG CGAGATTTAA    6120

TCGCCGCGAC AATTTGCGAC GGCGCGTGCA GGGCCAGACT GGAGGTGGCA ACGCCAATCA    6180

GCAACGACTG TTTGCCCGCC AGTTGTTGTG CCACGCGGTT GGGAATGTAA TTCAGCTCCG    6240

CCATCGCCGC TTCCACTTTT TCCCGCGTTT TCGCAGAAAC GTGGCTGGCC TGGTTCACCA    6300

CGCGGGAAAC GGTCTGATAA GAGACACCGG CATACTCTGC GACATCGTAT AACGTTACTG    6360

GTTTCACATT CACCACCCTG AATTGACTCT CTTCCGGGCG CTATCATGCC ATACCGCGAA    6420

AGGTTTTGCG CCATTCGATG GTGTCCGGGA TCTCGACGCT CTCCCTTATG CGACTCCTGC    6480

ATTAGGAAGC AGCCCAGTAG TAGGTTGAGG CCGTTGAGCA CCGCCGCCGC AAGGAATGGT    6540

GCATGCAAGG AGATGGCGCC CAACAGTCCC CCGGCCACGG GGCCTGCCAC CATACCCACG    6600

CCGAAACAAG CGCTCATGAG CCCGAAGTGG CGAGCCCGAT CTTCCCCATC GGTGATGTCG    6660

GCGATATAGG CGCCAGCAAC CGCACCTGTG GCGCCGGTGA TGCCGGCCAC GATGCGTCCG    6720

GCGTAGA                                                              6727
```

(2) INFORMATION FOR SEQ ID NO:3:

(i) SEQUENCE CHARACTERISTICS:
        (A) LENGTH: 1320 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1320
        (D) OTHER INFORMATION: /note= "pET-11d-ANG-FB-E6-His6 fusion
            protein coding sequence"

(ix) FEATURE:
        (A) NAME/KEY: misc_feature
        (B) LOCATION: 115..486
        (D) OTHER INFORMATION: /note= "Angiogenin (ANG) sequence"

(ix) FEATURE:
        (A) NAME/KEY: misc_feature
        (B) LOCATION: 487..525
        (D) OTHER INFORMATION: /note= "Spacer sequence between
            Angiogenin and E6 single chain antibody"

```
    (ix) FEATURE:
         (A) NAME/KEY: misc_feature
         (B) LOCATION: 526..1233
         (D) OTHER INFORMATION: /note= "Variable heavy and light chains
             of E6 single chain antibody (sFv) with
             linker sequence"

(ix) FEATURE:
         (A) NAME/KEY: misc_feature
         (B) LOCATION: 526..846
         (D) OTHER INFORMATION: /note= "E6 Variable light chain (V-L)
             sequence"

(ix) FEATURE:
         (A) NAME/KEY: misc_feature
         (B) LOCATION: 847..888
         (D) OTHER INFORMATION: /note= "Linker sequence between E6
             light and heavy chain"

(ix) FEATURE:
         (A) NAME/KEY: misc_feature
         (B) LOCATION: 889..1233
         (D) OTHER INFORMATION: /note= "E6 Variable heavy chain (V-H)
             sequence"

(ix) FEATURE:
         (A) NAME/KEY: misc_feature
         (B) LOCATION: 1234..1251
         (D) OTHER INFORMATION: /note= "string of 6 His codon tail to
             aid in purification"

(xi) SEQUENCE DESCRIPTION: SEQ ID NO:3:

GGATCGAGAT CTCGATCCCG CGAAATTAAT ACGACTCACT ATAGGGGAAT TGTGAGCGGA      60

TAACAATTCC CCTCTAGAAA TAATTTTGTT TAACTTTAAG AAGGAGATAT ACATATGCAG     120

GATAACTCCA GGTACACACA CTTCCTGACC CAGCACTATG ATGCCAAACC ACAGGGCCGG     180

GATGACAGAT ACTGTGAAAG CATCATGAGG AGACGGGGCC TGACCTCACC CTGCAAAGAC     240

ATCAACACAT TTATTCATGG CAACAAGCGC AGCATCAAGG CCATCTGTGA AAACAAGAAT     300

GGAAACCCTC ACAGAGAAAA CCTAAGAATA AGCAAGTCTT CTTTCCAGGT CACCACTTGC     360

AAGCTACATG GAGGTTCCCC CTGGCCTCCA TGCCAGTACC GAGCCACAGC GGGGTTCAGA     420

AACGTTGTTG TTGCTTGTGA AAATGGCTTA CCTGTCCACT TGGATCAGTC AATTTTCCGT     480

CGTCCGGCCA AGAAACTGAA CGACGCTCAG GCGCCGAAGA GTGATGACAT CAAGATGACC     540

CAGTCTCCAT CTTCCATGTA TGCATCTCTA GGAGAGAGAG TCACTTTCAC TTGCAAGGCG     600

AGTCAGGACA TTAATAACTA TTTATGCTGG TTCCAGCAGA AACTAGGGAA ATCTCCTAAG     660

ACCCTGATCT ATCGTGCAAA CAGACTGGTA GATGGGGTCC CATCAAGGTT CAGTGGCAGT     720

GGATCTGGAC AAGATTATTC TCTCACCATT AGCAGCTTGG AGTATGAAGA TATGGGAATT     780

TATTATTGTC TACAGTATGA TGAGTTTCCG TACACGTTCG GAGGGGGGAC CAAGCTGGAA     840

ATAAAAGAGG GTAAATCCTC AGGATCTGGC TCCGAATCCA AGAATTCGA GGTTCAGCTC      900

CAGCAGTCTG GGACTGTACT GGCAAGGCCT GGGGCTTCAG TGAAGATGTC CTGCAAGGCT     960

TCTGGCTACA CCATTTCCAG CTACTGGATG CACTGGATAA ACAGAGGCC TGGACAGGGT     1020

CTGGACTGGA TTGTCGCTAT TGATCCTCGA AATAGTGATA CTATTTACAA CCCGCAATTC    1080

AAACACAAGG CCAAACTGAC TGCAGTCACC TCCACCAGCA CTGCCTACAT GGAACTCAAC    1140

AGCCTGACAA ATGAGGACTC TGCGGTCTAT TACTGTACCC CTCTTTATTA CTTTGACTCC    1200

TGGGGCCAAG GCACCACTCT CACAGTCTCC TCACATCACC ATCACCATCA CTAATAGGGA    1260

TCCGGCTGCT AACAAAGCCC GAAAGGAAGC TGAGTTGGCT GCTGCCACCG CTGAGCAATA    1320

(2) INFORMATION FOR SEQ ID NO:4:
```

(i) SEQUENCE CHARACTERISTICS:
(A) LENGTH: 405 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: -
(B) LOCATION: 1..405
(D) OTHER INFORMATION: /note= "synthetic eosinophil derived neurotoxin (EDN) gene sequence"

(xi) SEQUENCE DESCRIPTION: SEQ ID NO:4:

```
ATGAAACCGC CGCAGTTCAC TTGGGCTCAG TGGTTCGAAA CTCAGCATAT CAACATGACT     60

TCTCAGCAGT GCACTAACGC TATGCAGGTT ATCAACAACT ACCAGCGTCG TTGCAAAAAC    120

CAGAACACTT TCCTGCTGAC TACTTTCGCT AACGTTGTTA ACGTTTGCGG TAACCCGAAC    180

ATGACTTGCC CGTCTAACAA AACTCGTAAA AACTGCCATC ATTCTGGTTC TCAGGTTCCG    240

CTGATCCATT GCAACCTGAC TACTCCGTCT CCGCAGAACA TCTCTAACTG CCGTTACGCT    300

CAGACTCCGG CTAACATGTT CTACATCGTT GCTTGCGACA ACCGTGACCA GCGTCGTGAC    360

CCGCCGCAGT ACCCGGTTGT TCCGGTTCAT CTGGACCGTA TCATC                    405
```

(2) INFORMATION FOR SEQ ID NO:5:

(i) SEQUENCE CHARACTERISTICS:
(A) LENGTH: 6799 base pairs
(B) TYPE: nucleic acid
(C) STRANDEDNESS: single
(D) TOPOLOGY: linear (ii) MOLECULE TYPE: DNA (ix) FEATURE:
(A) NAME/KEY: -
(B) LOCATION: 1..6799
(D) OTHER INFORMATION: /note= "pET-11d-E6-FB-EDN fusion protein sequence"

(xi) SEQUENCE DESCRIPTION: SEQ ID NO:5:

```
GGATCGAGAT CTCGATCCCG CGAAATTAAT ACGACTCACT ATAGGGGAAT TGTGAGCGGA     60

TAACAATTCC CCTCTAGAAA TAATTTTGTT TAACTTTAAG AAGGAGATAT ACATATGGAC    120

ATCAAGATGA CCCAGTCTCC ATCTTCCATG TATGCATCTC TAGGAGAGAG AGTCACTTTC    180

ACTTGCAAGG CGAGTCAGGA CATTAATAAC TATTTATGCT GGTTCCAGCA GAAACTAGGG    240

AAATCTCCTA AGACCCTGAT CTATCGTGCA AACAGACTGG TAGATGGGGT CCCATCAAGG    300

TTCAGTGGCA GTGGATCTGG ACAAGATTAT TCTCTCACCA TTAGCAGCTT GGAGTATGAA    360

GATATGGGAA TTTATTATTG TCTACAGTAT GATGAGTTTC CGTACACGTT CGGAGGGGGG    420

ACCAAGCTGG AAATAAAAGA GGGTAAATCC TCAGGATCTG GCTCCGAATC CAAAGAATTC    480

GAGGTTCAGC TCCAGCAGTC TGGGACTGTA CTGGCAAGGC CTGGGGCTTC AGTGAAGATG    540

TCCTGCAAGG CTTCTGGCTA CACCATTTCC AGCTACTGGA TGCACTGGAT AAAACAGAGG    600

CCTGGACAGG GTCTGGACTG GATTGTCGCT ATTGATCCTC GAAATAGTGA TACTATTTAC    660

AACCCGCAAT TCAAACACAA GGCCAAACTG ACTGCAGTCA CCTCCACCAG CACTGCCTAC    720

ATGGAACTCA ACAGCCTGAC AAATGAGGAC TCTGCGGTCT ATTACTGTAC CCCTCTTTAT    780

TACTTTGACT CCTGGGGCCA AGGCACCACT CTCACAGTCT CCTCAGCCAA GAAACTGAAC    840

GACGCTCAGG CGCCGAAGAG TGATAAACCG CCGCAGTTCA CTTGGGCTCA GTGGTTCGAA    900

ACTCAGCATA TCAACATGAC TTCTCAGCAG TGCACTAACG CTATGCAGGT TATCAACAAC    960
```

```
TACCAGCGTC GTTGCAAAAA CCAGAACACT TTCCTGCTGA CTACTTTCGC TAACGTTGTT   1020

AACGTTTGCG GTAACCCGAA CATGACTTGC CCGTCTAACA AAACTCGTAA AAACTGCCAT   1080

CATTCTGGTT CTCAGGTTCC GCTGATCCAT TGCAACCTGA CTACTCCGTC TCCGCAGAAC   1140

ATCTCTAACT GCCGTTACGC TCAGACTCCG GCTAACATGT TCTACATCGT TGCTTGCGAC   1200

AACCGTGACC AGCGTCGTGA CCCGCCGCAG TACCCGGTTG TTCCGGTTCA TCTGGACCGT   1260

ATCATCTAAT AGGGATCCGG CTGCTAACAA AGCCCGAAAG GAAGCTGAGT TGGCTGCTGC   1320

CACCGCTGAG CAATAACTAG CATAACCCCT TGGGGCCTCT AAACGGGTCT TGAGGGGTTT   1380

TTTGCTGAAA GGAGGAACTA TATCCGGATA TCCCGCAAGA GGCCCGGCAG TACCGGCATA   1440

ACCAAGCCTA TGCCTACAGC ATCCAGGGTG ACGGTGCCGA GGATGACGAT GAGCGCATTG   1500

TTAGATTTCA TACACGGTGC CTGACTGCGT TAGCAATTTA ACTGTGATAA ACTACCGCAT   1560

TAAAGCTTAT CGATGATAAG CTGTCAAACA TGAGAATTCT TGAAGACGAA AGGGCCTCGT   1620

GATACGCCTA TTTTTATAGG TTAATGTCAT GATAATAATG GTTTCTTAGA CGTCAGGTGG   1680

CACTTTTCGG GGAAATGTGC GCGGAACCCC TATTTGTTTA TTTTTCTAAA TACATTCAAA   1740

TATGTATCCG CTCATGAGAC AATAACCCTG ATAAATGCTT CAATAATATT GAAAAAGGAA   1800

GAGTATGAGT ATTCAACATT TCCGTGTCGC CCTTATTCCC TTTTTTGCGG CATTTTGCCT   1860

TCCTGTTTTT GCTCACCCAG AAACGCTGGT GAAAGTAAAA GATGCTGAAG ATCAGTTGGG   1920

TGCACGAGTG GGTTACATCG AACTGGATCT CAACAGCGGT AAGATCCTTG AGAGTTTTCG   1980

CCCCGAAGAA CGTTTTCCAA TGATGAGCAC TTTTAAAGTT CTGCTATGTG GCGCGGTATT   2040

ATCCCGTGTT GACGCCGGGC AAGAGCAACT CGGTCGCCGC ATACACTATT CTCAGAATGA   2100

CTTGGTTGAG TACTCACCAG TCACAGAAAA GCATCTTACG GATGGCATGA CAGTAAGAGA   2160

ATTATGCAGT GCTGCCATAA CCATGAGTGA TAACACTGCG GCCAACTTAC TTCTGACAAC   2220

GATCGGAGGA CCGAAGGAGC TAACCGCTTT TTTGCACAAC ATGGGGGATC ATGTAACTCG   2280

CCTTGATCGT TGGGAACCGG AGCTGAATGA AGCCATACCA AACGACGAGC GTGACACCAC   2340

GATGCCTGCA GCAATGGCAA CAACGTTGCG CAAACTATTA ACTGGCGAAC TACTTACTCT   2400

AGCTTCCCGG CAACAATTAA TAGACTGGAT GGAGGCGGAT AAAGTTGCAG GACCACTTCT   2460

GCGCTCGGCC CTTCCGGCTG GCTGGTTTAT TGCTGATAAA TCTGGAGCCG GTGAGCGTGG   2520

GTCTCGCGGT ATCATTGCAG CACTGGGGCC AGATGGTAAG CCCTCCCGTA TCGTAGTTAT   2580

CTACACGACG GGGAGTCAGG CAACTATGGA TGAACGAAAT AGACAGATCG CTGAGATAGG   2640

TGCCTCACTG ATTAAGCATT GGTAACTGTC AGACCAAGTT TACTCATATA TACTTTAGAT   2700

TGATTTAAAA CTTCATTTTT AATTTAAAAG GATCTAGGTG AAGATCCTTT TTGATAATCT   2760

CATGACCAAA ATCCCTTAAC GTGAGTTTTC GTTCCACTGA GCGTCAGACC CCGTAGAAAA   2820

GATCAAAGGA TCTTCTTGAG ATCCTTTTTT TCTGCGCGTA ATCTGCTGCT TGCAAACAAA   2880

AAAACCACCG CTACCAGCGG TGGTTTGTTT GCCGGATCAA GAGCTACCAA CTCTTTTTCC   2940

GAAGGTAACT GGCTTCAGCA GAGCGCAGAT ACCAAATACT GTCCTTCTAG TGTAGCCGTA   3000

GTTAGGCCAC CACTTCAAGA ACTCTGTAGC ACCGCCTACA TACCTCGCTC TGCTAATCCT   3060

GTTACCAGTG GCTGCTGCCA GTGGCGATAA GTCGTGTCTT ACCGGGTTGG ACTCAAGACG   3120

ATAGTTACCG GATAAGGCGC AGCGGTCGGG CTGAACGGGG GGTTCGTGCA CACAGCCCAG   3180

CTTGGAGCGA ACGACCTACA CCGAACTGAG ATACCTACAG CGTGAGCTAT GAGAAAGCGC   3240

CACGCTTCCC GAAGGGAGAA AGGCGGACAG GTATCCGGTA AGCGGCAGGG TCGGAACAGG   3300

AGAGCGCACG AGGGAGCTTC CAGGGGGAAA CGCCTGGTAT CTTTATAGTC CTGTCGGGTT   3360
```

```
TCGCCACCTC TGACTTGAGC GTCGATTTTT GTGATGCTCG TCAGGGGGGC GGAGCCTATG    3420

GAAAAACGCC AGCAACGCGG CCTTTTTACG GTTCCTGGCC TTTTGCTGGC CTTTTGCTCA    3480

CATGTTCTTT CCTGCGTTAT CCCCTGATTC TGTGGATAAC CGTATTACCG CCTTTGAGTG    3540

AGCTGATACC GCTCGCCGCA GCCGAACGAC CGAGCGCAGC GAGTCAGTGA GCGAGGAAGC    3600

GGAAGAGCGC CTGATGCGGT ATTTTCTCCT TACGCATCTG TGCGGTATTT CACACCGCAT    3660

ATATGGTGCA CTCTCAGTAC AATCTGCTCT GATGCCGCAT AGTTAAGCCA GTATACACTC    3720

CGCTATCGCT ACGTGACTGG GTCATGGCTG CGCCCCGACA CCCGCCAACA CCCGCTGACG    3780

CGCCCTGACG GGCTTGTCTG CTCCCGGCAT CCGCTTACAG ACAAGCTGTG ACCGTCTCCG    3840

GGAGCTGCAT GTGTCAGAGG TTTTCACCGT CATCACCGAA ACGCGCGAGG CAGCTGCGGT    3900

AAAGCTCATC AGCGTGGTCG TGAAGCGATT CACAGATGTC TGCCTGTTCA TCCGCGTCCA    3960

GCTCGTTGAG TTTCTCCAGA AGCGTTAATG TCTGGCTTCT GATAAAGCGG GCCATGTTAA    4020

GGGCGGTTTT TTCCTGTTTG GTCACTGATG CCTCCGTGTA AGGGGGATTT CTGTTCATGG    4080

GGGTAATGAT ACCGATGAAA CGAGAGAGGA TGCTCACGAT ACGGGTTACT GATGATGAAC    4140

ATGCCCGGTT ACTGGAACGT TGTGAGGGTA ACAACTGGC GGTATGGATG CGGCGGGACC    4200

AGAGAAAAAT CACTCAGGGT CAATGCCAGC GCTTCGTTAA TACAGATGTA GGTGTTCCAC    4260

AGGGTAGCCA GCAGCATCCT GCGATGCAGA TCCGGAACAT AATGGTGCAG GGCGCTGACT    4320

TCCGCGTTTC CAGACTTTAC GAAACACGGA AACCGAAGAC CATTCATGTT GTTGCTCAGG    4380

TCGCAGACGT TTTGCAGCAG CAGTCGCTTC ACGTTCGCTC GCGTATCGGT GATTCATTCT    4440

GCTAACCAGT AAGGCAACCC CGCCAGCCTA GCCGGGTCCT CAACGACAGG AGCACGATCA    4500

TGCGCACCCG TGGCCAGGAC CCAACGCTGC CCGAGATGCG CCGCGTGCGG CTGCTGGAGA    4560

TGGCGGACGC GATGGATATG TTCTGCCAAG GGTTGGTTTG CGCATTCACA GTTCTCCGCA    4620

AGAATTGATT GGCTCCAATT CTTGGAGTGG TGAATCCGTT AGCGAGGTGC CGCCGGCTTC    4680

CATTCAGGTC GAGGTGGCCC GGCTCCATGC ACCGCGACGC AACGCGGGGA GGCAGACAAG    4740

GTATAGGGCG CGCCTACAA TCCATGCCAA CCCGTTCCAT GTGCTCGCCG AGGCGGCATA    4800

AATCGCCGTG ACGATCAGCG GTCCAGTGAT CGAAGTTAGG CTGGTAAGAG CCGCGAGCGA    4860

TCCTTGAAGC TGTCCCTGAT GGTCGTCATC TACCTGCCTG GACAGCATGG CCTGCAACGC    4920

GGGCATCCCG ATGCCGCCGG AAGCGAGAAG AATCATAATG GGGAAGGCCA TCCAGCCTCG    4980

CGTCGCGAAC GCCAGCAAGA CGTAGCCCAG CGCGTCGGCC GCCATGCCGG CGATAATGGC    5040

CTGCTTCTCG CCGAAACGTT TGGTGGCGGG ACCAGTGACG AAGGCTTGAG CGAGGGCGTG    5100

CAAGATTCCG AATACCGCAA GCGACAGGCC GATCATCGTC GCGCTCCAGC GAAAGCGGTC    5160

CTCGCCGAAA ATGACCCAGA GCGCTGCCGG CACCTGTCCT ACGAGTTGCA TGATAAAGAA    5220

GACAGTCATA AGTGCGGCGA CGATAGTCAT GCCCCGCGCC CACCGGAAGG AGCTGACTGG    5280

GTTGAAGGCT CTCAAGGGCA TCGGTCGAGA TCCCGGTGCC TAATGAGTGA GCTAACTTAC    5340

ATTAATTGCG TTGCGCTCAC TGCCCGCTTT CCAGTCGGGA AACCTGTCGT GCCAGCTGCA    5400

TTAATGAATC GGCCAACGCG CGGGGAGAGG CGGTTTGCGT ATTGGGCGCC AGGGTGGTTT    5460

TTCTTTTCAC CAGTGAGACG GGCAACAGCT GATTGCCCTT CACCGCCTGG CCCTGAGAGA    5520

GTTGCAGCAA GCGGTCCACG CTGGTTTGCC CCAGCAGGCG AAAATCCTGT TTGATGGTGG    5580

TTAACGGCGG GATATAACAT GAGCTGTCTT CGGTATCGTC GTATCCCACT ACCGAGATAT    5640

CCGCACCAAC GCGCAGCCCG GACTCGGTAA TGGCGCGCAT TGCGCCCAGC GCCATCTGAT    5700

CGTTGGCAAC CAGCATCGCA GTGGGAACGA TGCCCTCATT CAGCATTTGC ATGGTTTGTT    5760
```

-continued

```
GAAAACCGGA CATGGCACTC CAGTCGCCTT CCCGTTCCGC TATCGGCTGA ATTTGATTGC      5820

GAGTGAGATA TTTATGCCAG CCAGCCAGAC GCAGACGCGC CGAGACAGAA CTTAATGGGC      5880

CCGCTAACAG CGCGATTTGC TGGTGACCCA ATGCGACCAG ATGCTCCACG CCCAGTCGCG      5940

TACCGTCTTC ATGGGAGAAA ATAATACTGT TGATGGGTGT CTGGTCAGAG ACATCAAGAA      6000

ATAACGCCGG AACATTAGTG CAGGCAGCTT CCACAGCAAT GGCATCCTGG TCATCCAGCG      6060

GATAGTTAAT GATCAGCCCA CTGACGCGTT GCGCGAGAAG ATTGTGCACC GCCGCTTTAC      6120

AGGCTTCGAC GCCGCTTCGT TCTACCATCG ACACCACCAC GCTGGCACCC AGTTGATCGG      6180

CGCGAGATTT AATCGCCGCG ACAATTTGCG ACGGCGCGTG CAGGGCCAGA CTGGAGGTGG      6240

CAACGCCAAT CAGCAACGAC TGTTTGCCCG CCAGTTGTTG TGCCACGCGG TTGGGAATGT      6300

AATTCAGCTC CGCCATCGCC GCTTCCACTT TTTCCCGCGT TTTCGCAGAA ACGTGGCTGG      6360

CCTGGTTCAC CACGCGGGAA ACGGTCTGAT AAGAGACACC GGCATACTCT GCGACATCGT      6420

ATAACGTTAC TGGTTTCACA TTCACCACCC TGAATTGACT CTCTTCCGGG CGCTATCATG      6480

CCATACCGCG AAAGGTTTTG CGCCATTCGA TGGTGTCCGG GATCTCGACG CTCTCCCTTA      6540

TGCGACTCCT GCATTAGGAA GCAGCCCAGT AGTAGGTTGA GGCCGTTGAG CACCGCCGCC      6600

GCAAGGAATG GTGCATGCAA GGAGATGGCG CCCAACAGTC CCCCGGCCAC GGGGCCTGCC      6660

ACCATACCCA CGCCGAAACA AGCGCTCATG AGCCCGAAGT GGCGAGCCCG ATCTTCCCCA      6720

TCGGTGATGT CGGCGATATA GGCGCCAGCA ACCGCACCTG TGGCGCCGGT GATGCCGGCC      6780

ACGATGCGTC CGGCGTAGA                                                   6799
```

(2) INFORMATION FOR SEQ ID NO:6:

(i) SEQUENCE CHARACTERISTICS:
        (A) LENGTH: 1299 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..1299
        (D) OTHER INFORMATION: /note= "pET-11d-bEDN-FB-E6-His6a
            anti-transferrin receptor
            antibody/eosinophil derived
            neurotoxin fusion protein sequence"

(ix) FEATURE:
        (A) NAME/KEY: misc_feature
        (B) LOCATION: 115..519
        (D) OTHER INFORMATION: /note= "synthetic eosinophil derived
            neurotoxin (EDN) sequence"

(ix) FEATURE:
        (A) NAME/KEY: misc_feature
        (B) LOCATION: 520..558
        (D) OTHER INFORMATION: /note= "Spacer sequence between E6
            single chain antibody and eosinophil derived neurotoxin"

(ix) FEATURE:
        (A) NAME/KEY: misc_feature
        (B) LOCATION: 559..1266
        (D) OTHER INFORMATION: /note= "Variable heavy and light chains
            of E6 single chain antibody (sFv) with
            linker sequence"

(ix) FEATURE:
        (A) NAME/KEY: misc_feature
        (B) LOCATION: 559..879
        (D) OTHER INFORMATION: /note= "E6 Variable light chain (V-L)
            sequence"

(ix) FEATURE:
        (A) NAME/KEY: misc_feature
        (B) LOCATION: 880..921
        (D) OTHER INFORMATION: /note= "Linker sequence between E6
            antibody light and heavy chain"

(ix) FEATURE:
        (A) NAME/KEY: misc_feature
        (B) LOCATION: 922..1266
        (D) OTHER INFORMATION: /note= "E6 Variable heavy chain (V-H)
            sequence"

(ix) FEATURE:
        (A) NAME/KEY: misc_feature
        (B) LOCATION: 1267..1284
        (D) OTHER INFORMATION: /note= "String of 6 His codon tail to
            aid in purification"

(xi) SEQUENCE DESCRIPTION: SEQ ID NO:6:

```
GGATCGAGAT CTCGATCCCG CGAAATTAAT ACGACTCACT ATAGGGGAAT TGTGAGCGGA      60

TAACAATTCC CCTCTAGAAA TAATTTTGTT TAACTTTAAG AAGGAGATAT ACATATGAAA     120

CCGCCGCAGT TCACTTGGGC TCAGTGGTTC GAAACTCAGC ATATCAACAT GACTTCTCAG     180

CAGTGCACTA ACGCTATGCA GGTTATCAAC AACTACCAGC GTCGTTGCAA AAACCAGAAC     240

ACTTTCCTGC TGACTACTTT CGCTAACGTT GTTAACGTTT GCGGTAACCC GAACATGACT     300

TGCCCGTCTA ACAAAACTCG TAAAAACTGC CATCATTCTG GTTCTCAGGT TCCGCTGATC     360

CATTGCAACC TGACTACTCC GTCTCCGCAG AACATCTCTA ACTGCCGTTA CGCTCAGACT     420

CCGGCTAACA TGTTCTACAT CGTTGCTTGC GACAACCGTG ACCAGCGTCG TGACCCGCCG     480

CAGTACCCGG TTGTTCCGGT TCATCTGGAC CGTATCATCG CCAAGAAACT GAACGACGCT     540

CAGGCGCCGA AGAGTGATGA CATCAAGATG ACCCAGTCTC CATCTTCCAT GTATGCATCT     600

CTAGGAGAGA GAGTCACTTT CACTTGCAAG GCGAGTCAGG ACATTAATAA CTATTTATGC     660

TGGTTCCAGC AGAAACTAGG GAAATCTCCT AAGACCCTGA TCTATCGTGC AAACAGACTG     720

GTAGATGGGG TCCCATCAAG GTTCAGTGGC AGTGGATCTG GACAAGATTA TTCTCTCACC     780

ATTAGCAGCT TGGAGTATGA AGATATGGGA ATTTATTATT GTCTACAGTA TGATGAGTTT     840

CCGTACACGT TCGGAGGGGG GACCAAGCTG GAAATAAAAG AGGGTAAATC CTCAGGATCT     900

GGCTCCGAAT CCAAAGAATT CGAGGTTCAG CTCCAGCAGT CTGGGACTGT ACTGGCAAGG     960

CCTGGGGCTT CAGTGAAGAT GTCCTGCAAG GCTTCTGGCT ACACCATTTC CAGCTACTGG    1020

ATGCACTGGA TAAAACAGAG GCCTGGACAG GGTCTGGACT GGATTGTCGC TATTGATCCT    1080

CGAAATAGTG ATACTATTTA CAACCCGCAA TTCAAACACA AGGCCAAACT GACTGCAGTC    1140

ACCTCCACCA GCACTGCCTA CATGGAACTC AACAGCCTGA CAAATGAGGA CTCTGCGGTC    1200

TATTACTGTA CCCCTCTTTA TTACTTTGAC TCCTGGGGCC AAGGCACCAC TCTCACAGTC    1260

TCCTCACATC ACCATCACCA TCACTAATAG GGATCCGGC                           1299
```

(2) INFORMATION FOR SEQ ID NO:7:

(i) SEQUENCE CHARACTERISTICS:
        (A) LENGTH: 159 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: -
        (B) LOCATION: 1..159
        (D) OTHER INFORMATION: /note= "human epidermal growth factor (EGF)"

(xi) SEQUENCE DESCRIPTION: SEQ ID NO:7:

AACTCTGACT CTGAATGCCC GCTGTCTCAT GACGGTTACT GCCTGCATGA CGGTGTTTGC    60

ATGTACATCG AAGCTCTGGA CAAATACGCT TGCAACTGCG TTGTTGGTTA CATCGGTGAA   120

CGTTGCCAGT ACCGTGACCT GAAATGGTGG GAACTGCGT                          159

(2) INFORMATION FOR SEQ ID NO:8:

(i) SEQUENCE CHARACTERISTICS:
       (A) LENGTH: 381 base pairs
       (B) TYPE: nucleic acid
       (C) STRANDEDNESS: single
       (D) TOPOLOGY: linear (ii) MOLECULE TYPE: DNA (ix) FEATURE:
       (A) NAME/KEY: -
       (B) LOCATION: 1..381
       (D) OTHER INFORMATION: /note= "human ribonuclease (RNase)"

(xi) SEQUENCE DESCRIPTION: SEQ ID NO:8:

AAAGAATCTC GTGCTAAAAA ATTCCAGCGT CAGCATATGG ACTCTGACTC TTCTCCGTCT    60

TCTTCTTCTA CTTACTGCAA CCAGATGATG CGTCGTCGTA ACATGACTCA GGGTCGTTGC   120

AAACCGGTTA ACACTTTCGT TCATGAACCG CTGGTTGACG TTCAGAACGT TGCTTCCAG   180

GAAAAAGTTA CTTGCAAAAA CGGTCAGGGT AACTGCTACA AATCTAACTC TTCTATGCAT   240

ATCACTGACT GCCGTCTGAC TAACGGTTCT CGTTACCCGA ACTGCGCTTA CCGTACTTCT   300

CCGAAAGAAC GTCATATCAT CGTTGCTTGC GAAGGTTCTC CGTACGTTCC GGTTCATTTC   360

GACGCTTCTG TTGAAGACTC T                                             381

(2) INFORMATION FOR SEQ ID NO:9:

(i) SEQUENCE CHARACTERISTICS:
       (A) LENGTH: 540 base pairs
       (B) TYPE: nucleic acid
       (C) STRANDEDNESS: single
       (D) TOPOLOGY: linear (ii) MOLECULE TYPE: DNA (ix) FEATURE:
       (A) NAME/KEY: -
       (B) LOCATION: 1..540
       (D) OTHER INFORMATION: /note= "human RNase-EGF fusion protein
           sequence"

(xi) SEQUENCE DESCRIPTION: SEQ ID NO:9:

AAAGAATCTC GTGCTAAAAA ATTCCAGCGT CAGCATATGG ACTCTGACTC TTCTCCGTCT    60

TCTTCTTCTA CTTACTGCAA CCAGATGATG CGTCGTCGTA ACATGACTCA GGGTCGTTGC   120

AAACCGGTTA ACACTTTCGT TCATGAACCG CTGGTTGACG TTCAGAACGT TGCTTCCAG   180

GAAAAAGTTA CTTGCAAAAA CGGTCAGGGT AACTGCTACA AATCTAACTC TTCTATGCAT   240

ATCACTGACT GCCGTCTGAC TAACGGTTCT CGTTACCCGA ACTGCGCTTA CCGTACTTCT   300

CCGAAAGAAC GTCATATCAT CGTTGCTTGC GAAGGTTCTC CGTACGTTCC GGTTCATTTC   360

GACGCTTCTG TTGAAGACTC GAATTCTGAC TCTGAATGCC CGCTGTCTCA TGACGGTTAC   420

TGCCTGCATG ACGGTGTTTG CATGTACATC GAAGCTCTGG ACAAATACGC TTGCAACTGC   480

GTTGTTGGTT ACATCGGTGA ACGTTGCCAG TACCGTGACC TGAAATGGTG GGAACTGCGT   540

(2) INFORMATION FOR SEQ ID NO:10:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

```
GCACCTGAAT TCCAGGATAA CTCC                                              24
```

(2) INFORMATION FOR SEQ ID NO:11:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:11:

```
Ala Pro Glu Phe Gln Asp Asn Ser
1               5
```

(2) INFORMATION FOR SEQ ID NO:12:

(i) SEQUENCE CHARACTERISTICS:
        (A) LENGTH: 111 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..111
        (D) OTHER INFORMATION: /note= "Frog Lectin from Rana
            catesbeiana"

(xi) SEQUENCE DESCRIPTION: SEQ ID NO:12:

```
Glu Asn Trp Ala Thr Phe Gln Gln Lys His Ile Ile Asn Thr Pro Ile
1               5                   10                  15

Ile Asn Cys Asn Thr Ile Met Asp Asn Asn Ile Tyr Ile Val Gly Gly
                20                  25                  30

Gln Cys Lys Arg Val Asn Thr Phe Ile Ile Ser Ser Ala Thr Thr Val
            35                  40                  45

Lys Ala Ile Cys Thr Gly Val Ile Asn Met Asn Val Leu Ser Thr Thr
        50                  55                  60

Arg Phe Gln Leu Asn Thr Cys Thr Arg Thr Ser Ile Thr Pro Arg Pro
65                  70                  75                  80

Cys Pro Tyr Ser Ser Arg Thr Glu Thr Asn Tyr Ile Cys Val Lys Cys
                85                  90                  95

Glu Asn Gln Tyr Pro Val His Phe Ala Gly Ile Gly Arg Cys Pro
                100                 105                 110
```

(2) INFORMATION FOR SEQ ID NO:13:

(i) SEQUENCE CHARACTERISTICS:
        (A) LENGTH: 104 amino acids
        (B) TYPE: amino acid
        (C) STRANDEDNESS:
        (D) TOPOLOGY: linear (ii) MOLECULE TYPE: protein

```
        (ix) FEATURE:
              (A) NAME/KEY: Protein
              (B) LOCATION: 1..104
              (D) OTHER INFORMATION: /label= Onc
                  /note= "Onconase from Rana pipiens"

(xi) SEQUENCE DESCRIPTION: SEQ ID NO:13:

Glu Asp Trp Leu Thr Phe Gln Lys Lys His Ile Thr Asn Thr Arg Asp
1               5                   10                  15

Val Asp Cys Asp Asn Ile Met Ser Thr Asn Leu Phe His Cys Lys Asp
            20                  25                  30

Lys Asn Thr Phe Ile Tyr Ser Arg Pro Glu Pro Val Lys Ala Ile Cys
            35                  40                  45

Lys Gly Ile Ile Ala Ser Lys Asn Val Leu Thr Thr Ser Glu Phe Tyr
50                      55                  60

Leu Ser Asp Cys Asn Val Thr Ser Arg Pro Cys Lys Tyr Lys Leu Lys
65                      70                  75                  80

Lys Ser Thr Asn Lys Phe Cys Val Thr Cys Glu Asn Gln Ala Pro Val
                85                  90                  95

His Phe Val Gly Val Gly Ser Cys
                100

(2) INFORMATION FOR SEQ ID NO:14:

(i) SEQUENCE CHARACTERISTICS:
            (A) LENGTH: 134 amino acids
            (B) TYPE: amino acid
            (C) STRANDEDNESS:
            (D) TOPOLOGY: linear (ii) MOLECULE TYPE: protein (ix) FEATURE:
            (A) NAME/KEY: Protein
            (B) LOCATION: 1..134
            (D) OTHER INFORMATION: /note= "Human eosinophil derived
                neurotoxin (EDN)"

(xi) SEQUENCE DESCRIPTION: SEQ ID NO:14:

Lys Pro Pro Gln Phe Thr Trp Ala Gln Trp Phe Glu Thr Gln His Ile
1               5                   10                  15

Asn Met Thr Ser Gln Gln Cys Thr Asn Ala Met Gln Val Ile Asn Asn
            20                  25                  30

Tyr Gln Arg Arg Cys Lys Asn Gln Asn Thr Phe Leu Leu Thr Thr Phe
            35                  40                  45

Ala Asn Val Val Asn Val Cys Gly Asn Pro Asn Met Thr Cys Pro Ser
50                      55                  60

Asn Lys Thr Arg Lys Asn Cys His His Ser Gly Ser Gln Val Pro Leu
65                      70                  75                  80

Ile His Cys Asn Leu Thr Thr Pro Ser Pro Gln Asn Ile Ser Asn Cys
                85                  90                  95

Arg Tyr Ala Gln Thr Pro Ala Asn Met Phe Tyr Ile Val Ala Cys Asp
            100                 105                 110

Asn Arg Asp Gln Arg Arg Asp Pro Pro Gln Tyr Pro Val Val Pro Val
            115                 120                 125

His Leu Asp Arg Ile Ile
            130

(2) INFORMATION FOR SEQ ID NO:15:

(i) SEQUENCE CHARACTERISTICS:
```

(A) LENGTH: 133 amino acids
    (B) TYPE: amino acid
    (C) STRANDEDNESS:
    (D) TOPOLOGY: linear (ii) MOLECULE TYPE: protein (ix) FEATURE:
    (A) NAME/KEY: Protein
    (B) LOCATION: 1..133
    (D) OTHER INFORMATION: /note= "Human eosinophil cationic
        protein (ECP)"

(xi) SEQUENCE DESCRIPTION: SEQ ID NO:15:

Arg Pro Pro Gln Phe Thr Arg Ala Gln Trp Phe Ala Ile Gln His Ile
1               5                   10                  15

Ser Leu Asn Pro Pro Arg Cys Thr Ile Ala Met Arg Ala Ile Asn Asn
            20                  25                  30

Tyr Arg Trp Arg Cys Lys Asn Gln Asn Thr Phe Leu Arg Thr Thr Phe
        35                  40                  45

Ala Asn Val Val Asn Val Cys Gly Asn Gln Ser Ile Arg Cys Pro His
    50                  55                  60

Asn Arg Thr Leu Asn Asn Cys His Arg Ser Arg Phe Arg Val Pro Leu
65                  70                  75                  80

Leu His Cys Asp Leu Ile Asn Pro Gly Ala Gln Asn Ile Ser Asn Cys
                85                  90                  95

Arg Tyr Ala Asp Arg Pro Gly Arg Arg Phe Tyr Val Val Ala Cys Asp
            100                 105                 110

Asn Arg Asp Pro Arg Asp Ser Pro Arg Tyr Pro Val Val Pro Val His
        115                 120                 125

Leu Asp Thr Thr Ile
    130

(2) INFORMATION FOR SEQ ID NO:16:

(i) SEQUENCE CHARACTERISTICS:
        (A) LENGTH: 125 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..125
        (D) OTHER INFORMATION: /note= "Bovine angiogenin (Ang)"

(xi) SEQUENCE DESCRIPTION: SEQ ID NO:16:

Ala Gln Asp Asp Tyr Arg Tyr Ile His Phe Leu Thr Gln His Tyr Asp
1               5                   10                  15

Ala Lys Pro Lys Gly Arg Asn Asp Glu Tyr Cys Phe His Met Met Lys
            20                  25                  30

Asn Arg Arg Leu Thr Arg Pro Cys Lys Asp Arg Asn Thr Phe Ile His
        35                  40                  45

Gly Asn Lys Asn Asp Ile Lys Ala Ile Cys Glu Asp Arg Asn Gly Gln
    50                  55                  60

Pro Tyr Arg Gly Asp Leu Arg Ile Ser Lys Ser Glu Phe Gln Ile Thr
65                  70                  75                  80

Ile Cys Lys His Lys Gly Gly Ser Ser Arg Pro Pro Cys Arg Tyr Gly
                85                  90                  95

Ala Thr Glu Asp Ser Arg Val Ile Val Val Gly Cys Glu Asn Gly Leu
            100                 105                 110

Pro Val His Phe Asp Glu Ser Phe Ile Thr Pro Arg His
            115                 120                 125

(2) INFORMATION FOR SEQ ID NO:17:

(i) SEQUENCE CHARACTERISTICS:
        (A) LENGTH: 124 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..124
        (D) OTHER INFORMATION: /note= "Bovine seminal RNase"

(xi) SEQUENCE DESCRIPTION: SEQ ID NO:17:

Lys Glu Ser Ala Ala Ala Lys Phe Glu Arg Gln His Met Asp Ser Gly
1               5                   10                  15

Asn Ser Pro Ser Ser Ser Ser Asn Tyr Cys Asn Leu Met Met Cys Cys
            20                  25                  30

Arg Lys Met Thr Gln Gly Lys Cys Lys Pro Val Asn Thr Phe Val His
        35                  40                  45

Glu Ser Leu Ala Asp Val Lys Ala Val Cys Ser Gln Lys Lys Val Thr
50                  55                  60

Cys Lys Asn Gly Gln Thr Asn Cys Tyr Gln Ser Lys Ser Thr Met Arg
65                  70                  75                  80

Ile Thr Asp Cys Arg Glu Thr Gly Ser Ser Lys Tyr Pro Asn Cys Ala
            85                  90                  95

Tyr Lys Thr Thr Gln Val Glu Lys His Ile Ile Val Ala Cys Gly Gly
        100                 105                 110

Lys Pro Ser Val Pro Val His Phe Asp Ala Ser Val
        115                 120

(2) INFORMATION FOR SEQ ID NO:18:

(i) SEQUENCE CHARACTERISTICS:
        (A) LENGTH: 124 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: Protein
        (B) LOCATION: 1..124
        (D) OTHER INFORMATION: /note= "Bovine pancreatic RNase A"

(xi) SEQUENCE DESCRIPTION: SEQ ID NO:18:

Lys Glu Thr Ala Ala Ala Lys Phe Glu Arg Gln His Met Asp Ser Ser
1               5                   10                  15

Thr Ser Ala Ala Ser Ser Ser Asn Tyr Cys Asn Gln Met Met Lys Ser
            20                  25                  30

Arg Asn Leu Thr Lys Asp Arg Cys Lys Pro Val Asn Thr Phe Val His
        35                  40                  45

Glu Ser Leu Ala Asp Val Gln Ala Val Cys Ser Gln Lys Asn Val Ala
50                  55                  60

Cys Lys Asn Gly Gln Thr Asn Cys Tyr Gln Ser Tyr Ser Thr Met Ser
65                  70                  75                  80

Ile Thr Asp Cys Arg Glu Thr Gly Ser Ser Lys Tyr Pro Asn Cys Ala

-continued

```
                85                  90                  95

Tyr Lys Thr Thr Gln Ala Asn Lys His Ile Ile Val Ala Cys Glu Gly
            100                 105                 110

Asn Pro Val Val Pro Val His Phe Asp Ala Ser Val
        115                 120

(2) INFORMATION FOR SEQ ID NO:19:

(i) SEQUENCE CHARACTERISTICS:
          (A) LENGTH: 15 amino acids
          (B) TYPE: amino acid
          (C) STRANDEDNESS:
          (D) TOPOLOGY: linear (ii) MOLECULE TYPE: peptide (xi) SEQUENCE DESCRIPTION: SEQ ID NO:19:

Gly Gly Gly Gly Ser Gly Gly Gly Gly Ser Gly Gly Gly Gly Ser
1               5                   10                  15
```

SELECTIVE RNASE CYTOTOXIC REAGENTS

This is a Division of application Ser. No. 08/125,462 filed Sep. 22, 1993, now U.S. Pat. No. 5,840,840 which is a continuation-in-part application of Ser. No. 08/014,082 filed Feb. 4, 1993 now abandoned which was a continuation of Ser. No. 07/779,195 filed Oct. 22, 1991, now abandoned, which was a continuation-in-part application of Ser. No. 07/510,696 filed on Apr. 20, 1990, now abandoned, all of which are hereby incorporated by reference.

FIELD OF THE INVENTION

The present invention relates to directed cytotoxic reagents, including immunotoxins, that selectively kill cells having a given surface marker and nucleic acid constructs encoding them. These reagents comprise a toxic moiety that is derived from a protein having ribonucleolytic activity linked to a recognition moiety capable of specific binding with a chosen cell. In particular, the present invention relates to such cytotoxic reagents comprising mammalian, preferably human, proteins with ribonucleolytic activity and humanized chimeric antibodies or receptor binding ligands that recognize tumor cells or virus-infected cells.

BACKGROUND OF THE INVENTION

Toxic enzymes from plants and bacteria such as ricin, diphtheria toxin and pseudomonas toxin have been coupled to antibodies or receptor binding ligands to generate cell-type-specific-killing reagents (Youle et al., 1980, *Proc Natl Acad Sci USA* 77:5483–5486; Gilliland et al., 1980, *Proc Natl Acad Sci USA* 77:4539–4543; Krolick et al., 1980, *Proc Natl Acad Sci USA* 77:5419–5423). Notwithstanding the fact that the cell-recognition moiety is not always an antibody, these directed toxins are generally known as immunotoxins (ITs). These hybrid proteins kill tumor cells, for example, which express the receptor that the antibody or ligand portion of the molecule recognizes.

Under appropriate conditions, conferred by the particular receptor system, the toxin enters the cytosol, inactivates the protein synthesis machinery and causes death of the target cell. Immunotoxins are highly cytotoxic to cancer cells growing in cell culture and animal models demonstrate the potential of these reagents to treat blood borne malignancies as well as solid tumors in restricted compartments such as the intraperitoneal cavity (reviewed in Griffin et al., 1988, *Immunotoxins*. Boston/Dordrecht/Lancaster, Kluwer Academic Publishers, p 433; Vitetta et al., 1987, *Science* 238:1098; Fitzgerald et al., 1989, *J. Natl. Cancer Inst.* 81:1455).

The injection of ITs containing plant or bacterial proteins into patients was anticipated to elicit an antibody response that would present a major obstacle to the successful application of this technology. Indeed, immune responses against murine monoclonal antibodies (Sawler et al., 1985, *J. Immunol.* 135:1530–1535; Schroffet et al., 1985, *Cancer Res.* 45:879–885) and anti-toxin antibodies have been detected in both animals and humans treated with ITs (Rybak et al., 1991, *Immunol. and Allergy Clinics of North America* 11:2, 359–380; Harkonen et al., 1987, *Cancer Res.* 47:1377–1385; Hertler, A. (1988) in Immunotoxins (Kluwer Academic Publishers, Boston/Dordrecht/Lancaster,), 475). Although advances in protein design techniques promise to alleviate some of the immunogenicity associated with the antibody portion of ITs (Bird et al., 1988, *Science* 242:423; Huston et al., 1988, *Proc Natl Acad Sci USA* 85:5879; Ward et al., 1989, *Nature* 341:544), no solution has been forthcoming for the immunogenicity of the toxin other than immunosuppression of the patients (Khazaeli et al., 1988, *Proceedings of AACR* 29:418). Thus, there has been a continuing need for methods and compositions that would reduce the immunogenicity of the toxic moiety of cytotoxic reagents that selectively kill cells having a given surface marker.

In that regard a great deal of effort is being directed toward obtaining chimeric (Boulianne et al., 1985, *Nature* 643–646; Morrison et al., 1984, *Proc. Natl. Acad. Sci. USA* 81:6851–6855) or humanized antibodies (Jones et al., 1986, *Nature (London)* 314:522–525) for human therapeutics. Chimeric antibodies combine the variable region binding domain of a murine antibody with human antibody constant regions. "Humanized" antibodies contain only murine complementarity-determining regions combined with human variable region frameworks and human constant regions.

Human transferrin (Tfn) is a serum glycoprotein that binds and delivers iron to cells by receptor mediated endocytosis reviewed in Youle et al., 1987, *Immunoconjugates: Antibody Conjugates in Radioimaging and Therapy of Cancer*. Oxford, Oxford University Press. After relinquishing its iron, apo-Tfn-receptor recycles to the cell surface where apo-Tfn is released to continue the cycle. Monoclonal antibodies originally isolated based upon selectivity for tumor cells have been found to react with the human transferrin receptor. Transferrin (Raso et al., 1984, *J Biol Chem.* 259:1143–1149; O'Keefe et al., 1985, *J Biol Chem.* 260:932–937.) Or antibodies to the Tfn-receptor (Pirker et al., 1985, *Cancer Res.* 45:751–757; FitzGerald et al., 1983, *Proc Natl Acad Sci USA* 80:4134; Scott et al., 1987, *J Natl Cancer Inst.* 79(5):1163–1172; Trowbridge et al., 1981, *Nature* 294:171–173) linked to toxic proteins have resulted in highly cytotoxic conjugates specifically toxic to cancer cells in vitro and in vitro (Marks et al., 1990, *Cancer Res.* 50:288–292.; Scott et al., 1987, *J Natl Cancer Inst.* 79(5):1163–1172; FitzGerald et al., 1987, *Cancer Res.* 47:111407–1410).

Toxic ribosome inactivating proteins from plants inactivate protein synthesis by enzymatically cleaving a single N-glycosidic bond of the 28S ribosomal RNA (Endo et al., 1987, *J Biol Chem.* 262:8128–8130). Other cytotoxic proteins that inactivate ribosomes include α-sarcin, which is produced by a fungus (Endo et al., 1982, *J Biol Chem.* 257:9054–9060; Endo et al., 1983, *J Biol Chem.* 258:2662–2667.) and cloacin DF13, a plasmid encoded bacteriocin (DeGraaf et al., 1977, *Eur J. Biochem.* 73:107–114) both of which have ribonuclease (RNase) activity.

Analogous toxic mammalian proteins have not been described, but some members of the ribonuclease superfamily in mammals have interesting, possibly related, biological properties. Studies have demonstrated the cytotoxic properties of the ribonuclease superfamily. The bacterial cytotoxins colicin E3 and colicin Df13 target ribosomal RNA (Konishi, J., 1982, *Rev Microbiol* 36:125–144) and recently a bacterial RNase has been fused to the gene for pseudomonas exotoxin A to create a new chimeric toxin (Prior et al., 1991, *Cell* 64:1017–1023). The fungal toxin (α-sarcin expresses RNase activity (Endo, T. & Wool, I., 1982, *J. Biol. Chem.* 257:9054–9060; Endo et al., 1983, *J. Biol. Chem.* 258:2662–2667) and in plants normal pollen function in Nicotiana alata is aborted by RNase activity on pollen tube ribosomal RNA (McClure et al., 1990, *Nature* 347:757–760). The cytotoxicity of RNase A towards tumor cells is well documented from studies performed in the 1960s and 1970s and reviewed in (Roth, J., 1963, *Cancer Res.* 23:657–666). The relevance of these early studies is underscored by a recent discovery that the anti-tumor protein from oocytes of Rana pipiens has homology to RNase A (Ardelt et al., 1991, *J. Biol. Chem.* 256:245–251). Furthermore, human serum contains several RNases (Reddi, E., 1975, *Biochem. Biophys. Res. Commun* 67:110–118, Blank et al., Human body fluid ribonucleases: detection, interrelationships and significance 1-203-209 (IRL Press, London, 1981)) that are expressed in a tissue specific manner. The function of these extracellular RNases are not known but the discovery that proteins involved in the host defense activity of the eosinophil are homologous to RNases and express RNase activity (Gleich et al., 1986, *Proc. Natl. Acad. Sci., USA* 83:3146–3150; Slifman et al., 1986, *J. Immunol,* 137:2913–2917) suggests the intriguing possibility that human serum RNases also may have host defense activities.

The human serum ribonuclease angiogenin (Ang) is a human protein with homology to pancreatic RNase (Fett et al., 1985, *Biochemistry* 24:5480–5485) and RNase activity albeit different than that of the pancreatic enzyme (Rybak et al., 1988, *Biochemistry* 27:2288–2294; Shapiro et al., 1986, *Biochemistry* 25:3527–3531). While the active site residues are conserved between Ang and pancreatic RNase, Ang has very little activity toward standard substrates for the pancreatic enzyme (Shapiro et al., 1986, *Biochemistry* 25:3527–3531).

Studies on in vitro protein synthesis demonstrated that angiogenin inhibited the translational capacity of the rabbit reticulocyte lysate (St. Clair et al., 1987, *Proc., Natl. Acad. Sci. USA* 84, 8330–8334). Although it was shown that a ribonucleolytic activity of Ang was responsible for this inhibition, no cleavage of ribosomal RNAs could be demonstrated at concentrations of the enzyme that completely inhibited protein synthesis. This was markedly different from pancreatic RNase that inhibited protein synthesis by degrading the major ribosomal and lysate RNAS. These results coupled with the observation that the base cleavage specificity of Ang and pancreatic RNase were the same toward 5S ribosomal RNAs (Rybak et al., 1988, *Biochemistry* 25:3527–3531) suggested that the ill vivo substrate for Ang was a unique RNA molecule.

Ang is also a potent inhibitor of protein synthesis in cell free extracts (St. Clair et al., 1987, *Proc. Natl. Acad. Sci. USA* 84,8330–8334) and when directly injected into Xenopus oocytes. Bacterially derived recombinant Ang was injected into Xenopus oocytes and also shown to inhibit protein synthesis without degradation of oocyte ribosomal RNA. Indeed further studies identified tRNA as the intracellular substrate degraded by Ang to inhibit protein synthesis. In a living cell, Ang was as toxic as a fungal toxin (α-sarcin) currently being used as the toxic moiety in an immunotoxin construct (Wawrzynczak et al., Cytotoxic and Pharmacokinetic Properties of an Immunotoxin made with the ribosome-inactivating Protein Alpha Sarcin from *Aspergillus giganteus* (Lake Buena Vista, Fla., 1990)). Ang is not cytotoxic toward a wide variety of cultured cells and is normally present in human plasma (Shapiro et al., 1987, *Biochemistry* 26:5141–5146).

Cytotoxic eosinophil granule proteins also have been reported to have RNase activity (Slifman et al., 1986, *J. Immunol.* 137(9):2913–2917; Gullberg et al., 1986, *Biophys Biochem Res Comm.* 139(3):1239–1242), and the sequence of human eosinophil-derived neurotoxin (EDN) is identical to that of the nonsecretory ribonuclease from human urine (Beintema et al., 1988, *Biochemistry* 27:4530–38). The present inventors have found that eosinophil proteins are also potent inhibitors of cell-free protein synthesis. In addition, antitumor (Vescia et al., 1980, *Cancer Res.* 40:3740–3744; Matousek, J., 1973, *Experientia* 29:858–859) and antispermatogenic action (Dostal et al., 1973, *J. Reprod., Fert.* 34:197–200) have been reported for bovine seminal ribonuclease.

SUMMARY OF THE INVENTION

The present invention stems from research of the inventors aimed at identifying RNase proteins with potential for use as toxic moieties in cytotoxic reagents that selectively kill cells.

Thus, it is an object of the present invention to provide cytotoxic RNase reagents that selectively kill cells having a given surface marker, comprising a toxic moiety that is an RNase protein which is, preferably, endogenous to the species in which the reagent is intended for use or is otherwise minimally immunogenic.

Further, it is an object of this invention to provide toxic moieties with less systemic toxicity than presently known toxins used in directed cytotoxic reagents. In particular, it is an object of the present invention to provide direct cytotoxic reagents comprising proteins with ribonucleolytic activity linked to chimeric antibodies that recognize specific markers on tumor cells or virus-infected cells.

Various other objects and advantages of the present invention will be apparent from the following drawings and description of the invention.

In another embodiment, the present invention relates a pharmaceutical composition comprising a cytotoxic reagent of the present invention and a pharmaceutical acceptable carrier.

In a further embodiment, the present invention relates to a method selectively killing cells. The method comprising contacting cells to be killed with a selective cytotoxic reagent of the present invention under conditions such that the recognition moiety binds to a surface marker on the cell thereby causing the toxic moiety to kill the cell.

BRIEF DESCRIPTION OF THE DRAWINGS

The present invention may be understood more readily by reference to the following detailed description of specific embodiments and the Examples and Figures included therein.

FIG. 2. Inhibition of protein synthesis in K562 cells by Tfn-RNase conjugate compared with component proteins. K562 cells ($1 \times 10^5$ cells/ml) were plated into 96 well microtiter plates and treated with varying concentrations of Tfn-RNase (filled circles), RNase (filled squares), or SPDP derivatized RNase (filled triangles). Additional sets of wells contained RNase or SPDP RNase mixed with $1 \times 10^{-6}$M human transferrin (---) Transferrin alone had no effect on protein synthesis. After 24 hours in the presence of additions, the protein synthesis rate was determined by

[$^{14}$C]leucine incorporation. The data points are determined from the mean of triplicate incubations. The SEM was 10% or less. 100%=7×10$^3$ cpm [$^{14}$C]leucine incorporation.

Figure 2:
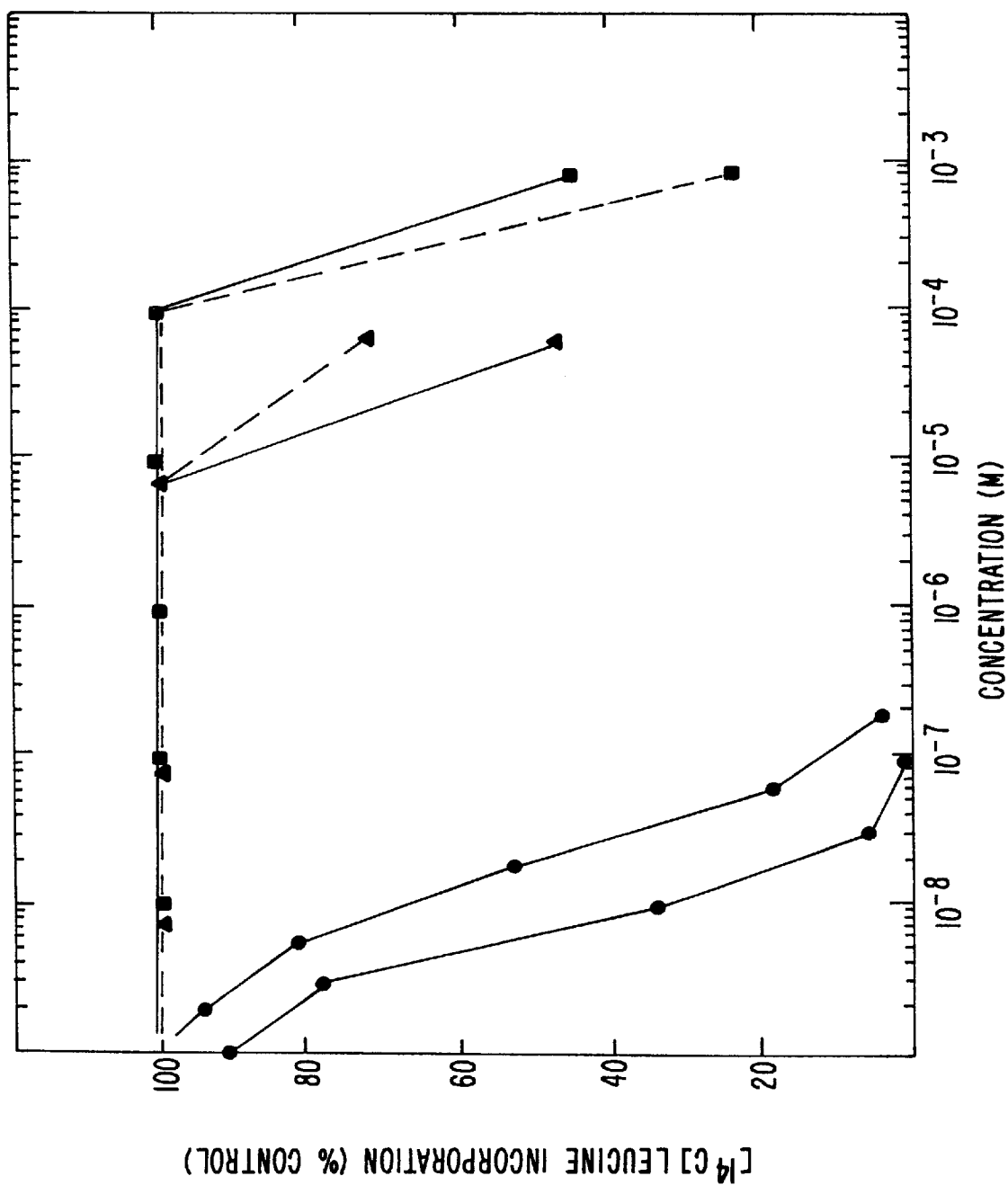
Figure 3:
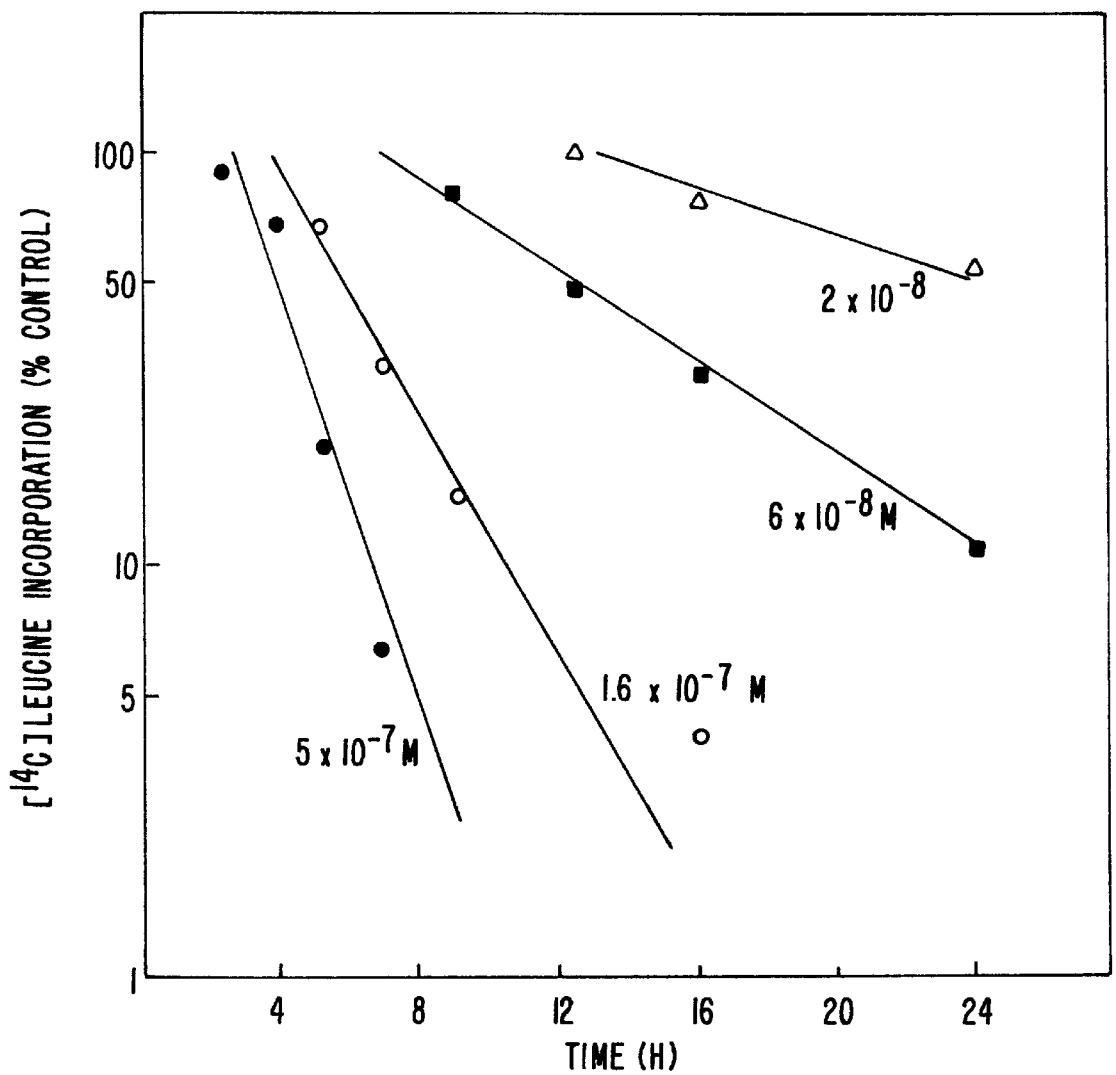

FIG. 3. Time course of protein synthesis inhibition caused by Tfn-RNase in K562 cells. K562 cells (2×10$^5$ cells/ml) were treated as described in the legend to FIG. 2. Different concentrations of Tfn-RNase were added and the cells were processed for [$^{14}$C]leucine incorporation as described. The times indicated include a 1 hour pulse with [$^{14}$C]leucine. The data points were determined as described in the legend to FIG. 2.

Figure 4:
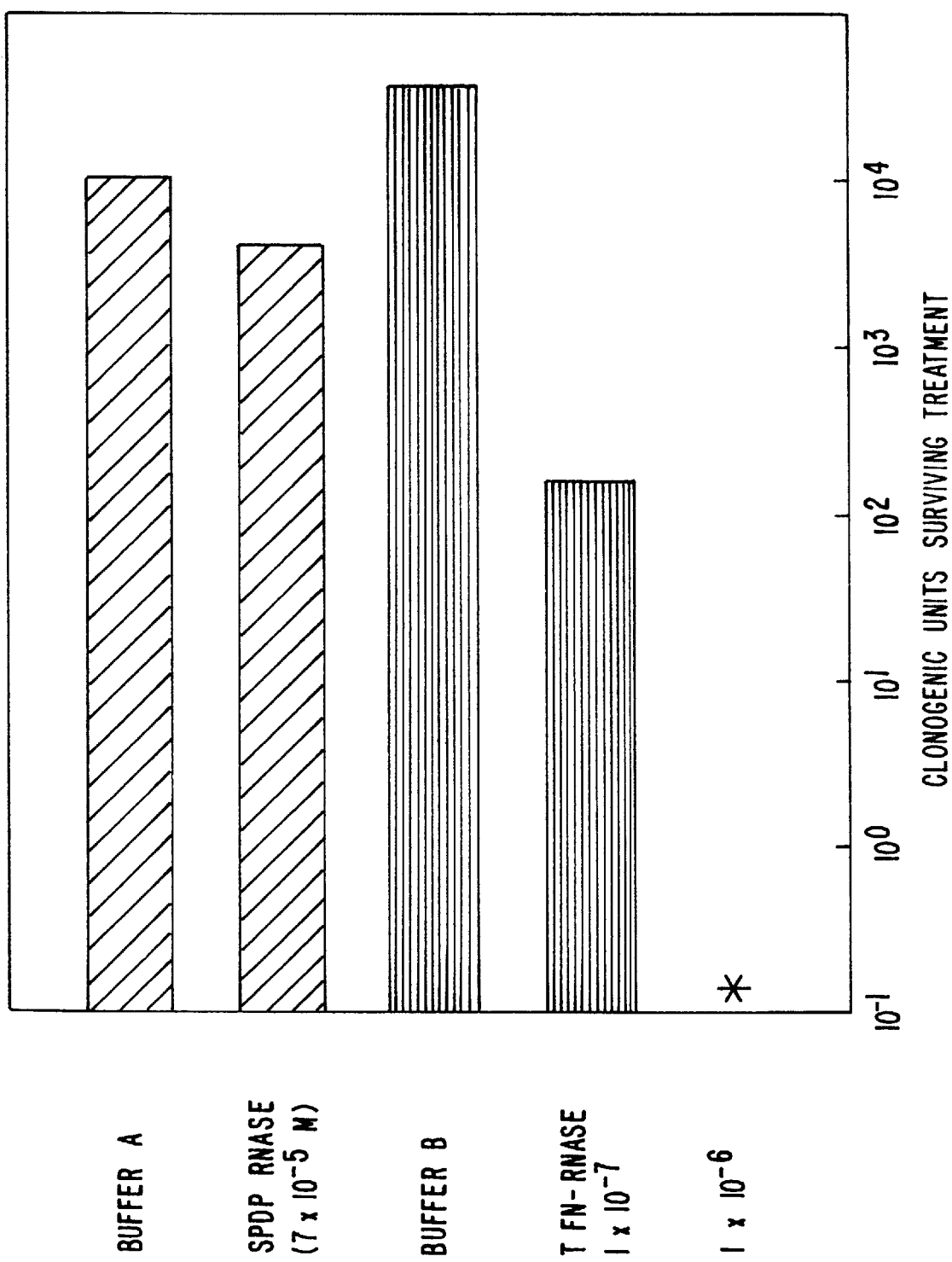

FIG. 4. Clonogenic growth assay of K562 cells treated with Tfn-RNase. K562 cells (1.4×10$^5$ cells/ml) were treated with buffer A, 0.1M NaCl-0.1M NaPO$_4$, pH7.2 or buffer A which contained SPDP-RNase (7×10$^{-5}$M). Another set in the same experiment contained K562 cells treated with buffer B, 0.1M NaPO$_4$, pH7.2 or buffer B containing Tfn-RNase at 10$^{-4}$ or 10$^{-7}$M. After 24 hour treatment the cells were washed, diluted into complete medium and plated into 96 well microtiter plates (10 wells/dilution). After 14 days the fraction of surviving cells was calculated using the Spearmen-Karber estimator (Johnson, E. and B. Brown, 1961, "The Spearman estimator for serial dilution assays." Biometrics 17: 79–88). In this assay a 10 fold difference is considered statistically significant.

Figure 5:
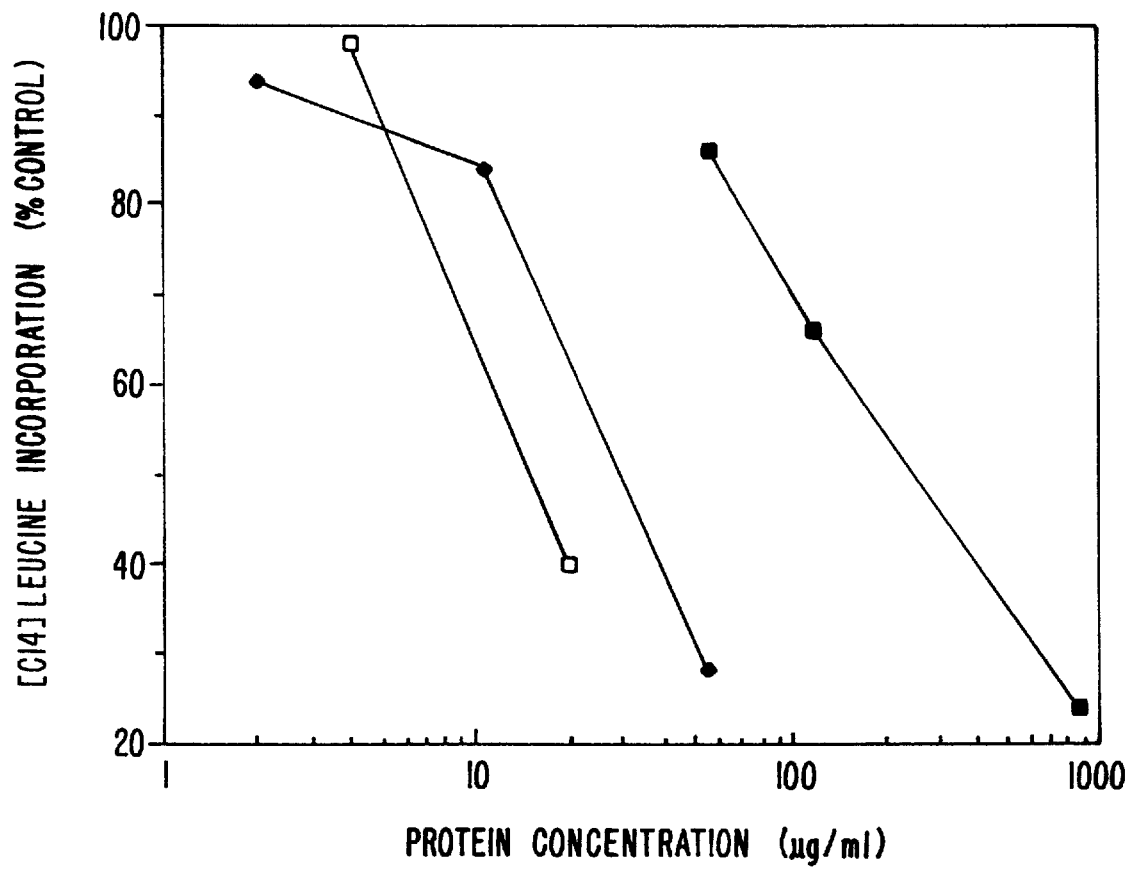

FIG. 5. Inhibition of protein synthesis by a monoclonal antibody against the Tfn receptor coupled to RNase. Cells were incubated as described in FIG. 2 with Fr27, a monoclonal antibody B3-25 against the human transferrin receptor coupled by a disulfide linkage to RNase. Fr28 is a repeat experiment. SPDP-RNase alone was also incubated with K562 cells.

Figure 6:
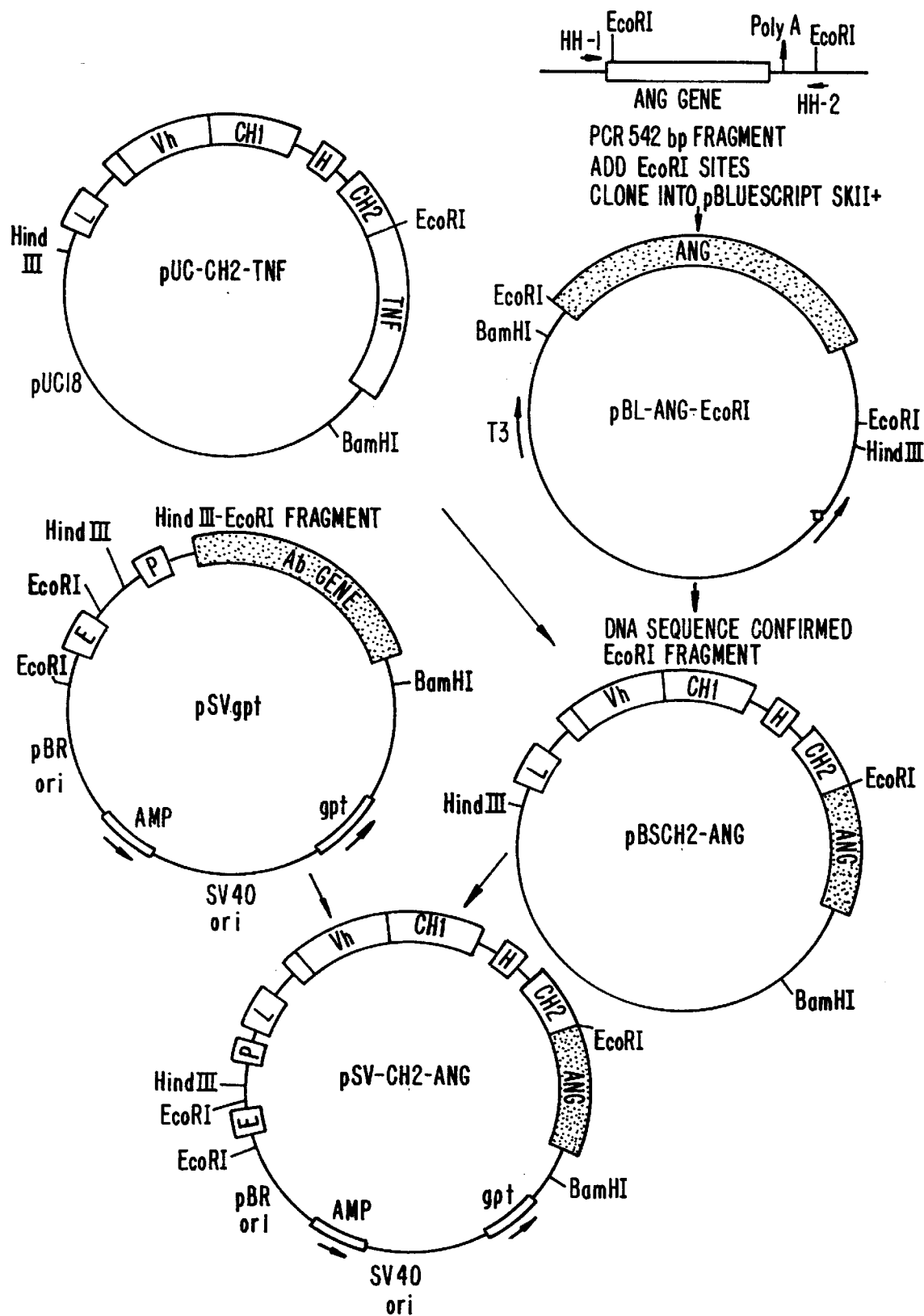

FIG. 6. Outline of the strategy used to construct expression plasmid pSV-CH2-ANG. Only the restriction sites used in the construction are indicated. Detailed structure and construction of pUC-CH2-TNF and expression vector pSVgpt is described in (Hoogenboom, H., Raus, J. & Volckaert, G., 1991, Biochem Biophys Acta 1096:345–354) and (Neuberger, M. 1983, EMBO J 2:1373–1378) respectively. Labeled features ofthe plasmid are: E, enhancer; P, promoter, L, immunoglobulin leader sequence; Vh, mouse variable regions of E6 antibody gene; CH1 & CH2, constant regions 1 and 2 respectively of the heavy chain gene; the hinge region of heavy chain gene; Ang, DNA coding for human angiogenin is shown in a shaded box; gpt, xanthineguanine phosphoribosyltransferase; AMP, ampicillin resistance gene.

FIG. 7. Sequences around the junction between antibody heavy chain in the CH2 domain and the 5' end of the sequence coding for mature Ang in the CH2Ang construct. E and F are amino acids introduced by PCR modification of the Ang gene prior to cloning. Single letter amino acid code is used. (Nucleotide sequence=SEQ ID NO:10; Amino acid sequence=SEQ ID NO:11).

Figure 8:
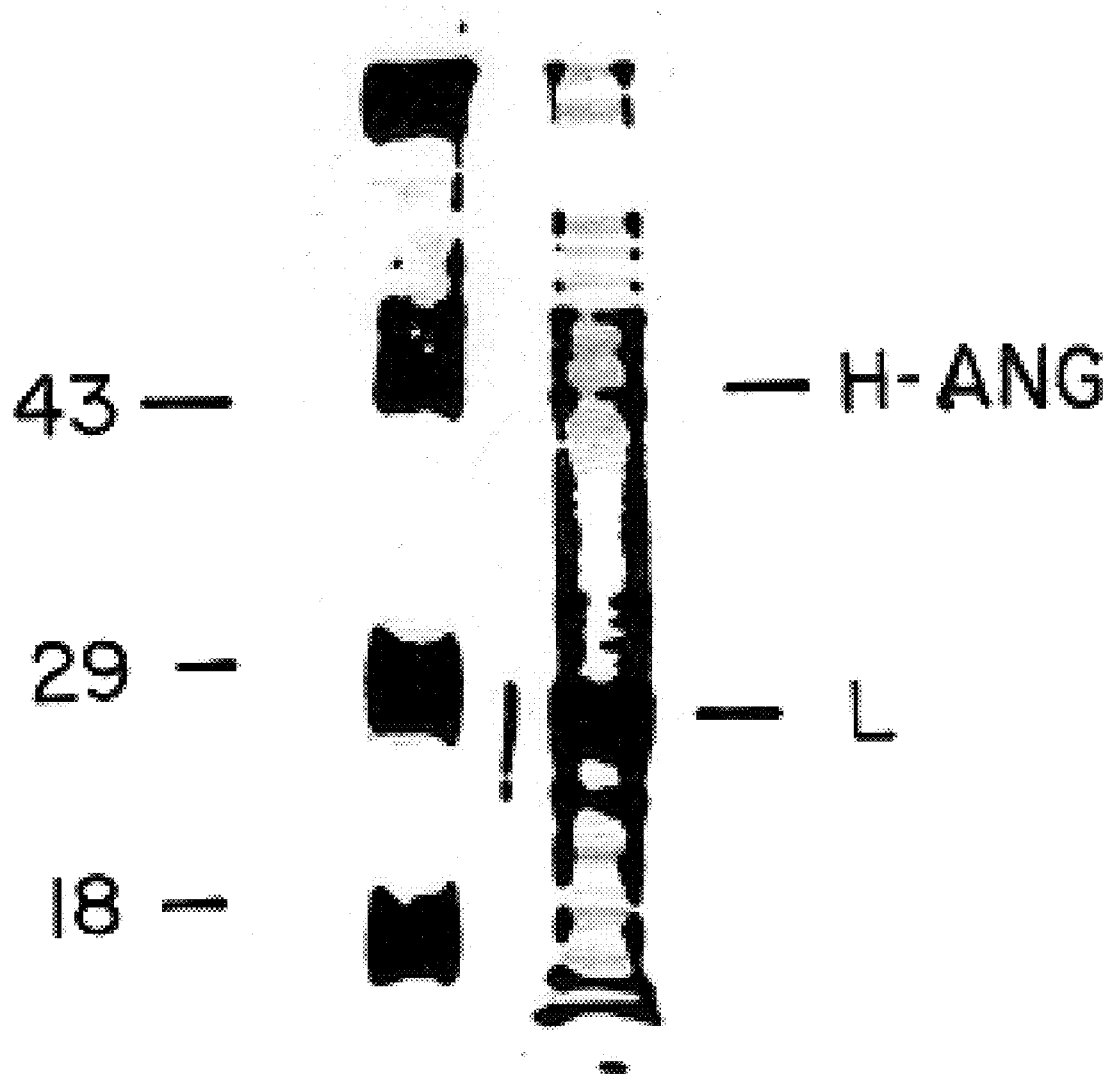

FIG. 8. Immunoprecipitation of [$^{35}$S]-Met labeled proteins from CH2.5Ang culture supernatants. Cells secreting CH2.5Ang were plated into methionine free RPMI containing 0.2% FCS and the additions described in Methods. [$^{35}$S]-Met (50 µCi/ml) was added and the cells were incubated for 18 h at 37° C. and then separated from the culture supernatant. The samples were prepared, electrophoresed and analyzed by fluorography as described herein. The arrows indicate the presence of the heavy and light chains of the chimeric antibody fusion protein. Molecular weight markers are indicated for reference.

FIGS. 9A–9C. CM cellulose fractionation of CH2.5Ang cell culture supernatants. Transfectoma medium was fractionated as described herein. The distribution of protein was followed by optical density of the samples at 280 A (upper) (FIG. 9A) or by following the reactivity of the samples with antibody to human IgG (middle) (FIG. 9B). Starting material (SM); Flow through (FT); 0.1, 0.5 and 1.0M NaCl in the elution buffer. (Bottom) In vitro protein synthesis assay of 0.5M IgG containing pool (middle). The CMC pool containing the highest amount of IgG reactive material was assayed for effects on in in vitro protein synthesis using the rabbit reticulocyte lysate as described herein. Experiment 1 (1) Control medium (C); 0.5M CMC pool containing Ang at a final assay concentration of 40 ng/ml) (A1); 0.5M CMC pool containing Ang at 80 ng/ml (A2); 0.5M CMC pool (80 ng/ml) plus PRI 80 units (A+P); Experiment 2 (2). Control medium (c); 0.5M CMC pool (80 ng/ml) (A); 0.5M CMC pool (80 ng/ml) plus calf tRNA (20 µg/ml) (Att) (FIG. 9C).

Figure 10:
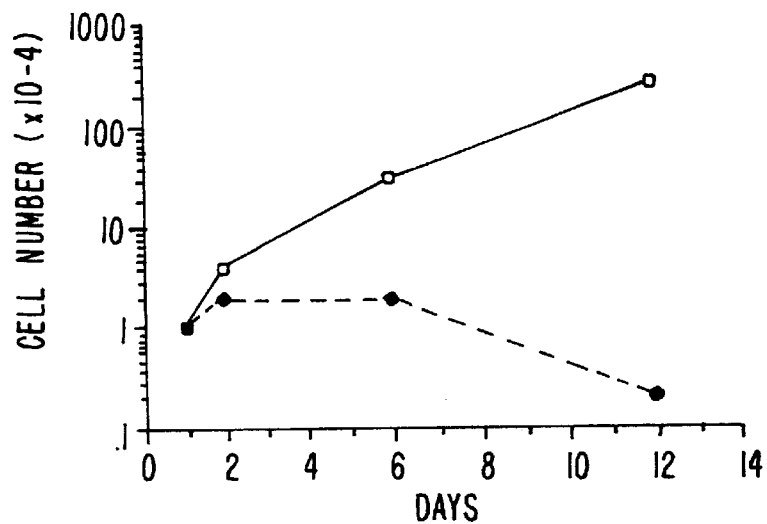

FIG. 10. Growth of K562 cells in CH2.5Ang culture supernatant. K562 cells (10$^4$) were plated into p24 plates in 1 ml of growth medium (--■--) or 1 ml of growth medium that contained 1–2 ng/ml of CH2.5Ang (--♦- -). The cell counts determined as described herein are representative of several experiments.

Figure 11A:
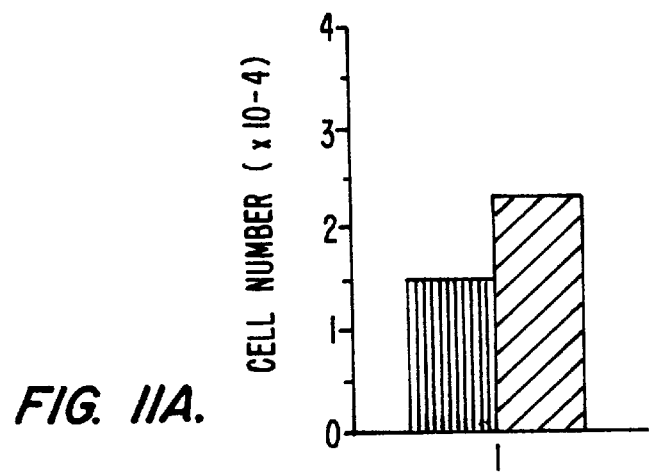
Figure 11B:
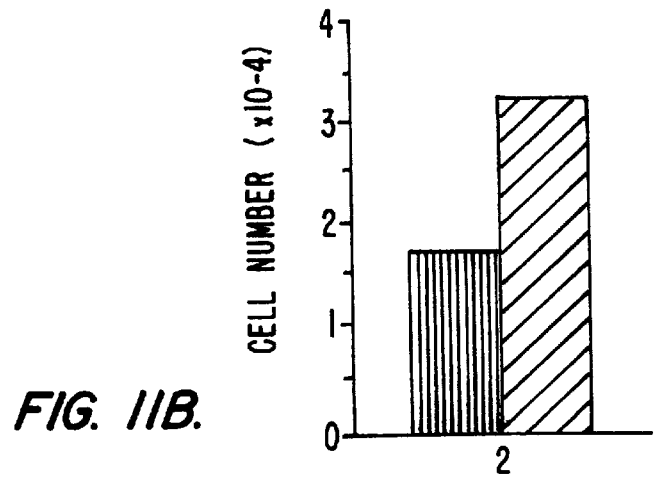

FIGS. 11A–11B. E6 reverse growth inhibitory effects of CH2.5Ang medium. K562 cells were plated as described above without (black vertical bar) or with (diagonal bar) E6 anti-transferrin receptor antibody (4 µg/ml). The cells were counted as described herein after 2 d in culture (1) (FIG. 11A) or 5 d in culture (2) (FIG. 11B).

Figure 12A:
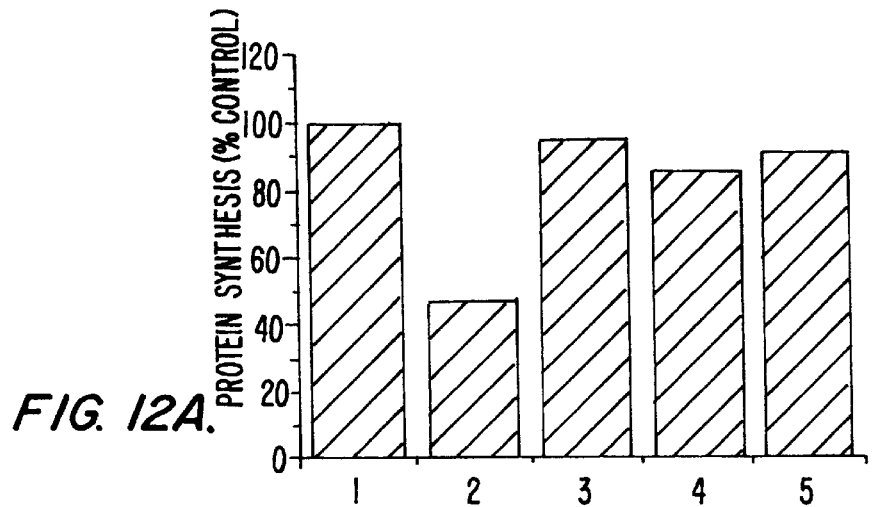
Figure 12B:
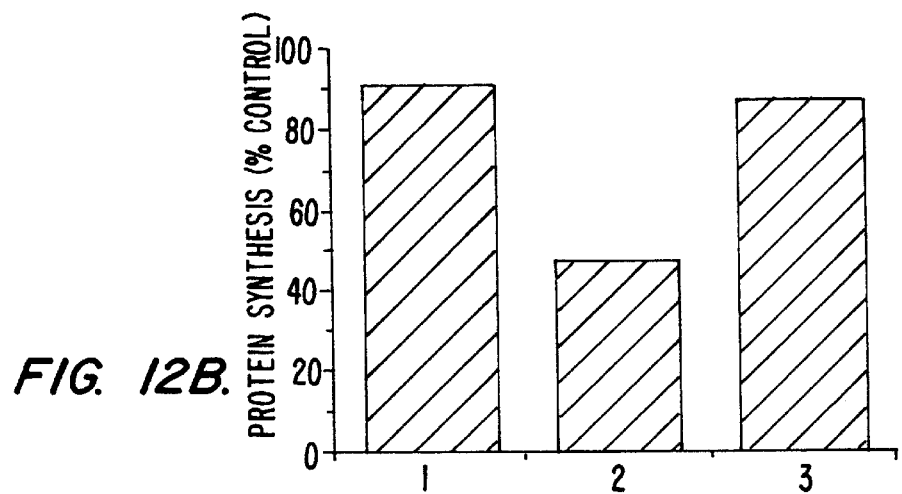
Figure 12C:
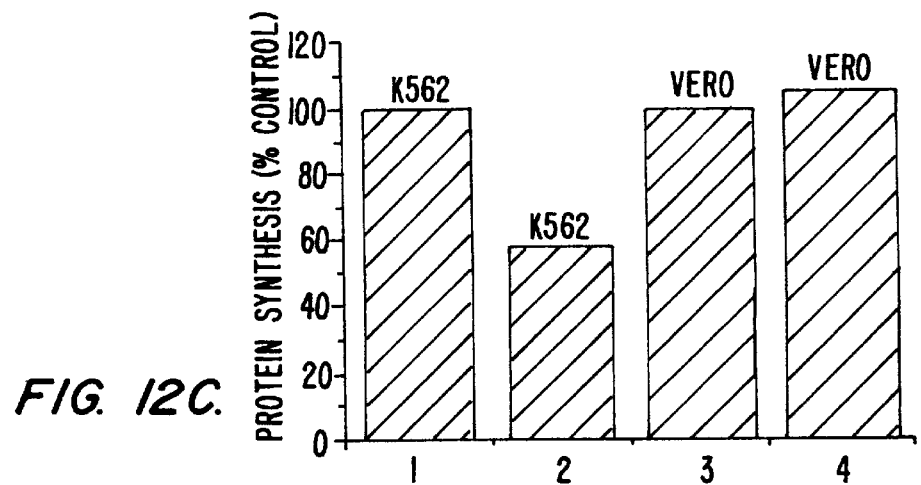

FIGS. 12A–12C. Protein synthesis in K562 cells. (Upper, FIG. 12A) K562 cells were plated with growth medium alone (1); medium containing 1–2 ng/ml CH2.5Ang (2) or growth medium containing Ang protein (1 µg/ml); E6 anti-transferrin receptor antibody (4 µg/ml, 4); or the same amounts of a mixture of Ang and E6 (5). Protein synthesis was measured after 24 h as described herein. (Middle; FIG. 12B) Inhibition of protein synthesis by CH2.5Ang medium is blocked by E6. Protein synthesis was measured in K562 cells as described herein after 24 h with additions. E6 anti-transferrin receptor antibodies added to growth medium (4 µg/ml, 1), CH2.5Ang medium (1–2 ng/ml, 2); CH2.5Ang medium plus E6 (4 µg/ml, 3). (Bottom, FIG. 12C) CH2.5Ang medium does not inhibit protein synthesis in non-target cells. Cells were plated into medium and protein synthesis measured as described herein. Control growth medium (1,3); CH2.5Ang medium (2,4).

Figure 13A:
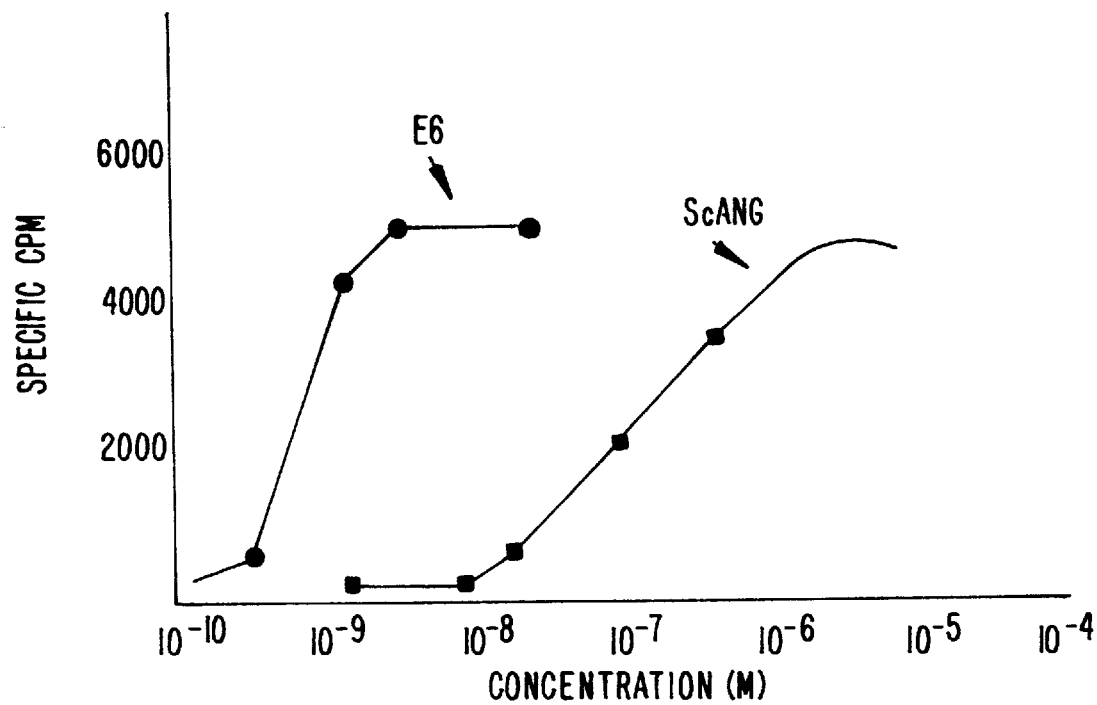
Figure 13B:
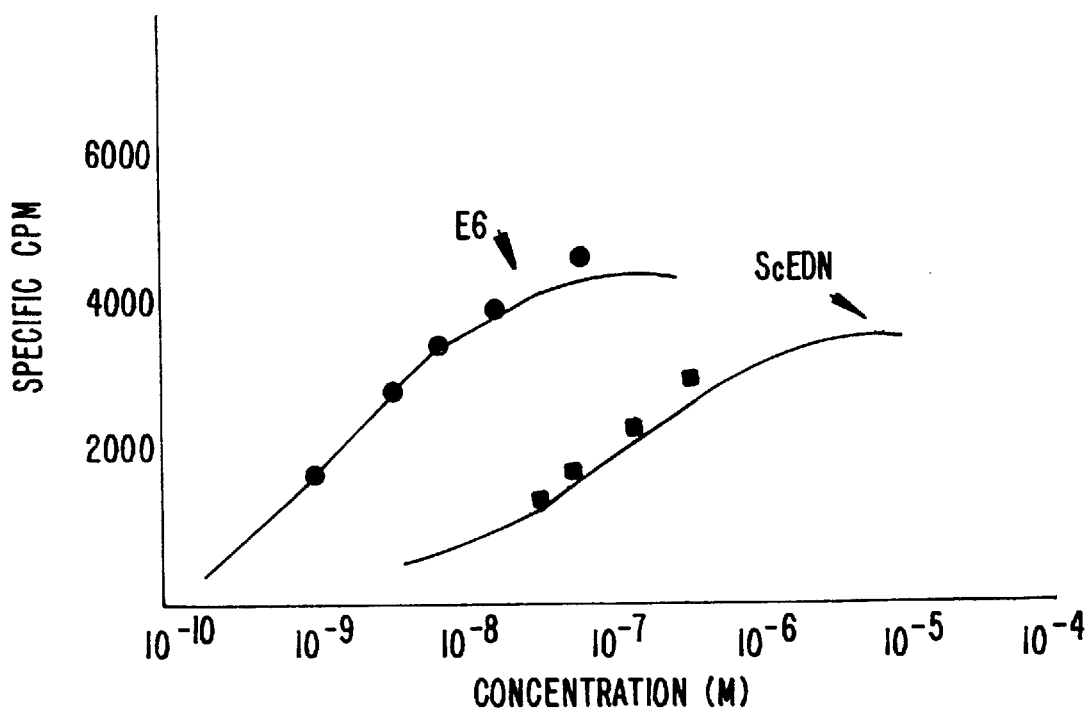

FIGS. 13A and 13B show that the ScANG (pET-11d-ANG-FB-E6-His6) and ScEDN (pET-11d-EDN-FB-E6-His6) bind less well than the native antibody by a magnitude of 1 to 2 logs depending on the particular batch in a standard binding assay with K562 cells. K562 cells (10$^6$ cells per ml) were placed in an Ependorf tube with unlabeled ScEDN or parent E6 antibody and incubated at 4° C. for 30 minutes. Iodinated E6 was added to the cells for an additional 4 hours. The cell pellet was washed four times and then counted.

Figure 14:
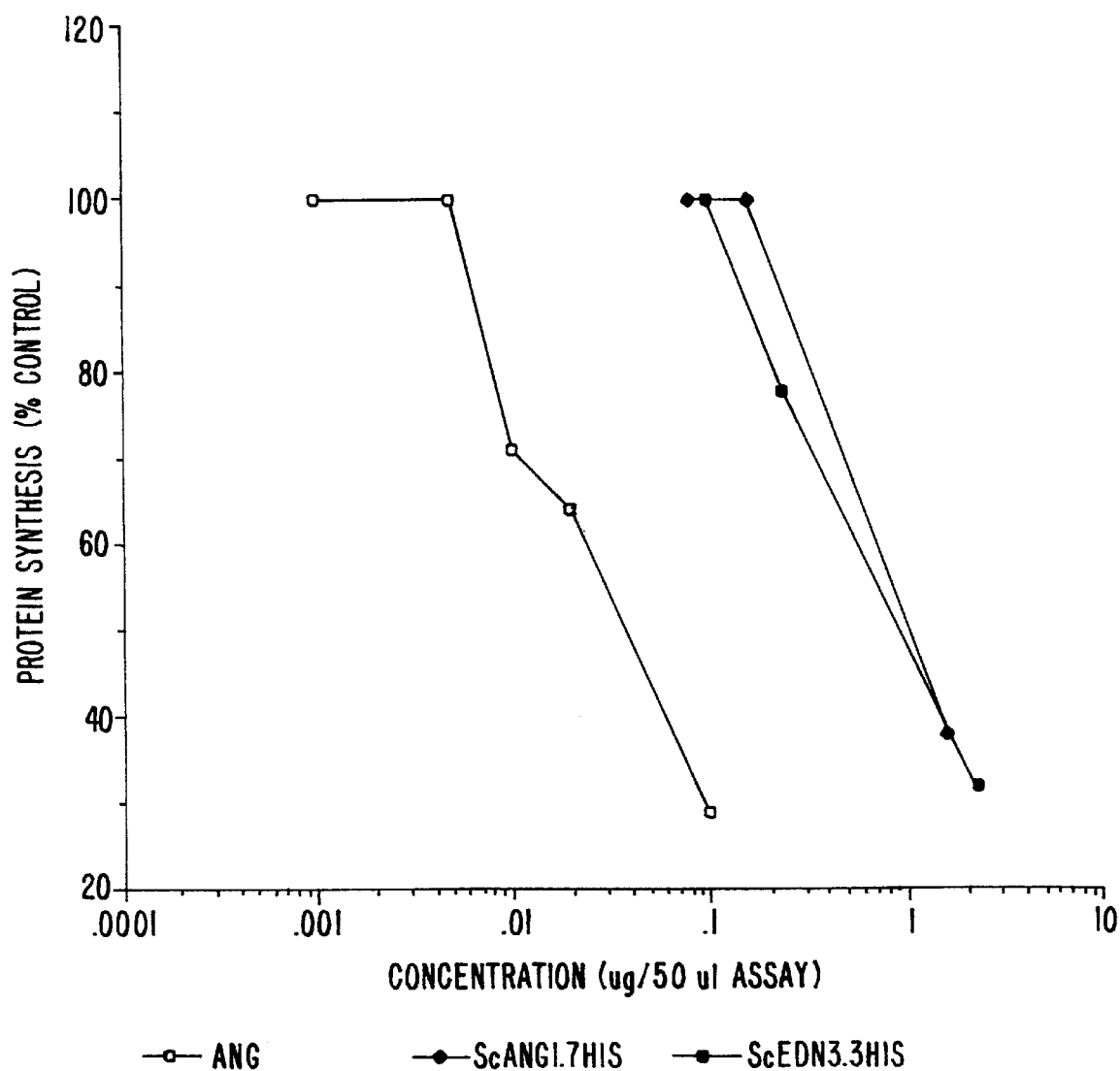

FIG. 14 shows the effect of inhibition of cell-free protein synthesis. Both ScANG and ScEDN are potent inhibitors of cell-free protein synthesis, but less so than the native proteins. The effect of the fusions is compared to ANG alone in FIG. 14. The in vitro translation assay was performed by incubating rabbit reticulocyte lysate with or without additions at the concentration specified for 60 minutes at 30° C. The incubation was in the presence of amino acids and 35S methionine. The amount of protein synthesis was determined by the incorporation of 35S methionine into products precipitable by 10% trichloroacetic acid.

Figure 15:
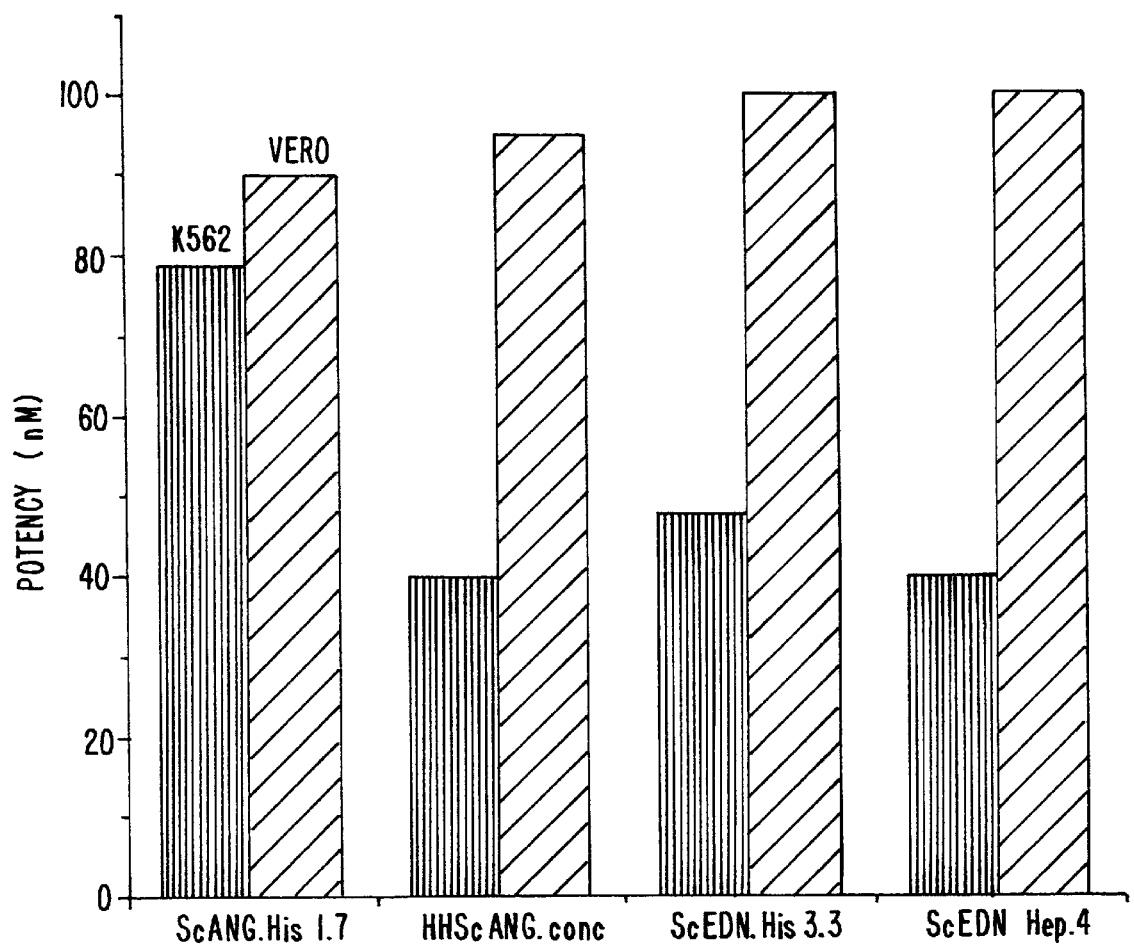

FIG. 15. Neither ANG nor EDN have effects on K562 leukemia cells that express the human transferrin receptor but they inhibit protein synthesis in these cells when attached to an antibody that recognizes the receptor as shown in FIG. 15. Vero cells do not express this receptor and are unaffected by the fusion proteins. ScAng.His1.7 is equivalent to pET-11d-ANG-FB-E6-HIS6. HHScANG.conc is equivalent to pET-11d-ANG-E6. ScEDN.His3.3 is equivalent to pET-11d-EDN-FB-E6-HIS6. ScEDN Hep.4 is equivalent to pET-11d- E6-FB-EDN. The assay was similar to the one described in connection with FIG. 12.

FIG. 16 shows a dose-dependent effect of ScEDN (pET-11d-EDN-FB-E6-HIS6) to inhibit protein synthesis on target K562 human leukemia cells, similar to that described for FIG. 3.

FIG. 17 shows that EDN alone has no effect on protein synthesis of K562 cells but that ScEDN is at least 2 logs more potent.

FIGS. 18A, 18B, and 18C represent three different experiments (A, B and C) and show that ScEDN inhibits protein synthesis in K562 cells which have more receptors than A431 cells and that it does not inhibit protein synthesis in NIH3T3 cells which do not have receptors for the human transferrin receptor.

FIG. 19 shows a sequence alignment of some members of the RNase A superfamily: Frog lectin is from *Rana catesbaiana* (SEQ ID NO:12), onconase (SEQ ID NO:13) EDN (SEQ ID NO:14) ECP (human eosinophil cationic protein (SEQ ID NO:15), ANG is bovine angiogenin (SEQ ID NO:16), seminal is bovine seminal RNase (SEQ ID NO:17), and RNase A is bovine pancreatic RNase A (SEQ ID NO:18). Amino acids conserved in all members are capitalized, and active site residues H12, K41, and H119 (RNase A numbering) are marked with an asterisk.

DESCRIPTION OF THE PREFERRED EMBODIMENT

The present invention relates to the use of an RNase protein (preferably, a mammalian protein) as a toxic moiety in a directed cytotoxin. Cytotoxic reagents of the present invention comprise a protein and recognition moiety capable of specific binding with a chosen cell surface marker. Preferably both moieties are endogenous to the species in which the cytotoxin complex is to be used, thereby minimizing the immunogenicity of the complex and extending the period of useful administration.

This application discloses a new use for RNase. Applicants have shown that RNase is toxic to cells. When it is chemically linked to a receptor-specific ligand, such as transferrin (Tfn), the complex specifically kills target cells bearing the Tfn-receptor. RNases suitable for use in the present invention include, but are not limited to, mammalian, bacterial and fungal ribonucleases. Applicants have further shown that RNase proteins recombinantly fused to a recognition moiety can be expressed and purified. Applicants overcame several difficulties to obtain such fusion proteins and the proteins obtained are surprisingly very sensitive and have high binding specificity for the target cells.

Accordingly, the present invention relates to a selective cytotoxic reagent comprising a toxic moiety that is an RNase, preferably a member of the pancreatic RNase superfamily, recombinantly fused to a recognition moiety that binds a specific cell surface marker. The cytotoxic reagents function by binding to a surface marker on a cell via the recognition moiety thereby allowing the toxic moiety to kill the cell. To minimize the immunogenicity of the complex, preferably the toxic protein in this cytotoxic reagent is endogenous to the species in which the reagent is intended for use.

The RNase cytotoxic reagent has ribonucleolytic activity, for example, bovine ribonuclease A or, most preferably for human applications, human angiogenin.

Preferably the RNase is one in the pancreatic RNase A superfamily. Many of such members are known and include, but are not limited to, frog lectin from *Rana catesbaiana* (Titani et al., *Biochemistry* 26:2189 (1987)); onconase (Rosenberg et al., *Proc. Natl. Acad. Sci. USA* 86:4460 (1989)); eosinophil derived neurotoxin (EDN) (Rosenberg et al., supra); human eosinophil cationic protein (ECP) (Rosenberg et al., *.J. Exp. Med* 170:163 (1989)); angiogenin (ANG) (Fodstad et al., *Cancer Res.* 44:862 (1984)); bovine seminal RNase (Preuss et al., *Nuc. Acids. Res.* 18:1057 (1990)); and bovine pancreatic RNase (Beintama et al., *Prog. Biophys. Mol. Biol.* 51:165 (1988)), references for all such proteins incorporated by reference herein. Amino acid sequence alignment for such RNases is depicted in FIG. 19. Most preferably for this invention, the RNases in the pancreatic RNase A superfamily will be those which have a 25% or greater amino acid sequence identity with those sequences set out on FIG. 23 and which have the same or conservatively replaced active site as those active sites indicated on FIG. 19.

Novel synthetic genes of interest for RNases are included here for EDN (SEQ ID NO:4), and for a human RNase (SEQ ID NO:8). Both of these are advantageous for pharmaceutical use described here because they encode a human protein, but are readily expressed in a bacterial system.

It is known that administration of bovine RNase A to human patients (in the treatment of tick-borne encephalitis, for example; Glukhov, et al., 1976, *Arch. Neurol.* 38:598–603) does not produce any allergic reactions, and this seems to be connected with its weak antigenic activity. Bacterial and fungal RNases are also suitable for use as the toxic moiety.

The recognition moiety of the cytotoxic reagent according to the present invention is preferably a mammalian protein or a modified form thereof. To further reduce immunogenicity, preferably the recognition moiety of the cytotoxic reagent is endogenous to the species in which the reagent is intended for use. In one of the presently preferred embodiments for human application, the recognition moiety is human transferrin or a modified form thereof, which preferentially binds cells with high levels of the transferrin receptor, for example, certain tumor cells. This embodiment is preferred for human applications in compartments where endogenous levels of transferrin are sufficiently low to avoid competitive interference with binding of the reagent to the transferrin receptor. Another preferred recognition moiety is EGF, that binds to a growth factor receptor, which is overexpressed for example, in brain tumors.

The recognition moiety may be an antibody or a modified form thereof (for example, a Fab fragment or a single chain antibody) which binds a specific cell surface marker on the type of cells that are to be killed. To reduce the immunogenicity of the antibody (or modified form thereof), it is desirable to utilize a chimeric antibody wherein one region of the antibody, preferably the constant domain or the heavy chain, is endogenous to the species in which the reagent is intended for use. For example, a preferred recognition moiety for a cytotoxic reagent for use in humans is a "humanized" chimeric antibody directed against a cell receptor. These chimeric antibodies contain murine complementarity-determining regions combined with human variable and constant region frameworks. The use of humanized antibodies, especially with human proteins, should contribute to alleviating some of the problems of immunogenicity that hampered the success of immunotoxins constructed with bacterial or plant toxins. Although the novel construction of these chimeras might involve new antigenic determinants, it is expected that the recombinant molecules will be far less antigenic. Accordingly, in another embodiment exemplified herein, which is preferred for human applications where endogenous levels of transferrin are sufficiently high to cause competitive interference with binding of the reagent to the transferrin receptor, the recognition moiety is an antibody or portion thereof which recognizes the transferrin receptor in such a way that it is not competitively blocked by transferrin.

In reference to the toxic and recognition moieties, a modified form of a protein includes chemically modified forms as well as mutant forms created through genetic engineering. Chemical modifications include, for example, derivitization for the purpose of linking the moieties to each other, either directly or through a linking compound, by methods that are well known in the art of protein chemistry. In the presently preferred embodiment, the means of linking the toxic moiety and the recognition moiety comprises a heterobifunctional coupling reagent which ultimately contributes to formation of an intermolecular disulfide bond between the two moieties. Other types of coupling reagents that are useful in this capacity for the present invention are described, for example, in U.S. Pat. No. 4,545,985, Pseudomonas exotoxin conjugate immunotoxins. Alternatively, the intermolecular disulfide may conveniently be formed between cysteines in each moiety which occur naturally or are inserted by genetic engineering. The means of linking moieties may also use thioether linkages between heterobifunctional crosslinking reagents or specific low pH cleavable crosslinkers or specific protease cleavable linkers or other cleavable or noncleavable chemical linkages. The means of linking moieties of the cytotoxic reagent may also comprise a peptidyl bond formed between moieties which are separately synthesized by standard peptide synthesis chemistry or recombinant means.

Possible chemical modifications of the protein moieties of the present invention also include derivatization with polyethylene glycol (PEG) to extend time of residence in the circulatory system and reduce immunogenicity, according to well known methods (See for examples, Lisi et al., 1982, *Enzyme Therapy Applied Biochem* . 4:19–33; Beauchamp et al., 1982, *Anal. Biochem.* 131:25–33; and Goodson et al., 1990*, Bio/Technology* 8:343–346).

Possible genetic engineering modifications of the proteins of the cytotoxic reagent include combination of the relevant functional domains of each into a single chain multi-functional biosynthetic protein expressed from a single gene derived by recombinant DNA techniques. (See, for example, application WO8809344-A, Recombinant multifunctional protein having an antibody binding site and a sequence for biological activity, ion sequestering or binding to a solid support). Further, recombinant DNA techniques can be used to link together the toxic moiety and the recognition moiety. Accordingly, the cytotoxic reagent can comprise a fused protein beginning at one end with the cytotoxic moiety and ending with the recognition moiety. Mammalian cells have been used to express and secrete hybrid molecules such as antibody-cytokines (Hoogenboom, H., Raus, J. & Volckaert, 1991*, Biochem Biophvs Acta* 1096:345–354; G., Hoogenboom, H., Volckaert, G. & Raus, Jr., 1991, *Mol Immunol* 28:1027–1037) and antibody-enzyme (Casadei et al., 1990, *Proc. Natl. Acad. Sci. USA* 87:2047–2051; Williams et al., 1986, *Gene* 43:319–324).) Recombinant humanized chimeric antibody-human RNase fusion proteins are preferred cytotoxic reagents as the immunogenicity of the reagent in humans is reduced.

Other genetic engineering modifications of the protein moieties of the cytotoxic reagent of this invention include deletions of functionally unnecessary domains to reduce the size of the protein or to modify other parameters which facilitate production or utility, such as sequence changes to affect the solubility (e.g., cysteine to serine) or glycosylation sites. One skilled in the art would appreciate that many additional well known chemical and genetic modifications of proteins may be advantageously applied to any protein which, like the present cytotoxic reagent, is intended for parenteral administration.

Preferred cytotoxic reagents of the present invention are fusion proteins containing as the toxic moiety an RNase derived from a mammalian source (more preferably, human Ang) and a "humanized" chimeric antibody that binds a specific cell surface marker on the cell of interest (more preferably against the transferrin receptor) as the recognition moiety. The construction of this unique genetic linkage of the fusion protein between the RNase and the cell binding moiety eliminates the heterogeneity of chemically linked antibody-RNase conjugates. This is believed to contribute to the increased potency and decreased immunogenicity of the fusion protein reagent. Such recombinant fuision cytotoxic reagents are shown herein to be active at nM concentrations compared to μM concentrations required for toxicity of chemically linked hybrid cytotoxic reagents and are thus 1000 times more potent. For example, in FIG. 2 chemically linked cytotoxic reagents are shown to inhibit protein synthesis at μM concentration. In contrast, in FIG. 12 the recombinant fusion cytotoxic reagent inhibits protein synthesis when used in nM concentrations.

The invention includes nucleic acid constructs that encode the novel proteins described here. A nucleic acid construct is one which when incorporated into an appropriate vector is capable of replicating in a host. The constructs may be linked to other sequences capable of effecting the expression of the construct, such as promoters and enhancers. "Recombinantly fused" means that the subject product is the result of the manipulation of genes into new or non-native combinations.

The cytotoxic agent of the present invention may be directed toward various different types of cells by appropriate selection of a recognition moiety that binds to a specific cell surface marker found specifically or predominantly on the type of cell that is to be selectively killed. For example, the cytotoxic reagent of this invention includes those with a recognition moiety that binds to a tumor cell-specific surface marker, of which many are known in the art. In the presently preferred embodiment for a human application, the recognition moiety is human transferrin or a modified form thereof, which preferentially binds cells with high levels of the transferrin receptor, particularly certain tumor cells.

Further, for selectively killing cells that have been infected with an infectious agent, the recognition moiety advantageously binds to a marker of that infectious agent on the surface of an infected cell. Of particular importance for human clinical applications in viio are reagents comprising recognition moieties for cells infected by a virus, especially including latent or chronic virus infections, for example, HIV-1, Epstein-Barr Virus, herpes viruses (herpes simplex types I and II), hepatitis viruses (B, non-A-non-B, and delta), herpes zoster, and cytomegalovirus.

Although the recognition moiety of virus-specific cytotoxic reagents of this invention conveniently may be an antibody, advantageously the anti-viral recognition moiety may be a cell receptor for a virus or a modified form thereof In particular, given the known antigenic variability of the HIV-1 virus envelope protein, which limits the utility of any one antibody species in recognition of cells expressing that viral protein, for selective killing of the HIV-1 infected cells in AIDS patients, the recognition moiety of the present cytotoxic agent is advantageously the CD4 receptor protein. This receptor protein is the point of recognition between the HIV-1 virus and its specific target cell and, therefore, the envelope proteins of all immunologically distinct HIV-1 strains must nevertheless be able to bind to the CD4 protein. Thus, use of the CD4 protein in the present invention will direct the toxic moiety to kill cells infected by HIV-1 and expression on their surface the envelope protein which normally becomes embedded in the surface of cells producing that viral protein.

For treatment of patients infected with an intracellular parasite, including, for example, malaria, the recognition moiety is directed to a component of the agent which appears on the surface of infected cells, such as a marker for the merozoite form of a malaria parasite.

The cytotoxic agent of the present invention may also be directed toward immune dysfunctional cells in immune and autoimmune diseases. The recognition moiety of such cytotoxic reagents is directed towards T-cell antigens or subsets thereof, or B-cell idiotypes.

For use as a contraceptive, the recognition moiety of the cytotoxic reagent binds to a specific cell surface marker found specifically or predominantly on the surface of cells in the spermatogenic or oogenic linage. For example, the lutropin/choriogonadotropin (LH/CG) receptor.

The present invention also relates to a pharmaceutical composition comprising a cytotoxic reagent of the present invention and a pharmaceutically acceptable carrier. Advantageously, the pharmaceutical composition is suitable for parenteral administration. The cytotoxic reagent of the present invention may be administered by various means appropriate for different purposes, for example, for treating tumors in various parts of the body, according to methods known in the art for other immunotoxins. (See, for example, Rybak et al., 1990, "Human Cancer Immunology", in Immunology and Allergy Clinics of America, W. B. Saunders, and references cited therein). These means of administration include, for example, injection by intravenous, intrathecal, intratumoral, intraocular, and intraarterial routes, to bathe particular tumor beds or the brain in high concentrations of the reagent; administration directly into the wound during surgery (intracranially, for example); administration in an enema (for colon cancer, for instance); administration in the form a spray into the bronchi or nasopharyngeal cavity; administration topically (for example, for treating melanoma); administration by drip into the peritoneal cavity (e.g., for certain forms of ovarian cancer); and administration transvaginally or transurethrally. Accordingly, the present invention also relates to pharmaceutical compositions comprising a cytotoxic reagent of this invention and a pharmaceutically acceptable carrier, particularly such compositions which are suitable for the above means of administration.

Further, the present invention relates to a method of selectively killing cells using a selective cytotoxic reagent of the present invention. The method comprising contacting the cells to be killed with a cytotoxic reagent of the present invention having a recognition moiety specific for a target on the surface of the cells to be killed under conditions allowing binding of the recognition moiety. Binding of the recognition moiety to the surface marker on a cell causes the toxic moiety of the reagent to selectively kill the cell. This method of the present invention may be used for cell separation in vitro by selectively killing unwanted types of cells, for example, in bone marrow prior to transplantation into a patient undergoing marrow ablation by radiation, for killing leukemia cells or T-cells that would cause graft-versus-host disease.

For methods of use in vivo, preferably the mammalian protein of the reagent used in this method is endogenous to the species in which the reagent is intended for use. Preferably, for use in humans, the cytotoxic reagent is a fusion protein comprising a humanized chimeric antibody and a toxic human protein. Specific in vitro methods of this invention include a method for the chemotherapeutic alleviation of cancer in mammals comprising administering a chemotherapeutically alleviating amount of a selective cytotoxic reagent according to the present invention. This invention further comprises a method for the chemotherapeutic alleviation of an infectious disease in mammals comprising administering a chemotherapeutically alleviating amount of a selective cytotoxic reagent according to the present invention.

EXAMPLES

In the following non-limiting examples, the present invention is exemplified by a cytotoxic reagent in which the toxic moiety is bovine pancreatic ribonuclease A and the recognition moiety is human transferrin, the target being tumor cells having high levels of the transferrin receptor.

The present invention is further exemplified by a cytotoxic reagent comprising a fused protein in which the toxic moiety is human angiogenin and the recognition moiety is a human-mouse chimeric antibody against the transferrin receptor. The target of the cytotoxic reagent is tumor cells expressing high levels of the transferrin receptor.

Also exemplified are numerous examples of single chain fusion proteins in which the toxic moiety is angiogenin or EDN.

Example 1

Figure 1:
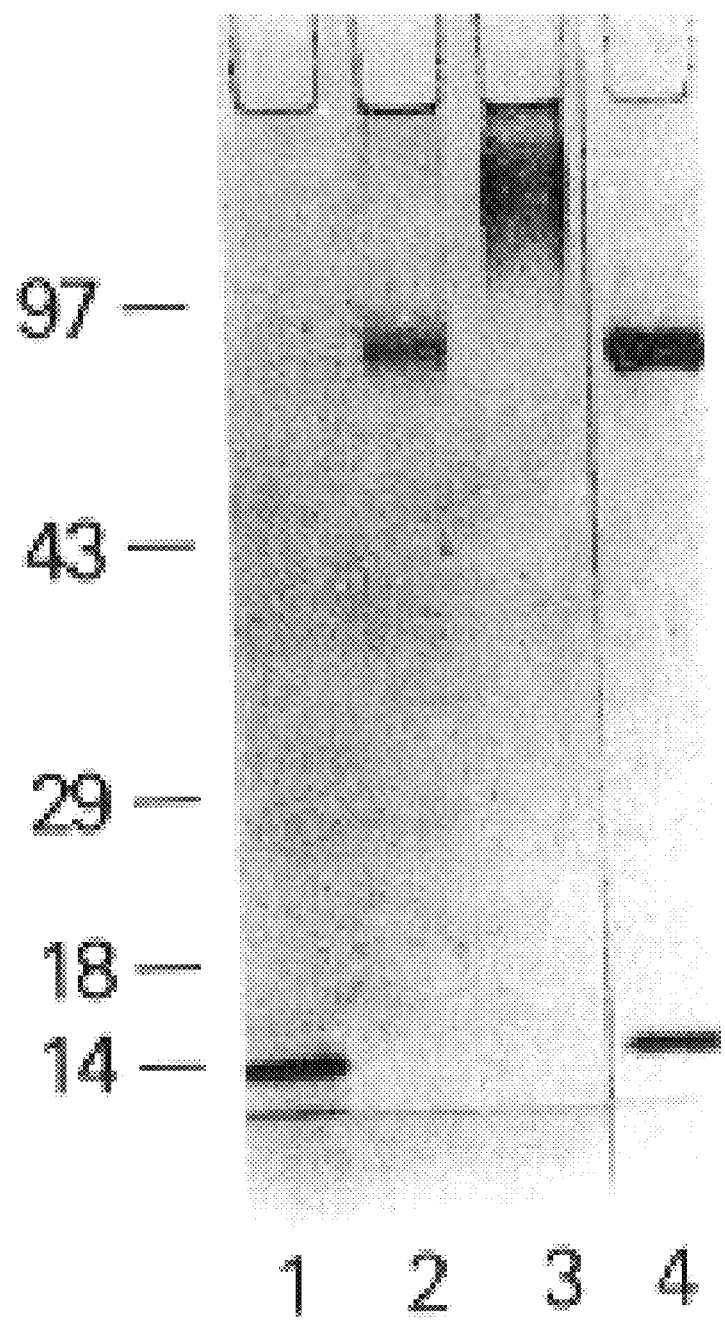
FIG. 1. SDS gel analysis under reducing and non-reducing conditions of Tfn-RNase conjugate. The purified conjugate was analyzed on a 10–20% gradient SDS-acrylamide gel and compared to unreacted RNase and transferrin. The samples were reduced by boiling for 5 min. in SDS sample buffer containing 2-mercaptoethanol. Lane 1, RNase. Lane 2, Transferrin. Lane 3, Tfn-RNase conjugate. Lane 4 Tfn-RNase conjugate with the disulfide linkage reduced with β-mercaptoethanol.

Preparation of Transferrin-RNase Conjugate. A heterobifunctional reagent, N-succinimidyl 3-(2-Pyridyldithio) propionate (SPDP), was used to introduce 2-pyridyl disulfide groups into bovine pancreatic RNase. The derivatized RNase was reacted with 2-iminothiolane (2-IT) treated human transferrin (Tfn) to form a conjugate via intermolecular disulfide bond formation. RNase-Tfn conjugates were separated from unreacted RNase and Tfn multimers by gel filtration on a TSK-3000 HPLC column. Analysis of the conjugate by SDS acrylamide gel electrophoresis under reducing and non-reducing conditions showed that the conjugate had a higher MW than transferrin and upon reduction the conjugate broke apart into proteins migrating equivalent to RNase and transferrin (FIG. 1). The purified conjugate did not appear to contain significant amounts of free transferrin or RNase (FIG. 1). HPLC analysis as well as integration of the amounts of RNase and transferrin appearing upon reduction of the conjugate is consistent with the conjugate containing Tfn-RNase conjugate preparation in an approximate 1:1 molar ratio.

Intact RNase-transferrin conjugate displayed potent RNase activity that was linear in the range from 1 to 10 nM in an assay that measured release of acid soluble nucleic acids from tRNA. This activity was 3–10 times less than that expected from the calculated amount of RNase in different conjugate preparations compared to a known standard.

Freezing Antibody-RNase Conjugates Greatly Increases Activity. We have also similarly made chemical antibody-RNase conjugates with another monoclonal antibody, 454A12, against the human transferrin receptor and RNase A (Calbiochem). The immunotoxins were collected in two fractions; pool 1 (P1) fractions 21–27 min. and pool 2 (P2) fractions 28–36 min.

We discovered that, whereas antibody-RNase conjugates stored at 4° C. had little effect on protein synthesis of K562 cells at 0.1 μM (P1) and 0.44 μM (P2), the same conjugates stored frozen inhibited protein synthesis by 99% (P1) or 78% (P2) at these same concentrations. Thus, freezing prevented the loss of protein synthesis inhibition activity of both the P1 and P2 molecular weight forms of antibody-RNase hybrids. Similar results were found with another anti-human transferrin receptor monoclonal antibody, 5E-9 coupled to RNase A.

The protein synthesis inhibition activity observed in samples stored at −20° C. also decreases upon incubation of the conjugates at 23° C. When 5E-9-RNase P2 is incubated for 5 h at 23° C., protein synthesis inactivation activity decreased more than 10-fold. Refreezing 5E-9-RNase P2 resulted in more than a 10-fold increase in the cytotoxicity of the conjugate, indistinguishable from the original material. Thus, the loss in activity that occurred upon storage at 23° C. was completely reversible by freezing. Freezing may cause aggregation of the conjugates or conformational changes in RNase A. Protein synthesis was measured as described below.

To examine whether or not the inhibitory activity of the antibody-RNase conjugates was unique to the transferrin receptor, RNase A was conjugated to an antibody to the human T cell-specific antigen CD5 (T101). T101-RNase inhibited protein synthesis of target cells and was stabilized by freezing as were the two anti-transferrin RNase conjugates. Upon coupling to antibodies, RNase A can inhibit protein synthesis in cells via different cell surface receptors.

The dramatic difference between the frozen conjugates and the non-frozen ones was very surprising, particularly in light of the teaching in the immunotoxin art, that other immunotoxins employing other toxic components such as Diphtheria toxin lose their activity upon freezing because of aggregation.

Inhibition of [$^{14}$C]Leucine Incorpoiration by Tfn-RNase. The RNase-Tfn conjugate inhibits protein synthesis in several human and non-human derived cell lines. Increasing concentrations of Tfn-RNase from $10^{-9}$ to $10^{-7}$M inhibited protein synthesis in a dose dependent manner as determined by the incorporation of [$^{14}$C]leucine into K562 cells (FIG. 2). The IC$_{50}$ for different conjugate preparations and different assays ranged from $8\times10^{-9}$ M to $8\times10^{-8}$M. The dose response curves for two different conjugate preparations in the same assay are shown in FIG. 2. Both dose response curves decline steeply from about 80% to 10% protein synthesis with a 10-fold increase in concentration and maximum inhibition lowers incorporation of label to 1–2% of control. Bovine pancreatic RNase or SPDP derivatized RNase only inhibits incorporation of the [$^{14}$C]leucine label into K562 cells at $1\times10^{-4}$M or more (FIG. 2). In experiments where complete dose response curves for RNase were obtained it required a 100 fold increase in RNase to effect the 80% to 10% decrease in protein synthesis. The SPDP treated RNase was consistently about 10-fold more potent than untreated RNase. The increased activity of the conjugate compared to RNase depends on the chemical linkage to Tfn since mixtures of Tfn and RNase do not significantly affect protein synthesis compared to RNase alone (FIG. 2). Protein synthesis in guinea pig L2C cells, monkey Vero cells and human TE671 rhabdomyosarcoma cells was also inhibited by Tfn-RNase ($5\times10^{-8}$M–$1\times10^{-7}$M).

Tfn-RNase inhibits protein synthesis at concentrations 10,000 fold lower than free RNase. To demonstrate that transferrin mediates the toxicity of the conjugate via binding the transferrin receptor, excess transferrin was incubated with the conjugate to compete for binding. The competition data show that 70 g/ml of Tfn blocks the action of Tfn-RNase 10-fold. To address the role of RNase in the conjugate two inhibitors of pancreatic bovine RNase were added to the protein synthesis inhibition assay. The addition of PRI or a new more potent inhibitor of RNase to culture medium along with Tfn-RNase blocked the activity of the conjugate. Thus both protein components of the conjugate are required for the inhibition of protein synthesis by the Tfn-RNase conjugate.

Kinetics of Protein Synthesis Inhibition Caused by Tfn-RNase in K562 cells. Cytotoxic proteins such as ricin and diphtheria toxin inhibit protein synthesis following a dose dependent lag period (Olsnes et al., 1976, *J Biol Chem.* 257:3985, Uchida et al., 1973, *J Biol Chem.* 248:3845) The inhibition of protein synthesis is first order and log-linear versus time. The time course for Tfn-RNase at four different concentrations is shown in FIG. 3. Like ricin and diphtheria toxin Tfn-RNase exhibits a dose dependent lag time and then protein synthesis decreases according to a first order process. The highest concentration of Tfn-RNase ($5\times10^{-7}$M) presented in FIG. 3 was saturating since higher concentrations did not significantly increase the steepness of the slope (not shown).

The rate of protein synthesis inactivation by both ricin and diphtheria toxin increases with increasing concentration of the toxin. However, the relationship between the rate of killing by the toxins and concentration of toxin is not linear but increases proportionally to the square root of the toxin concentration. This diminishes the achievable extent of killing of target cells. Advantageously, the relationship between the killing rate and the concentration of the Tfn-RNase conjugate does not follow the square root function as does ricin and diphtheria toxin but correlates linearly with concentration. This should enable increasing doses of Tfn-RNase to yield proportionate gains in log target cell kill.

The rate of intoxication of Tfn-RNase was calculated and compared to data similarly calculated from published figures for ricin A-chain conjugated with transferrin (Tfn-RTA) (Raso et al., 1984, *J Biol Chem.* 259:1143–1149) and one of the most potent ITs reported to date, transferrin coupled to a binding deficient mutant of DT (Tfn-CRM107) (Greenfield et al., 1987, *Science* 238:536–539). Measured in logs/hour, Tfn-RNase inactivated protein synthesis at 6.5 times the rate of Tfn-RTA and was only 1.7 times slower than Tfn-CRM107.

Clonogenic Assay of Tfn-RNase. The extent of the cell killing in clonogenic assays was performed. After 24 hours in the presence of conjugate K562 cells were washed, resuspended in complete medium, diluted serially and plated into 96 well microtiter plates. The wells that contained surviving cells were scored after 2 wks and the results of a representative experiment is presented in FIG. 4. Tfn-RNase ($10^{-7}$) killed between 2–3 logs of cells and a concentration of $10^{-6}$M killed at least 6 logs of cells. In contrast to the results in the protein synthesis assay (FIG. 1) the clonogenic assay indicates no toxicity of 7×10-5M SPDP-RNase. The elimination of 6 logs of cells can be compared to 3–4 log cell kill for RTA conjugates.

Animal Toxicity. Transferrin in plasma is about 4 mg/ml in man and may block the toxicity of Tfn-RNase is vitro. The central nervous system in an important site of metastases of peripheral tumors such as breast and lung cancer as well as a site of primary tumors. The CSF fluid contains 14 g/ml free transferrin, an amount that would block the toxicity of Tfn-RNase only 2 fold. The toxicity of Tfn-RNase to animals was examined after direct injection into the CSF fluid. Tfn-RNase was injected into the CSF fluid of rats and guinea pigs to yield an initial concentration of 2×10-6M, twice the concentration that killed 6 logs of cells in culture. No toxicity was observed in these animals.

Monoclonal Antibodies Coupled to RNase. A monoclonal antibody specific for the human transferrin receptor, B3/25 was coupled to RNase by the same method as transferrin resulting in a disulfide coupled conjugate. Incubating K562 cells for 24 hours with the conjugate, B/25-RNase at 1×10$^-$7M to 1×10$^{-8}$M resulted in 50 to 80% inhibition of protein synthesis (FIG. 5). The antibody is specific for the human transferrin receptor and does not bind the green monkey transferrin receptor. A green monkey cell line, Vero was not affected by the same concentration of B3/25-RNase conjugate.

Example 2

Construction of the Anti-transferrin receptor-Ang Chimeric Gene.

Construction of the antibody-Ang fusion required modification of the Ang gene. PCR was used to introduce EcoRI sites 5' to the first codon of the mature protein (Kurachi et al., 1985, *Biochemistry* 24:5494–5499) and past the EcoRV site in the 3' untranslated region of the gene to include the stop and poly A signals of the native gene. This Ang gene bordered by two EcoRI sites was cloned into pBluescript®, completely sequenced and a clone without mutations was selected for the fusion to the mouse/human chimeric anti-transferrin receptor antibody gene (FIG. 6). The antibody gene (Hoogenboom et al., 1990, *J. Immunol* ., 144:3211–3217) was previously fused to the gene for TNF at the 5' region of the CH2 domain of the antibody thus leaving the hinge region and dimerization of the heavy chain unaffected (Hoogenboom, H., Volchaert, G. & Raus, J., 1991, *Mol Immunol* 28:1027–1037). The CH2-TNF chimeric gene was used to generate a HindIII-BamHI EcoRI fragment that encompassed the antibody gene free of the TNF gene. The EcoRI Ang fragment was ligated to the antibody gene and a clone with the Ang gene in the correct orientation was obtained. The junctions between the antibody heavy chain and the Ang gene are depicted in FIG. 7.

The chimeric heavy chain Ang gene was cloned into the HindIII-BamHI sites of pSV2gptMOV$_H$NP. In this vector the expression of the chimeric gene is regulated by an immunoglobulin transcription enhancer element and promoter, both situated upstream of the gene (Neuberger, M., 1983, *EMBO J*2:1373–1378). Secretion ofthe gene product is directed by an immunoglobulin derived signal peptide sequence.

Isolation and Analysis of Transfectomas. An anti-transferrin receptor chimeric light chain producing cell line (E12B5) (Hoogenboom et al., 1990, *J. Immunol.* 144:3211–3217), was transfected with the pSV2 derived vector containing the CH2-Ang gene. After selection for the presence of the gpt gene, culture supernatants of clones testing positive for human IgG were followed for reproducible human IgG activity. The eight highest producing clones were subcloned by limiting dilution. Of these, clone CH2.5Ang was selected for further characterization.

The amount of secreted CH2.5Ang ranged from 1 to 5 ng/ml as determined in a human IgG-detecting ELISA and from 1–2 ng/ml when Ang was detected by ELISA. This level of secretion of the chimeric antibody linked to Ang was lower than that described for other chimeric enzymes (Casadei et al., 1990, *Proc. Natl. Acad. Sci. USA* 87:2047–2051; Williams et al., 1986, *Gene* 43:319–324). Although both Ang or TNF can be cytotoxic to cells, albeit under different conditions, expression in mammalian cells should target them through the secretory pathway of the cell. However, the antibody secretory pathway is being used to secrete these fusion proteins and this may not protect the cell as much as the normal biosynthetic pathway for these proteins. Therefore, high level expression could be toxic to the cells thus causing the self-selection of low producers. In this case, the expression of these recombinant proteins as Fab or single chain antibody fusion proteins in *E. coli* should be considered.

Anti-human IgG SEPHAROSE® beads were used immunoprecipitate [$^{35}$S]-Met-biosynthetically labeled proteins from CH2.5Ang culture medium. After elution of the precipitated proteins, the samples were reduced, separated on an SDS gel and analyzed by autoradiography (FIG. 8). The expected size of the CH2Ang fusion protein is 43 kD (14 kD from the Ang portion) and a band was present at 43 kD. The significance of the other bands in that region is not known but heterogeneous heavy chains have been reported for other antibody-enzyme chimeras using pSV2gpt vectors (Neuberger et al., 1984, *Nature (London)* 312:604–612). A protein corresponding to the expected size of the chimeric light chain (Hoogenboom, H., Volckaert, G. & Raus, J., 1991, *Mol Immunol* 28:1027–1037) was also present. In addition the presence of the light chain was confirmed by ELISA and the presence of the heavy chain chimera of the correct $M_r$ was further demonstrated by immunoblot analysis.

CM-Cellulose Fractionation of CH2.5Ang Culture Medium and Characterization of Ang Specific In Vitro Activity. To characterize the in vitro activity of the Ang portion of the fusion protein CH2.5Ang culture medium was fractionated over a CMC column. At neutral pH Ang is cationic and binds to CMC (Fett et al., 1985, *Biochemistry* 24:5480–5485) whereas most of the components of the growth medium used for these experiments do not absorb to the column (FIG. 9A, top). Human IgG also fails to absorb to the CMC column at neutral pH. Culture medium conditioned by cells secreting CH2.5Ang IgG immunoreactive material was passed over a CMC column, washed and then treated with increasing salt in a stepwise manner (FIG. 9B, middle). In contrast to growth medium (FIG. 9A, top), most of the IgG immunoreactive material eluted with 0.5M salt and the material in this fraction was increased relative to the starting material. Since only the Ang portion of the fusion protein binds to CMC, the anti-human reactive material eluting with 0.5M salt must be linked to Ang. These data indicate that a fusion protein consisting of the chimeric antibody and Ang is being secreted.

The human serum RNase inhibits the translational capacity of rabbit reticulocyte lysates in a distinctive manner and the inhibition is prevented by PRI, a ribonuclease inhibitor (St. Clair et al., 1987, *Proc. Natl. Acad. Sci. USA*

84,8330–8334). Two concentrations of partially purified 0.5M CMC material containing CH2.5Ang at 200 or 400 ng/ml was added to a standard rabbit reticulocyte lysate in vitro translation system and incorporation of [$^{35}$S]-Met into newly synthesized proteins was measured (FIG. 9C, bottom). A concentration dependent inhibition of protein synthesis was observed that was completely reversed by PRI. Analysis of the 0.5M CMC material by SDS gel electrophoresis showed that a protein of the correct $M_r$ for the Ang fusion protein was present but several other low $M_r$ proteins were also present in this material. The presence of Ang of the correct $M_r$ was confirmed by immunoblot analysis. Recent studies have determined that Ang inhibits protein synthesis in the rabbit reticulocyte lysate and in Xenopus oocytes solely by degrading tRNA. The addition of tRNA reverses protein synthesis caused by other RNases. In the present study, tRNA partially reverses the inhibition of protein synthesis caused Ang in the 0.5M CM-cellulose fraction thus demonstrating that chimeric Ang expresses one of its characteristic in vitro activities.

Immunoprecipitation and immunoblot analysis of the culture supernatant from CH2.5Ang described in the preceding section revealed no degradation of the fusion proteins. In previous studies, using similar constructs to express chimeric TNF proteins (Hoogenboom, H., Volckaert, G. & Raus, J., 1991, Mol Immunol 28:1027–1037), the culture supernatant was observed to secrete fusion proteins of the correct size except under circumstances where serum free medium was used extensive proteolytic degradation was evident. In this study, immunoblot analysis of the 0.5M CMC fraction showed degradation of the human IgG reactive portion of the fusion protein but the Ang portion of the fusion protein was the correct $M_r$. Other attempts to isolate CH2.5Ang from transfectoma medium were hampered by the very low concentration of the fusion protein in the culture supernatant which may have contributed to the persistent degradation of the IgG portion of the fusion protein. For this reason, further biological characterization of the fusion protein was carried out with cell culture supernatant.

Characterization of the Effect of CH2.5Ang Culture Medium on Growth and Protein Synthesis in Human Leukemia Cells. Previous studies from the inventors' laboratory showed that bovine pancreatic RNase chemically linked to transferrin or antibodies to the transferrin receptor formed hybrid proteins with cytotoxic effects toward K562 human erythroleukemia cells. Since Ang is a member of the RNase superfamily (Strydom et al., 1985, Biochemistry 24:5486–5494), it was of interest to treat K562 cells with CH2.5Ang containing culture medium. K562 cells were plated into CH2.5Ang culture medium and the growth of the cells was compared to K562 cells plated into the same growth medium that had not been incubated with CH2.5Ang secreting cells. The growth of the cells in the CH2.5Ang medium was inhibited and by two weeks the wells contained mostly cell debris (FIG. 10). In another experiment, addition of excess E6 mouse monoclonal anti-transferrin receptor antibody to the wells at the time K562 cells were plated in the medium retarded the growth inhibitory effect of CH2.5Ang culture medium (FIG. 11) but did not affect the growth of K562 cells in the control growth medium.

The effect of CH2.5Ang medium on protein synthesis in K562 cells was examined and compared to the effects of purified recombinant Ang protein, and the mouse monoclonal antitransferrin receptor antibody (E6) that contributes the variable domains for the chimeric antibody gene used for these studies. This chimeric E6 antibody retains the specificity of the mouse E6 (Hoogenboom et al., 1990, J. Immunol., 144:3211–3217) and neither the chimeric E6 or mouse monoclonal E6 compete for transferrin and thus do not block cell growth. Although neither Ang, E6 nor a mixture of the two proteins inhibits protein synthesis in K562 cells, CH2.5Ang medium inhibits protein synthesis by 50% after a 24 h incubation (FIG. 12A, top). Furthermore, the addition of excess E6 antibody immediately after plating K562 cells into CH2.5Ang medium blocks the toxicity when protein synthesis is measured at 24 h (FIG. 12B, middle). Since neither E6, Ang nor the chimeric antibody used to make the fusion protein inhibit protein synthesis or cell growth, these results imply that inhibition of protein synthesis of the CH2.5Ang medium is due to the combined functions of the secreted fusion protein.

Further, the antibody part of the fusion protein was shown to recognize the human transferrin receptor and not the transferrin receptor on monkey cell lines. Incubation of Vero a monkey cell derived line does not result in inhibition of protein synthesis (FIG. 12C, bottom) or Vero cell growth. This shows cell-type specificity again showing transferrin receptor mediated toxicity of the antibody-Ang fusion protein.

Mechanism of Action of CH2.5Ang. A comparison of RNase and toxins upon injection into Xeopus oocytes showed that some RNases were as potent as ricin to inhibit oocyte protein synthesis but Ang was approximately 100 times less potent. In the oocyte, the toxicity of RNase A correlated directly to degradation of oocyte RNA. In contrast to general degradative RNases, Ang inhibited oocyte protein synthesis by degrading tRNA. Therefore, it is predicted that the mechanism of cell killing by CH2.5 Ang does not involve general degradation of cellular RNA but the involvement of tRNA degradation in cellular toxicity cannot be ascertained by these experiments. Since Ang was less cytotoxic in the oocyte compared to degradative RNases other human RNase gene products may be even more powerful in their ability to selectively destroy tumor cells.

Materials and Methods

The following materials and methods are used in the practice of the present invention.

Materials. Bovine pancreatic RNase A was purchased from CALBIOCHEM (San Diego, Calif.). Human placental ribonuclease inhibitor (PRI) from Promega Biotech (Madison, Wis.) and Inhibit-ACE RNase was from 5'-3' (Paoli, Pa.). Human transferrin and tRNA type x was from Sigma (St. Louis, Mo.) Dithiothreitol (DTT), N-Succinimidyl 3-(2-Pyridyldithio)propionate (SPDP),2-Iminothiolane (2-IT) were purchased from Pierce Chemical Co. (Rockford, Ill.). Plastic 96 well microtiter plates were from Nunc (Gaithersburg, Md.) and all cell culture supplies were from GIBCO (Grand Island, N.Y.).

Xanthine and hypoxanthine were purchased from Sigma (St. Louis, Mo.). DNA modifying enzymes and restriction endonucleases were from Stratagene (La Jolla, Calif.), mycophenolic acid and other cell culture reagents were obtained from Bethesda Research Laboratories (Gaithersburg, Md.) Or GIBCO (Grand Island, N.Y.). [$^{35}$S]-Methionine ([[$^{35}$S-Met]), ELISA reagents and biotinylated antibodies to human IG and human kappa were from Amersham (Arlington Heights, Ill.), biotinylated goat anti-rabbit IgG was from (Kirkegaard and Perry, Gaithersburg, Md.). Affinity purified goat anti-human IgG was purchased from Jackson Immunoresearch Labs (West Grove, Pa.) and goat anti-human light chain was from Southern Biotechnologies (Birmingham, Ala.). Calf liver tRNA was purchased from Boehringer (Indianapolis, Ind.). Reticulocyte lysate and placental ribonuclease inhibitor (PRI) were obtained from Promega Biotech (Madison, Wis.).

Ang was cloned from the gene for human angiogenin and expressed in $E.\ coli$. Since it is a recombinant form of the human plasma protein and contains an additional N-terminal methionine is designated as Ang in these studies. Rabbit antibodies to human angiogenin were a generous gift from Drs. Karen Olson and James Fett of the Center for Biochemical and Biophysical Research in the Sciences and Medicine of Harvard Medical School.

Cell Lines. K562 (human erythroleukemia-derived cell line) was grown in RPMI 1640 medium containing 10% fetal calf serum (FCS), 2 mM glutamine, 1 mM sodium pyruvate, and 10 g/ml gentamycin.

E12B5 is a chimeric cell line that produces and secretes the chimeric mouse/human light chain for the E6 anti-transferrin receptor antibody (Hoogenboom et al., 1990, $J.\ Immunol.$ 144:3211–3217). This cell line was grown in RPMI 1640 medium containing 10% fetal calf serum, and supplemented with 2 mM glutamine, 1 mM sodium pyruvate, non-essential amino acids, 10 µg/ml gentamycin and 10 mM Hepes.

Vero (monkey kidney cell derived line), TE671 (human myosarcoma derived cell line) were maintained in Dulbecco's modified Eagle's medium with the above supplements. The cell lines were grown at 37° C. in 5% $CO_2$ in a humidified atmosphere. $L_2C$ leukemia is a spontaneous transplantable B cell leukemia of Strain 2 guinea pigs. $L_2C$ leukemia cells were harvested from the blood of animals in the terminal stage of the leukemia as previously described (Zovickian et al., 1988, $J\ Neurosurg.$ 68:767–774). The prepared cells were used within 24 h.

Immunotoxins. RNase was modified with SPDP as described (Carlsson et al., 1978, $Biochem.\ J.$ 173:723–737) and under the conditions used 1.5-mol SPDP was incorporated per mol RNase. Transferrin was reacted with 2-IT as described (Johnson et al., 1988, $J\ Biol\ Chem.$ 263:1295–1300), and incubated with SPDP-RNase (RNase:Tfn 10:1 mol:mol) 18–24 h at 4° C. The conjugate was purified by gel filtration on a TSK-3000 high pressure liquid chromatography (HPLC) column. Individual peaks were characterized biologically using inhibition of protein synthesis in K562 cells as an assay. The greatest activity was associated with the peak that contained transferrin and RNase in a 1:1 molar ration which was determined by reducing the conjugate to its individual proteins followed by HPLC analysis. The amount of total protein in the conjugate was quantified by Lowry assay using BSA as a standard.

Protein Synthesis Assay. Protein synthesis in cells growing in suspension or in adherent cells was measured as previously described (Johnson et al., 1988, $J\ Biol\ Chem.$ 263:1295–1300). Briefly, cells were plated at concentrations given in Figure or Table legends into 96 well microtiter plates in leucine free RPMI 2640 medium without fetal calf serum in a volume of 100 µl. Sample or control additions were added in a volume of 10 µl and the plates were incubated at 37° C. for the times indicated for each experiment. Phosphate buffered saline containing 0.1 µCi of [$^{14}$C] leucine (20 µl) was added for 1 hr and the cells were harvested onto glass fiber filters using a PHD cell harvester, washed with water, dried with ethanol and counted. The results are expressed as % of [$^{14}$C]leucine incorporation in the mock-treated cultures. All determinations were done at least four times.

Clonogenic Cell Assay. The number of clonogenic cells surviving treatment with conjugate or other additions was determined by using a limiting dilution assay. Cells were treated with additions in a 1 ml volume in 24 well plates for 18–24 hr under the same culture conditions described in the section on protein synthesis assays. The cells were harvested by centrifugation and washed with complete culture medium. The washed cells were resuspended in complete growth medium and 6 serial 10 fold dilutions were made. Ten aliquots (100 µl) of each dilution were plated in 96-well microtiter plates. Plates were incubated for 14 days at 37° C. in a humidified atmosphere. Medium was replenished every 3–4 days. Wells with growing colonies were scored by examination under an inverted phase microscope. The number of clonogenic cells remaining from the original number treated was calculated using a Spearman-Karber estimator (Johnson et al., 1961, $Biometrics$ 17:79–88).

RNase Assay. tRNA was dissolved at 1 mg/ml in water and added to a reaction mixture containing RNase and buffer (Tris, 0.5M, pH 7.5, EDTA 5 mM, human serum albumin, 0.5 mg/ml) in a total volume of 300 ml in polypropylene microfuge tubes. The mixture was incubated for 30 min at 37° C. and then placed on ice. Perchloric acid (6%, 700 ml) was added and the mixture was left on ice for 10 min. and then microfuged for 10 min. at 4° C. An aliquot of the supernatant was read at 260 nm. The unknowns were compared to a standard curve of bovine pancreatic RNase A. This assay was modified from a detailed protocol described by Bond (Bond, M., 1988, $Anal\ Biochem.$ 173:166–173).

Construction of the Chimeric Heavy Chain Ang Gene. The cloning of the human Ang gene and the chimeric antibody genes (Hoogenboom et al., 1990, $J.\ Immunol.$ 144:3211–3217) were previously reported. The recombinant DNA work was performed by standard procedures (Maniatis et al., Molecular cloning, a laboratory manual (Cold Spring Harbor Laboratory Cold Spring Harbor, N.Y. 1982) and DNA sequencing was performed according to the method of Sanger (Sanger et al., 1977, $Proc.\ Natl.\ Acad.\ Sci.\ USA$ 81:7161–7165) using reagents from United States Biochemical (Cleveland, Ohio). The polymerase chain reaction (PCR) used to modify Ang gene sequences was done with reagents from Perkin Elmer Cetus. The oligonucleotides were synthesized using the CYCLONE PLUS® DNA synthesizer from Milligen Biosearch (Burlington, Mass.).

Introduction of DNA into Myeloma Cells, Selection of Transfected Cells and Screening for Antibody secreting Cells. DNA was introduced into mammalian cells Ausing electroporation (Potter et al., 1984, $Proc.\ Natl.\ Acad.\ Sci.\ USA$ 74:5463–5467) with the GENE PLUSER® Apparatus of BioRad (Richmond, Calif.) as described previously (Hoogenboom, H., Volckaert, G. & Raus, J., 1991, $Mol\ Immunol$ 28:1027–1037). Briefly, an electroporation cuvette containing $2\times10^6$ cells and 5–20 µg of linearized plasmid DNA in 0.8 ml of phosphate buffered saline (PBS) was placed at 0° C. The cells were subjected to a single voltage pulse at 200 V using a capacitance setting of 960 µF. Selection of transfected cells containing the gpt gene was carried out with 1 µg/ml mnycophenolic acid, 250 µg/ml Xanthine and 15 µg/ml hypoxanthine. Clones were visible after 1–2 weeks. Individual clones were selected by limiting dilution in the absence of feeder cells and the best producing clone was designated CH2.5Ang.

Screening for antibody production was done by ELISA detecting human IgG or kappa chain as described elsewhere (Krolick et al., 1980, $Proc.\ Natl.\ Acad.\ Sci.\ USA$ 77:5483–5486). The assay measures antibody concentrations ranging from 1–100 ng/ml and is specific for the detection of human gamma or kappa chain. Detection of Ang in transfectoma supernatants was accomplished by ELISA using a method previously published (Shapiro et al., 1987, *Biochemistry* 26:5141–5146).

Biosynthetic labeling with [$^{35}$S]-Met, Immunoprecipitation and Immunoblot. Biosynthetic labeling of secreted proteins was accomplished as described using goat anti-human IgG-SEPHAROSE® beads (Hoogenboom, H., Volckaert, G. & Raus, J., 1991, *Mol Immunol* 28:1027–1037). After electrophoresis of the eluted samples on SDS gels, the gels were treated with ENLIGHTENING® (Dupont, Boston, Mass.), dried and exposed at −70° C. with intensifying screens. For immunoblotting, the samples were electrophoresed on SDS gels and then transferred to nitrocellulose paper (BioRad) using the Novex electrophoresis and immunoblot apparatus. Detection of Ang was performed with modifications of a protocol devised by Dr. Karen Olson. After the transfer, the blot was incubated in PBS 0.05% TWEEN-80® overnight at 4° C. The blot was incubated then with rabbit anti-angiogenin for 2 hr at RT, washed with PBS-0.05% TWEEN-80® and incubated with biotin labeled anti-rabbit IgG for 2 hr at RT. Detection of human Ang vas accomplished with a 1/1000 dilution of goat anti-rabbit IgG. The procedure vas the same as that used to detect human IgG or human kappa (Hoogenboom, H., Volckaert, G. & Raus, J., 1991, *Mol Immunol* 28:1027–1037).

Fractionation of Culture Supernatant and In Vitro Inhibition of Protein Synthesis. Carboxymethlycellulose (CMC) was equilibrated with 10 mM Tris pH 7.5 and poured into a column with dimensions of 3 cm×10 cm. Five hundred ml cell culture supernatant that had been collected form CH2.5Ang secreting cells in T150 flasks and stored frozen at −20° C. was passed over this column. Once the supernatant was thawed all further manipulations were performed at RT. The flow through was collected and the column was washed with two column volumes of the equilibration buffer. Step wise elution was performed by increasing the salt concentration with sodium chloride. At each salt concentration ten ml fractions were collected until the O.D.$_{280}$ was below 0.02 O.D. units. Fractions with the highest O.D. units were pooled for each salt concentration and the eluates were dialyzed into PBS. Some of each fraction was concentrated and analyzed by SDS electrophoresis. The proteins were detected using both Coomasie blue stain and silver stain. Immunoblot analysis was performed to detect both human gamma and kappa chains as well as human Ang.

The in vitro translation assay was performed as previously described (St. Clair et al., 1987, *Proc. Natl. Acad. Sci. USA* 84,8330–8334). Briefly, rabbit reticulocytes lysate was incubated with or without additions for the time specified. For the reconstitution of activity with tRNA, the lysate was preincubated with CMC purified CH2.5Ang for 30 min and all further nuclease activity was stopped by inhibiting the treated lysate with PRI. Translation was initiated by the addition of a mix containing Brom mosaic virus RNA, 19 amino acids minus Met, and [$^{35}$S]-Met. The amount of protein synthesis was determined by the incorporation of [$^{35}$S]-Met into products precipitable by 10% trichloroacetic acid (TCA).

Growth and Protein Synthesis Assays. Cells were plated into growth medium or growth medium from cell culture supernatants that had been tested for the presence of human IgG. Cell growth was monitored by counting trypan blue negative cells at the times indicated. Protein synthesis was determined in 96 well microtiter dishes in a volume of 100 μl. The plates were incubated at 37° C. for the times indicated for each experiment. PBS containing 0.1 mCi of [$^{414}$C]-leucine (20 μl) was added for 5 hr and the cells were harvested onto glass fiber filters using a PHD® harvester, washed with water, dried with ethanol and counted. The results are expressed as % of [$^{14}$C]-leucine incorporation in the control cultures.

Example 3

Expression and Purification of Recombinant RNase-antibody fusion proteins.

Oligonucleotide synthesis—Oligonucleotides were synthesized (0.2 μmole scale) on a dual column CYCLONE PLUS® DNA synthesizer (Milligen-Biosearch) and purified using OPC cartridges (Applied Biosystems).

Construction of a synthetic gene encoding EDN—A synthetic gene encoding EDN was designed using the *E. coli* preferred codon bias (Grantham et al. 1981). The sequence is set out in SEQ ID NO:4. The gene was constructed from 10 pairs of complementary oligonucleotides, carefully designed so that: i) annealing generated a 7 nucleotide overhang at the 5' end of the antisense strand of each pair, and ii) each overhang had a minimum of three mismatches with that of an inappropriate oligonucleotide pair. Each oligonucleotide (30 μg) was 5'-phosphorylated using the KinAce-It™ kit from Stratagene (La Jolla, Calif.). Unincorporated rATP was removed using a MERMAID® kit (Bio 101, La Jolla, Calif.). Appropriate oligonucleotide pairs (1 μg each) were annealed by heating to 65° C., and cooling over a period of 20 minutes to 4° C. The annealed pairs were mixed and ligated together using a DNA ligation kit (Stratagene), according to the manufacturer's instructions. A 1 μl aliquot of a 100-fold dilution of the ligation mix was subjected to PCR with a pair of primers designed to: i) incorporate restriction sites appropriate for cloning XbaI and BamHI at 5' and 3' ends of the gene respectively, ii) introduce a translation initiation codon immediately prior to the first nucleotide of the EDN gene, and iii) incorporate tandem translation termination codons immediately after the last nucleotide of the final codon. After PCR, a product of the required size was recovered from an agarose gel using the GENECLEAN procedure (Bio 101), digested with the appropriate restriction enzymes, and cloned into the bacterial expression vector, pET-11d (Novagen). The composition of the synthetic gene was confirmed by dideoxynucleotide chain terminating sequencing of double-stranded DNA templates using a SEQUENASE® II kit (United States Biochemical Corp., Cleveland, Ohio). Plasmids were propagated in the *E. coli* strain XL1-Blue (Stratagene). Other genes can be constructed similarly.

Materials—Yeast transfer ribonucleic acid was purchased from Sigma, bovine pancreatic RNase A from Calbiochem, PRI (placental ribonuclease inhibitor) from Promega (Madison, Wis.), and 0.4% Trypan blue stain from Gibco (Frederick, Md.). The Heparin SEPHAROSE® and SEPHADEX® G100 gels were obtained from Pharmacia. Tris/glycine gradient electrophoresis gels were from Novex (Encinitas, Calif.). Reagents for performing PCR were obtained from Perkin Elmer Cetus Instruments. Antibodies to denature RNase A and recombinant EDN were prepared for us by Assay Research, Inc., College Park, Md. Native EDN, kindly provided by Richard T. Davey (NIAID, NIH) was prepared as described (Saxena et al., *J. Biol. Chem.* 267(30):21982–21986 (1992)).

A. Construction of genes encoding single chain antibodies.

The construction of fusion genes comprising a chimeric antibody to the transferrin receptor fused to two different human RNase genes is described. The plasmids were expressed in E. coli in inclusion bodies, denatured and refolded and the recombinant proteins purified to a single band.

The chimeric antibody is derived from the gene encoding a murine monoclonal antibody (mAb) to the human transferrin receptor designated E6, described above.

Cloned genes of known sequence encoding $V_L$ and $V_H$ regions of the E6 mAb were used (Hoogenboom, et al., J. Immunol. 144:3211–3217 (1990), incorporated by reference herein), abrogating the necessity for cloning directly from hybridoma cDNA. These genes have been expressed previously in a mouse hybridoma cell line as a chimeric molecule including the constant regions of a human antibody and have been shown to retain antigen binding ability, confirming their origin as the variable region genes encoding functional E6 $V_L$ and $V_H$ chains.

The E6 sFv gene was assembled by the following procedure, using plasmids containing cloned $V_L$ and $V_H$ genes as templates, in the form 5'-$V_L$-[GGGGS]$_3$-$V_H$-3'. The [GGGGS]$_3$(SEQ ID NO:19) linker has been used effectively in the production of functional sFv and was originally designed to be devoid of ordered secondary structure, yet allow the two variable chains to assume the optimum orientation for antigen binding. E6$V_L$ and E6C$_H$ PCR primers included restriction sites appropriate for the cloning strategy, tails consisting of at least five nucleotides were routinely included at the 5' end of each primer, to facilitate digestion with restriction enzymes. E6C$_L$ and E6C$_L$ primers included an additional 5' extension encoding the peptide linker, [GGGGS]$_3$(SEQ ID NO:19). The extension of E6C$_L$ was exactly complementary to that of E6$V_H$. $V_L$ and $V_H$ genes were amplified separately (20 cycles), and PCR products were purified by extraction from 1.5% agarose gels using a GENECLEAN® kit. The product of both reactions was recovered in 40 μl of water; 1-μl aliquots of $V_L$ and $V_H$ products were then mixed and subjected to a further 20 cycles of PCR, using E6$V_L$ and E6C$_H$ primers only. The assembled sFv gene was cloned into the appropriate vector.

B. Construction of single chain angiogenin (Ang)—E6.
 1. pET-11d-ANG-FB-E6-His6. pET-11 d is an expression plasmid provided to us by Dr. F. William Studier, Brookhaven National Laboratory, also available from Novagen (Madison, Wis.).

ANG is the RNase (its sequence is set out in SEQ ID NO:1); FB is a spacer joining the antibody gene to the RNase gene; E6 is the single chain antibody, HIS is a tag for purification. The entire sequence is set out in SEQ ID NO:3 and the various regions designated. This has been expressed and the protein purified to a homogeneous protein and shown to have cytotoxic properties per the protocol set forth below.

2. pET-11d-ANG-E6. This construct is similar to the one above, but lacks the FB spacer and the HIS tag. See SEQ ID NO:2. It has been expressed and the protein partially purified per the protocol below.

C. Construction of single chain eosinophil-derived neutrophil (EDN)-E6.

The synthetic EDN gene was synthesized as described. Its sequence is set out in SEQ ID NO:4.
 1. pET-11d-EDN-FB-E6-His6. The sequence is set out in SEQ ID NO: 6.
 2. pET-11d-E6-FB-EDN. In this construct E6 is fused to the amino terminal of the RNase. In the one above it is fused to the C terminus. The sequence is set out in SEQ ID NO:5.

D. Construction of single chain RNase A-EGF.
 1. RNase A-EGF. Fusion in which the C terminus of the RNase gene is fused to the amino terminus of EGF. The gene for human EGF was synthesized in our laboratory as described. The method and sequences are described below.

The gene for human angiogenin (Ang) cloned from a human genomic library and used for the construction of a chimeric humanized immunotoxin described in Rybak et al. PNAS 89:3165–3169 (1992), incorporated by reference herein, and also a synthetic gene for human eosinophil derived neurotoxin (EDN) as described above were individually fused to the cDNA encoding a chimeric mouse human antibody to the transferrin receptor. The EGF gene is set out in SEQ ID NO:7. The human RNase gene is set out in SEQ ID NO:8 and the fusion of the two sequences is set out in SEQ ID NO:9.

The Ang or EDN DNA was modified by PCR technology to put an Xba I site at the NH2-terminus and a 13 amino acid spacer at the C-terminus:

cDNA encoding, a mouse/human antibody to the human transferrin receptor was modified by PCR technology. The NH2-terminus was modified by the addition of a 13 amino acid spacer and the C-terminus was modified by the introduction of 6 histidines and a BamHI site. The histidines provide a tag for the purification of the recombinant protein.

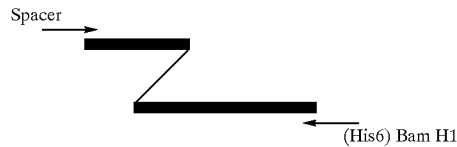

The PCR modified RNase DNAs and the PCR modified chimeric antibody DNA were then fused together using PCR technology. The fused DNA was ligated into pET-11 D expression vector and sequenced:

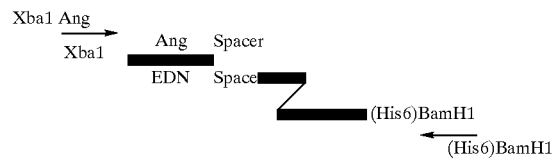

E. Expression.
The plasmid was freshly transformed each time into the expression bacteria E. coli BL21 (λDE3) and grown overnight at 37° C. The bacteria colonies of 4 plates (100 mm) were scraped into 100 ml of LB broth containing glucose and 100 μg/ml ampicillin and grown for 1–2 hours at 37° C. at which time the 100 ml broth was added to a 3 liter fermentor and grown to an OD$_{600nm}$ of 20. The culture was induced with 1 mM isopropyl β-D-thiogalactopyranoside (Bethesda Research Laboratories (Gaithersburg, Md.) for 2 hrs before the cells were harvested.

F. Protein Purification
Purification of the single chain RNase proteins was problematic largely due, we assume, to the fact that RNases are very basic and are bound to an enormous number of bacterial proteins. A great deal of experimentation was required to determine the effective amount of imidazole and the necessity for 1% TRITON X-100® in the elution buffer. A prior chromatography step was also required. RNases bind well to both heparin and CM cellulose or both so that these steps will work for other RNases.

Protein purification of Single Chain EDN (ScEDN) Preparation of protein from inclusion bodies was as described (Brinkman, U., Buchner, J. and Pastan, I. (1992) Proc. Nati. Acad. Sci. USA 89, 3075–3079, incorporated by reference herein). Following denaturation and refolding of the proteins the refolding mixture was dialyzed against 20 mM Tris-HCl, pH 7.5/100 mM urea, centrifuged and applied to a Heparin SEPHAROSE® column (5 ml column for each 160 mg of total protein). The column was washed with 2 column volumes of 20 mM tris-HCl, followed by 1 column volume of the same buffer containing 0.1M NaCl. Elution was accomplished by 4 column volumes of 20 mM Tris-HCl in 0.5M NaCl. The eluted protein was then added to 0.8 mM imidazole and 1% TRITON X-100 (Sigma Chemical, St. Louis, Mo.) and 0.6 ml $Ni^{2+}$ NTA agarose which binds the HIS tag (Quiagen, Chatsworth, Calif.). This amount of $Ni^{2+}$ NTA agarose binds 320 mg refolded protein as determined before the first chromatography step was added. The slurry was applied to the column was washed with 20 ml 20 mM Tris, pH7.5 containing 10% glycerol and 0.8 mM imidazole and step eluted with 2 column volumes of the same buffer made in 40, 50, 60, 100, 200, 300 and 400 mM imidazole.

Protein purification of Single Chain Anaio(genin (ScANG). ScANG was prepared as described for ScEDN with the following exception; the refolded protein was made 5% glycerol before application to a 4 ml CM SEPHADEX C-50 column (4 ml column for each 160 mg of refolded protein). The column was washed with 2 column volumes of the same buffer made in 1M NaCl. The remaining procedure is as described for ScEDN.

G. Functional Assays

The chimeric antibody retains its functional binding characteristics when it is expressed as an RNase fusion protein but binds less well than the native antibody by a magnitude of 1–2 logs depending, on the particular batch.

The functional characteristics of the RNase portion of the single chain fusion proteins was assessed by two methods. They demonstrate RNase activity using tRNA as the RNA substrate in the standard RNase A assay described above. The ScANG fusion is less potent than the ScEDN. The ability of the RNase protein to inhibit cell free protein synthesis was also measured. Both ScANG and ScEDN are potent inhibitors of cell free protein synthesis but less so than the native proteins. ScEDN was found to be more effective after the second chromatography step than after the first chromatography purification.

Neither Ang nor EDN have effects on K562 leukemia cells that express the human transferrin receptor but they inhibit protein synthesis in these cells when attached to an antibody that recognizes the receptor. Vero cells do not express this receptor and are unaffected, thus demonstrating targeting.

Thus, single chain-RNase fusion proteins can be made in bacteria. They retain functional characteristics of both binding and enzymatic components and can target tumor cells bearing the appropriate receptor. The concentration required is in the nM range and, similarly to the binding data, varies from batch to batch.

FIGS. 13A and 13B show that the ScANG (pET-11d-ANG-FB-E6-His6) and ScEDN (pET-11d-EDN-FB-E6-His6) bind less well than the native antibody by a magnitude of 1 to 2 logs depending on the particular batch in a standard binding assay with K562 cells. K562 cells ($10^6$ cells per ml) were placed in an Eppendorf tube with unlabeled ScEDN or parent E6 antibody and incubated at 4° C. for 30 minutes. Iodinated E6 was added to the cells for an additional 4 hours. The cell pellet was washed four times and then counted.

FIG. 14 shows the effect of inhibition of cell-free protein synthesis. Both ScANG and ScEDN are potent inhibitors of cell-free protein synthesis, but less so than the native proteins. The effect of the fusions is compared to ANG alone in FIG. 14. The in vitro translation assay was performed by incubating rabbit reticulocyte lysate with or without additions at the concentration specified for 60 minutes at 30° C. The incubation was in the presence of amino acids and 35S methionine. The amount of protein synthesis was determined by the incorporation of 35S methionine into products precipitable by 10% trichloroacetic acid.

FIG. 15. Neither ANG nor EDN have effects on K562 leukemia cells that express the human transferrin receptor but they inhibit protein synthesis in these cells when attached to an antibody that recognizes the receptor as shown in FIG. 15. Vero cells do not express this receptor and are unaffected by the fusion proteins. ScAng.His1.7 is equivalent to pET-11d-ANG-FB-E6-HIS6. HHScANG.conc is equivalent to pET-11d-ANG-E6. ScEDN.His3.3 is equivalent to pET-11d-EDN-FB-E6-HIS6. ScEDN Hep.4 is equivalent to pET-11d-E6-FB-EDN. The assay was similar to the one described in connection with FIG. 12.

Figure 16:
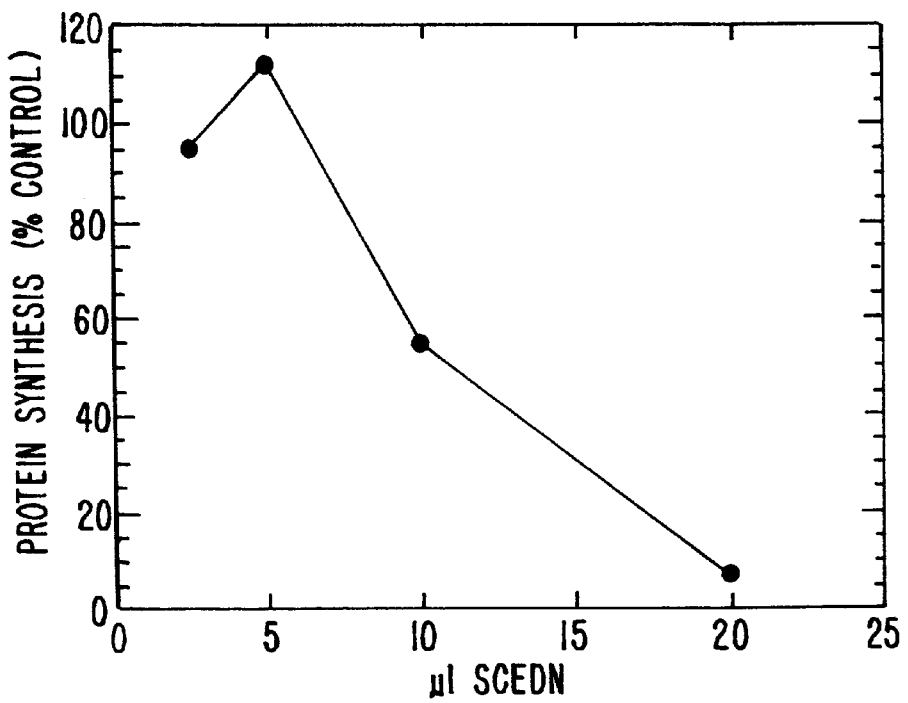

FIG. 16 shows a dose-dependent effect of ScEDN (pET-11d-EDN-FB-E6-HIS6) to inhibit protein synthesis on target K562 human leukemia cells, similar to that described for FIG. 3.

Figure 17:
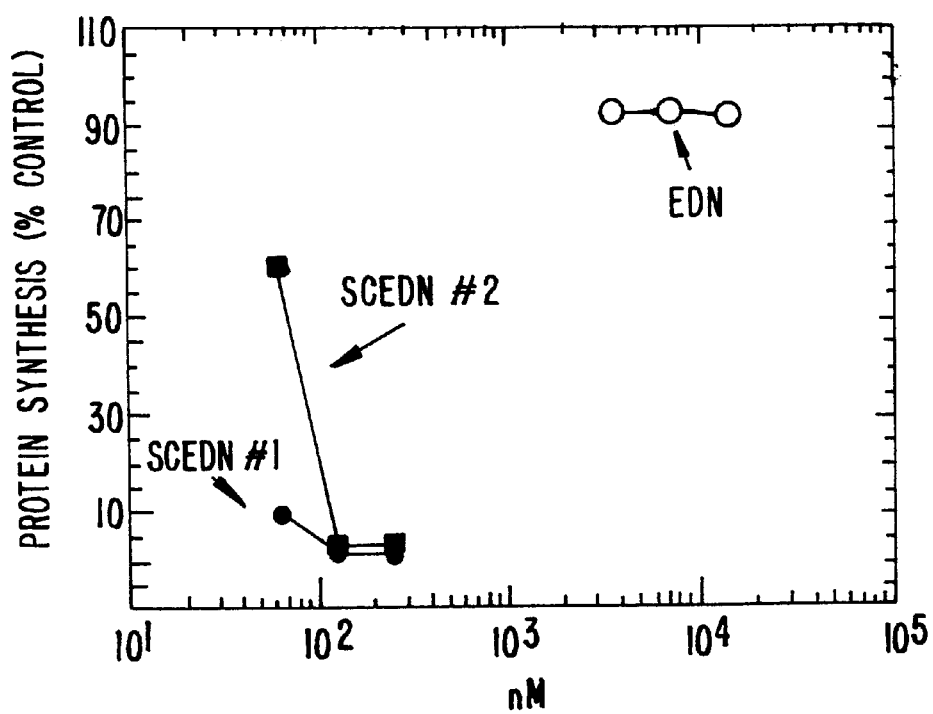

FIG. 17 shows that EDN alone has no effect on protein synthesis of K562 cells but that ScEDN is at least 2 logs more potent.

Figure 18A:
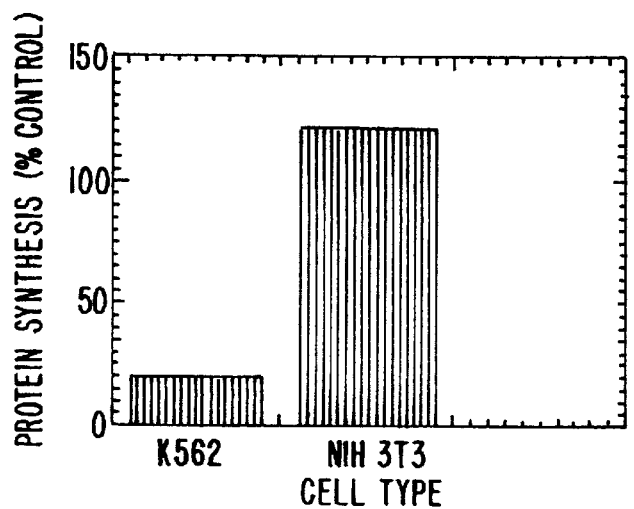
Figure 18B:
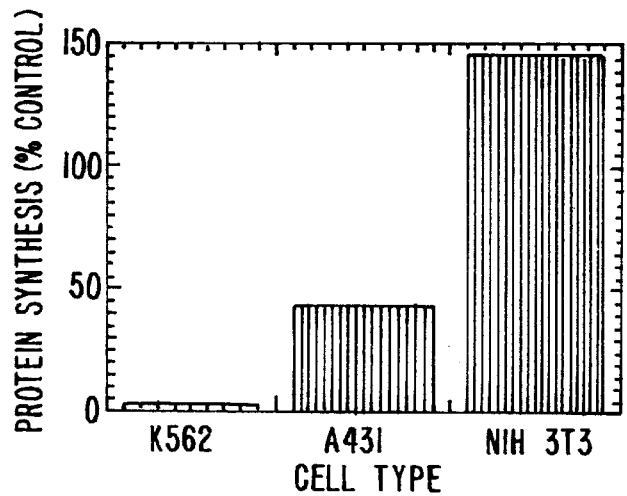
Figure 18C:
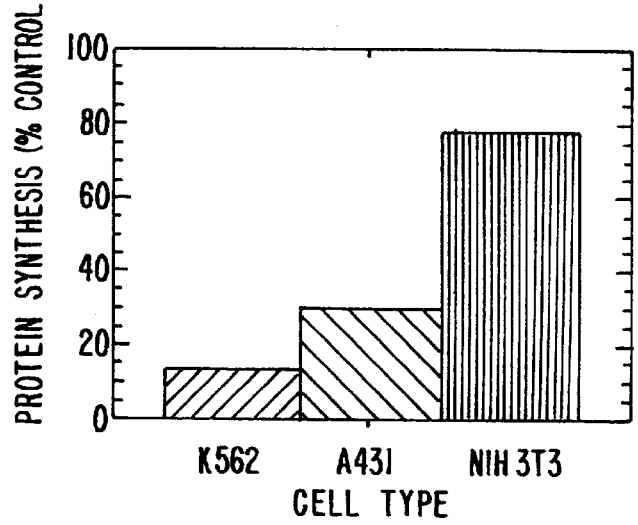

FIGS. 18A, 18B, and 18C represent three different experiments (A, B and C) and show that ScEDN inhibits protein synthesis in K562 cells which have more receptors than A431 cells and that it does not inhibit protein synthesis in NIH3T3 cells which do not have receptors for the human transferrin receptor.

FIG. 19 shows a sequence alignment of some members of the RNase A superfamily: Frog lectin is from *Rana catesbaiana* (SEQ ID NO:12), onconase (SEQ ID NO:13), EDN (SEQ ID NO:14) ECP (human eosinophil cationic protein, (SEQ ID NO:15), ANG is bovine angiogenin (SEQ ID NO:16), seminal is bovine seminal RNase (SEQ ID NO:17), and RNase A is bovine pancreatic RNase A (SEQ ID NO:18). Amino acids conserved in all members are capitalized, and active site residues H12, K41, and H119 (RNase A numbering) are marked with an asterisk.

All publications, including patents and patent applications, mentioned hereinabove are hereby incorporated by reference.

The foregoing invention has been described in some detail for purposes of clarity and understanding. It will also be obvious that various combinations in form and detail can be made without departing from the scope of the invention.

What is claimed is:

1. A nucleic acid construct which expresses the amino acid sequence for a functional pancreatic RNase and a protein which binds a specific cell surface marker on a target cell.

2. The nucleic acid construct of claim 1, wherein the RNase sequence is for angiogenin.

3. The nucleic acid construct of claim 2, wherein the RNase sequence is selected from the group consisting of SEQ ID NOs: 2 and 3.

4. The nucleic acid construct of claim 1, wherein the RNase sequence is for eosinophil-derived neurotoxin.

5. The nucleic acid construct of claim 4, wherein the RNase sequence is selected from the group consisting of SEQ ID NOs 5 and 6.

6. The nucleic acid construct of claim 1, wherein the RNase sequence is the sequence in SEQ ID NO:8 for human RNase.

7. The nucleic acid construct of claim 1, wherein the protein that binds a specific cell surface marker on a target cell is an antibody.

8. The nucleic acid construct of claim 7, in which the antibody is a humanized chimeric antibody.

9. The nucleic acid construct of claim 7, wherein the antibody binds a human transferrin receptor on a target cell.

10. A pharmaceutical composition comprising a selective cytotoxic reagent comprising a pancreatic RNase protein recombinantly fused to a protein which binds a specific cell surface marker on a target cell and a pharmaceutically acceptable carrier.

11. A method of selectively killing cells comprising contacting cells to be killed with a selective cytotoxic reagent comprising a pancreatic RNase protein recombinantly fused to a protein which binds a specific cell surface marker on a target cell.

12. A single nucleic acid construct which expresses the amino acid sequence for a functional pancreatic RNase and the heavy chain and light chain regions of an antibody.

* * * * *